United States Patent
Spencer et al.

(10) Patent No.: US 9,944,690 B2
(45) Date of Patent: Apr. 17, 2018

(54) METHODS FOR CONTROLLING T CELL PROLIFERATION

(71) Applicant: BELLICUM PHARMACEUTICALS, INC., Houston, TX (US)

(72) Inventors: David Spencer, Houston, TX (US); Aaron Edward Foster, Houston, TX (US); Kevin Slawin, Houston, TX (US)

(73) Assignee: BELLICUM PHARMACEUTICALS, INC., Houston, TX (US)

( * ) Notice: Subject to any disclaimer, the term of this patent is extended or adjusted under 35 U.S.C. 154(b) by 0 days.

(21) Appl. No.: 14/210,034

(22) Filed: Mar. 13, 2014

(65) Prior Publication Data

US 2014/0286987 A1 Sep. 25, 2014

Related U.S. Application Data

(60) Provisional application No. 61/783,445, filed on Mar. 14, 2013.

(51) Int. Cl.
*C07K 14/705* (2006.01)
*C07K 14/725* (2006.01)
*C07K 16/30* (2006.01)

(52) U.S. Cl.
CPC .... *C07K 14/70578* (2013.01); *C07K 14/7051* (2013.01); *C07K 14/70521* (2013.01); *C07K 16/3069* (2013.01); *C07K 2317/24* (2013.01); *C07K 2317/622* (2013.01); *C07K 2317/64* (2013.01); *C07K 2319/00* (2013.01); *C07K 2319/33* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 4,514,506 A | 4/1985 | Braatz et al. | |
| 5,384,253 A | 1/1995 | Krzyek et al. | |
| 5,538,880 A | 7/1996 | Lundquist et al. | |
| 5,550,214 A | 8/1996 | Eberlein et al. | |
| 5,550,318 A | 8/1996 | Eberlein et al. | |
| 5,589,343 A | 12/1996 | Marchand et al. | |
| 5,610,042 A | 3/1997 | Chang et al. | |
| 5,645,992 A | 7/1997 | Lott et al. | |
| 5,648,226 A | 7/1997 | Van Den Eynde et al. | |
| 5,709,995 A | 1/1998 | Chisari et al. | |
| 5,719,054 A | 2/1998 | Bouursnell et al. | |
| 5,741,899 A | 4/1998 | Capone et al. | |
| 5,750,395 A | 5/1998 | Fikes et al. | |
| 5,780,036 A | 7/1998 | Chisari | |
| 5,830,462 A | 11/1998 | Crabtree et al. | |
| 5,834,266 A | 11/1998 | Crabtree et al. | |
| 5,840,839 A | 11/1998 | Wang et al. | |
| 5,869,337 A | 2/1999 | Crabtree et al. | |
| 5,869,608 A | 2/1999 | Cadlwell et al. | |
| 5,871,753 A | 2/1999 | Crabtree et al. | |
| 5,925,565 A | 7/1999 | Berlioz et al. | |
| 5,935,819 A | 8/1999 | Eichner et al. | |
| 5,955,596 A | 9/1999 | Zagursky et al. | |
| 5,965,242 A | 10/1999 | Patton et al. | |
| 5,994,313 A | 11/1999 | Crabtree et al. | |
| 6,011,018 A | 1/2000 | Crabtree et al. | |
| 6,043,082 A | 3/2000 | Crabtree et al. | |
| 6,046,047 A | 4/2000 | Crabtree et al. | |
| 6,046,158 A | 4/2000 | Ariizumi et al. | |
| 6,054,436 A | 4/2000 | Crabtree et al. | |
| 6,497,876 B1 | 12/2002 | Maraskovsky et al. | |
| 6,558,951 B1 | 5/2003 | Tomai et al. | |
| 6,670,186 B1 | 12/2003 | Nair et al. | |
| 6,943,245 B2 | 9/2005 | Killary et al. | |
| 7,404,950 B2 | 7/2008 | Spencer et al. | |
| 8,404,817 B2 | 3/2013 | Sherman et al. | |
| 8,691,210 B2 | 4/2014 | Spencer et al. | |
| 8,822,647 B2 * | 9/2014 | Jensen | A61K 48/005 424/93.21 |
| 8,999,949 B2 | 4/2015 | Spencer et al. | |
| 9,428,569 B2 | 8/2016 | Spencer | |
| 2003/0082163 A1 | 5/2003 | Shu | |
| 2003/0091593 A1 | 5/2003 | Bachmann et al. | |
| 2003/0092132 A1 | 5/2003 | Williams | |
| 2003/0108527 A1 | 6/2003 | Seya et al. | |
| 2003/0147881 A1 * | 8/2003 | Cheung | A61K 47/48653 424/131.1 |
| 2003/0153518 A1 | 8/2003 | Foxwell et al. | |
| 2003/0206917 A1 | 11/2003 | Tykocinski et al. | |
| 2003/0232055 A1 | 12/2003 | Medzhitov | |
| 2004/0019195 A1 | 1/2004 | Scholm et al. | |
| 2004/0116333 A1 | 6/2004 | Lin et al. | |
| 2004/0209836 A1 | 10/2004 | Spencer | |
| 2005/0113564 A1 * | 5/2005 | Campana | C07K 14/70517 530/350 |
| 2005/0215472 A1 | 9/2005 | Schulke et al. | |
| 2006/0247191 A1 | 11/2006 | Finney et al. | |
| 2007/0081963 A1 | 4/2007 | Oh et al. | |
| 2008/0269160 A1 | 10/2008 | Spencer et al. | |
| 2008/0274140 A1 | 11/2008 | Weiner et al. | |

(Continued)

FOREIGN PATENT DOCUMENTS

| | | |
|---|---|---|
| EP | 0273085 | 7/1988 |
| EP | 0 510 691 | 10/1992 |
| WO | WO 94/09699 | 5/1994 |
| WO | WO 94/018317 | 8/1994 |
| WO | WO 96/012796 | 5/1996 |

(Continued)

OTHER PUBLICATIONS

Carpenito et al., 2009, Proc Natl Acad Sci U S A 106:3360-3365.*

(Continued)

*Primary Examiner* — Ilia Ouspenski
(74) *Attorney, Agent, or Firm* — Grant IP, Inc.

(57) ABSTRACT

The technology relates generally to the field of immunology and relates in part to compositions and methods for controlling the proliferation of T cells, for example, therapeutic T cells. The methods further relate to compositions and methods for inducing an immune response in a subject.

15 Claims, 22 Drawing Sheets

(56) References Cited

U.S. PATENT DOCUMENTS

| | | | |
|---|---|---|---|
| 2009/0175880 A1 | 7/2009 | Keler et al. | |
| 2009/0311183 A1 | 12/2009 | Devy et al. | |
| 2010/0105136 A1* | 4/2010 | Carter | C07K 14/7051 435/372.3 |
| 2010/0196336 A1 | 8/2010 | Park et al. | |
| 2010/0203067 A1 | 8/2010 | Spencer et al. | |
| 2011/0033383 A1* | 2/2011 | Spencer | C07K 14/70578 424/9.1 |
| 2011/0201780 A1 | 8/2011 | Reed et al. | |
| 2011/0286980 A1 | 11/2011 | Brenner et al. | |
| 2011/0287038 A1 | 11/2011 | Slawin et al. | |
| 2013/0071414 A1* | 3/2013 | Dotti | C12N 5/0636 424/184.1 |
| 2013/0131315 A1 | 5/2013 | Su | |
| 2013/0183333 A1 | 7/2013 | Spencer et al. | |
| 2013/0280220 A1* | 10/2013 | Ahmed | C12N 15/85 424/93.21 |
| 2013/0287748 A1 | 10/2013 | June | |
| 2013/0287752 A1* | 10/2013 | Davila | C07K 16/44 424/93.71 |
| 2013/0295110 A1 | 11/2013 | Binder | |
| 2013/0315884 A1* | 11/2013 | Galetto | C12N 5/0636 424/93.71 |
| 2013/0323834 A1 | 12/2013 | Brenner | |
| 2014/0023647 A1 | 1/2014 | Slawin et al. | |
| 2014/0087468 A1 | 3/2014 | Spencer et al. | |
| 2014/0120622 A1* | 5/2014 | Gregory | A61K 35/26 435/462 |
| 2014/0134142 A1* | 5/2014 | Smith | C07K 16/2803 424/93.21 |
| 2014/0255360 A1 | 9/2014 | Spencer et al. | |
| 2014/0255363 A1* | 9/2014 | Metelitsa | A61K 39/00 424/93.21 |
| 2014/0286987 A1 | 9/2014 | Spencer et al. | |
| 2014/0287490 A1 | 9/2014 | Spencer et al. | |
| 2014/0308259 A1* | 10/2014 | Scholler | C07K 16/2827 424/93.21 |
| 2015/0111294 A1 | 4/2015 | Spencer et al. | |
| 2015/0139943 A1 | 5/2015 | Campana et al. | |
| 2015/0306140 A1 | 10/2015 | Spencer et al. | |
| 2015/0328292 A1 | 11/2015 | Spencer et al. | |
| 2016/0046700 A1 | 2/2016 | Foster et al. | |
| 2016/0058857 A1 | 3/2016 | Spencer et al. | |
| 2017/0002321 A1 | 1/2017 | Spencer et al. | |
| 2017/0182140 A1 | 6/2017 | Spencer et al. | |

FOREIGN PATENT DOCUMENTS

| | | |
|---|---|---|
| WO | WO 01/083551 | 11/2001 |
| WO | WO 02/036769 | 5/2002 |
| WO | WO 04/073641 | 9/2004 |
| WO | WO 2005/044996 | 5/2005 |
| WO | WO 08/049113 | 4/2008 |
| WO | WO 09/061996 | 5/2009 |
| WO | WO 10/033949 | 5/2010 |
| WO | WO 11/130566 | 10/2011 |
| WO | WO 11/146862 | 11/2011 |
| WO | WO 2012/079000 | 6/2012 |
| WO | WO 2012/127464 | 9/2012 |
| WO | WO 2013/126720 | 8/2013 |
| WO | WO 13/154760 | 10/2013 |
| WO | WO 14/127261 | 8/2014 |
| WO | WO 14/151960 | 9/2014 |
| WO | WO 14/164348 | 10/2014 |
| WO | WO 14/197638 | 12/2014 |
| WO | WO 15/123527 | 8/2015 |
| WO | WO 16/036746 | 3/2016 |

OTHER PUBLICATIONS

Ladanyi A. (2015) Pigment Cell Melanoma Res. 28; 490-500.*
Warner et al. MyD88: A Critical Adaptor Protein in Innate Immunity Signal Transduction. J. Immunol. 2013; 190: 3-4.*
Chang et al. Transgene-enforced co-stimulation of CD4+ T cells leads to enhanced and sustained anti-tumor effector functioning. Cytotherapy 2007; 9: 771-784.*
Adema, G. J., et al., Nature, Jun. 12, 1997. 387: p. 713-7.
Anderson, D. M., et al., Nature, Nov. 13, 1997, 390: p. 175-9.
Anurathapan, U. et al. Kinetics of tumor destruction by chimeric antigen receptor-modified T cells. Molecular therapy : the journal of the American Society of Gene Therapy 22, 623-633 (2014).
Arcone, et al., (1988) Nucl. Acids Res., 16(8), 3195-3207.
Ardeshna KM, et al., Blood. 2000;96:1039-1046.
Banchereau J, et al., Ann N Y Acad Sci. 2003; 987:180-187.
Banchereau, J., & Steinman, R. M., Nature 392, 245-252 (1998).
Banchereau, J., et al., Annu Rev Immunol, 2000,. 18: p. 767-811.
Bander NH, et al., J Clin Oncol. 23: 4591-601, 2005.
Becker ML, Near R, Mudgett-Hunter M, et al: Expression of a hybrid immunoglobulin-T cell receptor protein in transgenic mice. Cell 58:911-21, 1989.
Bennett, S. R., et al., . Nature, Jun. 4, 1998, 393: p. 478-80.
Bernard et al., AIDS, 12(16):2125-2139, 1998.
Bianco FJ, et al., Cancer Symposium: Abstract 278, 2005.
Blau, C. A. et al., Proc Natl Acad.Sci. USA 1997, 94:3076-3081.
Bojak, A., et al., 2002. Vaccine 20:1975-79.
Bollard, C.J., et al., (2002) Blood 99:3179-3187.
Bollard, C.M., et al., (2004) J. Exptl. Med. 200:1623-1633.
Brentjens RJ, Davila ML, Riviere I, et al: CD19-targeted T cells rapidly induce molecular remissions in adults with chemotherapy-refractory acute lymphoblastic leukemia. Sci Transl Med 5:177ra38, 2013.
Carpenito, et al: Control of large, established tumor xenografts with genetically retargeted human T cells containing CD28 and CD137 domains. Proc Natl Acad Sci U S A 106:3360-5, 2009.
Carter RE, et al., Proc Natl Acad Sci U S A. 93: 749-53, 1996.
Caux, C. Adv Exp Med Biol. 1997, 417:21-5.
Cazeaux, N., et al., 2002. Vaccine 20:3322-31.
Chang SS, et al., Clin Cancer Res. 5: 2674-81, 1999.
Chang SS, et al., Urology. 57: 801-5, 2001.
Chatteijee, et al., (1995) Ann. N.Y. Acad. Sci., 770,79-90.
Chen and Okayama, Mol. Cell Biol., 7(8):2745-2752, 1987.
Chen et al PNAS 94: 1914-1918, 1997.
Cheung, Y.K., et al., 2004. Vaccine 23:629-38.
Christiansen JJ, et al., Mol Cancer Ther. 4: 704-14, 2005.
Ciceri, F. et al. Antitumor effects of HSV-TK-engineered donor lymphocytes after allogeneic stem-cell transplantation. Blood 109, 4698-4707 (2007).
Clackson T (2006) Chem Biol Drug Des 67:440-2.
Clarke, S. R., J Leukoc Biol, May 2000. 67: p. 607-14.
Coffin, (1990) In: Virology, ed., New York: Raven Press, pp. 1437-1500.
Cohen et al Nucleic Acid Res. 18:2807-2808, 1990.
Coupar et al., Gene, 68:1-10, 1988.
Craddock JA, Lu A, Bear A, et al: Enhanced tumor trafficking of GD2 chimeric antigen receptor T cells by expression of the chemokine receptor CCR2b. J Immunother 33:780-8, 2010.
Crawford ED, et al., N Engl J Med. 321: 419-24, 1989.
de la Taille A, et al., Cancer Detect Prev. 24: 579-88, 2000.
Deml, L.A., et al., 2001. J. Virol. 75:1099-11001.
Di Stasi, A. et al. Inducible apoptosis as a safety switch for adoptive cell therapy. The New England journal of medicine 365, 1673-1683 (2011).
Donnelly, J.J., et al., 1997. Annu. Rev. Immunol. 15:617-48.
Donnelly, ML 2001, J. Gen. Virol. 82:1013-25.
Dotti, G., Gottschalk, S., Savoldo, B. & Brenner, M.K. Design and development of therapies using chimeric antigen receptor-expressing T cells. Immunological reviews 257, 107-126 (2014).
Farrar et al., "Activation of the Raf-1 kinase cascade by courmycin-induced dimerization," Nature 383, Sep. 12, 1996, 178-181.
Fearon et al. "The instructive role of innate immunity in the acquired immune response," (1996) Science 272: 50-53.
Fechheimer et al., (1987) Proc. Nat'l Acad. Sci. USA, 84,8463-8467.

(56) References Cited

OTHER PUBLICATIONS

Fedorov, V.D., Themeli, M. & Sadelain, M. PD-1- and CTLA-4-based inhibitory chimeric antigen receptors (iCARs) divert off-target immunotherapy responses. Science translational medicine 5, 215ra172 (2013).
Fernandez, N. C., et al.,. Nat Med, Apr. 5, 1999: p. 405-11.
Ferrari et al., (1996) J. Virol., 70,3227-3234.
Ferraro, B. et al., Human Vaccines 7:120-127 (2011).
Finney HM, Akbar AN, Lawson AD: Activation of resting human primary T cells with chimeric receptors: costimulation from CD28, inducible costimulator, CD134, and CD137 in series with signals from the TCR zeta chain. J Immunol 172:104-13, 2004.
Finney HM, Lawson AD, Bebbington CR, et al: Chimeric receptors providing both primary and costimulatory signaling in T cells from a single gene product. J Immunol 161:2791-7, 1998.
Fisher et al., "Transduction with Recombinant Adeno-Associated Virus for Gene Therapy Is Limited by Leading-Strand Synthesis" (1996) J. Virol., 70,520-532.
Fisher, D.T. et al. IL-6 trans-signaling licenses mouse and human tumor microvascular gateways for trafficking of cytotoxic T cells. The Journal of clinical investigation 121, 3846-3859 (2011).
Flotte et al., Proc. Nat'l Acad. Sci. USA, 90,10613-10617, (1993).
Foster, A.E. et al. Autologous designer antigen-presenting cells by gene modification of T lymphocyte blasts with IL-7 and IL-12. Journal of immunotherapy 30, 506-516 (2007).
Freeman LM, et al., Q J Nucl Med. 46: 131-7, 2002.
Gaubert, G.; Wengel, J. "Synthesis of 1-(2'O-methyl-β-d-ribofuranosyl)-5-nitroindole and its phosphoramidite derivative," Tetrahedron Letters 2004, 45, 5629-5632.
Gauthier-Campbell et al., Molecular Biology of the Cell 15: 2205-2217 (2004).
Gay, N.J., Symmons, M.F., Gangloff, M. & Bryant, C.E. Assembly and localization of Toll-like receptor signalling complexes. Nature reviews. Immunology 14, 546-558 (2014).
Gefter et al., Somatic Cell Genet., 3:231-236, 1977.
Gestwicki, J.E., et al., Combinatorial Chem. & High Throughput Screening 10:667-675 (2007).
Gibson, D.G. et al. Enzymatic assembly of DNA molecules up to several hundred kilobases. Nature methods 6, 343-345 (2009).
Gilboa, E, Nat Rev Cancer 4, 401-11 (2004).
Gilboa, E. & Vieweg, J., Immunol Rev 199, 251-63 (2004).
Gittes RF, N Engl J Med. 324: 236-45, 1991.
Galbiati et al., "N-terminal fatty acylation of the alpha-subunit of the G-protein Gi1 : only the myristoylated protein is a substrate for palmitoylation." Biochem. J. 303: 697-700 (1994).
Goodman et al. (1994), Blood, 84,1492-1500.
Goodwin JS, Curr Opin Immunol. 1989;2:264-268.
Goodwin JS, et al., J Exp Med. 1977;146:1719-1734.
Gopal, T.V., Mol Cell Biol. May 1985;5(5):1188-90.
Gossen and Bujard, Proc. Natl. Acad. Sci. USA, 89:5547-5551, 1992.
Gossen et al., Science, 268:1766-1769, 1995.
Goverman J, Gomez SM, Segesman KD, et al: Chimeric immunoglobulin-T cell receptor proteins form functional receptors: implications for T cell receptor complex formation and activation. Cell 60:929-39, 1990.
Graham and van der Eb, (1973) Virology, 52,456-467.
Gross G, Waks T, Eshhar Z: Expression of immunoglobulin-T-cell receptor chimeric molecules as functional receptors with antibody-type specificity. Proc Natl Acad Sci U S A 86:10024-8, 1989.
Gross, G., and Eshar, Z., FASEB Journal 6:3370-3378 (1992).
Grupp, S.A. et al. Chimeric antigen receptor-modified T cells for acute lymphoid leukemia. The New England journal of medicine 368, 1509-1518 (2013).
Guedan S, Chen X, Madar A, et al: ICOS-based chimeric antigen receptors program bipolar TH17/TH1 cells. Blood, 2014, 1070-1080.
Hanks BA, et al., Nat Med. 2005;11:130-137.
Hauer et al., PNAS 102(8): 2874-2879 (2005)).
Hay, R.T., et al., J Mol Biol. Jun. 5, 1984;175(4):493-510.
Haynes, N.M., et al. J. Immunol. 166:182-7 (2001).
Hearing and Shenk, (1983) J. Mol. Biol. 167,809-822.
Hearing et al., J. (1987) Virol., 67, 2555-2558.
Ho, S. N. et al., Nature 1996, 382:822-826.
Hollstein et al Nucleic Acids Res. 22:3551-3555, 1994.
Holsinger, L. J. et al., Proc.Natl.Acad.Sci. USA 1995, 95:9810-9814.
Hombach A, Wieczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
Imai C, Mihara K, Andreansky M, et al: Chimeric receptors with 4-1BB signaling capacity provoke potent cytotoxicity against acute lymphoblastic leukemia. Leukemia 18:676-84, 2004.
Inman, B.A., Frigola, X., Dong, H. & Kwon, E.D. Costimulation, coinhibition and cancer. Current cancer drug targets 7, 15-30 (2007).
Introna, M. et al. Genetic modification of human T cells with CD20: a strategy to purify and lyse transduced cells with anti-CD20 antibodies. Human gene therapy 11, 611-620 (2000).
Ismaili J, et al., J Immunol. 2002;168:926-932.
Israeli et al Cancer Res. 53:227-230, 1993.
Israeli RS, et al., Cancer Res. 54: 1807-11, 1994.
Israeli RS, et al., Cancer Res. 54: 6306-10, 1994.
Iuliucci JD, et al., J Clin Pharmacol. 41: 870-9, 2001.
Jackson et al EMBOJ, 11:527-535, 1992.
Janeway et al. (1989) Cold Spring Harb. Symp. Quant. Biol., 54: 1-13.
Jemal A, et al., Cancer statistics, 2008. CA Cancer J Clin. 58: 71-96, 2008.
Jena, B., Moyes, J.S., Huls, H. & Cooper, L.J. Driving Car-based T-cell therapy to success. Current hematologic malignancy reports 9, 50-56 (2014).
Jensen MC, Popplewell L, Cooper LJ, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
Kadowaki N, et al., J Exp Med. 2001;194:863-869.
Kageyama et al., (1987) J. Biol. Chem., 262,2345-2351.
Kalinski P, Blood. 2001;97:3466-3469.
Kalinski P, Hilkens CM, Wierenga EA, et al: T-cell priming by type-1 and type-2 polarized dendritic cells: the concept of a third signal. Immunol Today 20:561-7, 1999.
Kalos, M. et al. T cells with chimeric antigen receptors have potent antitumor effects and can establish memory in patients with advanced leukemia. Science translational medicine 3, 95ra73 (2011).
Kamburov, A., Wierling, C., Lehrach, H. & Herwig, R. ConsensusPathDB—a database for integrating human functional interaction networks. Nucleic acids research 37, D623-628 (2009).
Kaplitt et al., (1994) Nat'l Genet., 8,148-153.
Kaplitt, M.G., et al., Ann Thorac Surg. Dec. 1996;62(6):1669-76.
Katari, U.L. et al. Engineered T cells for pancreatic cancer treatment. HPB : the official journal of the International Hepato Pancreato Biliary Association 13, 643-650 (2011).
Kawakami et al Proc. Nat'l Acad. Sci. USA 91:6458-6462, 1992.
Kawakrni et al, J. Exp. Med. 180:347-352, 1994.
Kelly WK and Slovin SF, Curr Oncol Rep. 2: 394-401, 2000.
Kemnade JO, Seethammagari M, Narayanan P, et al: Off-the-shelf Adenoviral-mediated Immunotherapy via Bicistronic Expression of Tumor Antigen and iMyD88/CD40 Adjuvant. Mol Ther, Jul. 2012;20(7):1462-71.
Kershaw MH, Westwood JA, Parker LL, et al: A phase I study on adoptive immunotherapy using gene-modified T cells for ovarian cancer. Clin Cancer Res 12:6106-15, 2006.
Kessler et al., (1996) Proc. Nat'l Acad. Sci. USA, 93,14082-14087.
Klein et al., (1987) Nature, 327,70-73.
Kloss, C.C., Condomines, M., Cartellieri, M., Bachmann, M. & Sadelain, M. Combinatorial antigen recognition with balanced signaling promotes selective tumor eradication by engineered T cells. Nature biotechnology 31, 71-75 (2013).

(56) References Cited

OTHER PUBLICATIONS

Kochenderfer, J.N. et al. Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor. Journal of clinical oncology : official journal of the American Society of Clinical Oncology (2014), 540-549.
Koeberl et al., (1997) Proc. Nat'l Acad. Sci. USA, 94,1426-1431.
Kohler & Milstein, Eur. J. Immunol., 6:511-519, 1976.
Kohler & Milstein, Nature, 256:495-497, 1975.
Kopytek, S.J., et al., Chemistry & Biology 7:313-321 (2000).
Kraaij R, et al., Prostate. 62: 253-9, 2005.
Kuby, 2000, Immunology, 4.sup.th edition, W.H. Freeman.
Kumar, S., et al., 2006. DNA Cell Biol. 25:383-92.
Kutzler, M.A., and Weiner, D.B., 2008. Nature Rev. Gen. 9:776-88.
Kutzler, M.A., et al., 2005. J. Immunol. 175:112-125.
Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
Kwon et al PNAS 84:7473-7477, 1987.
Laddy, D.J., et al., 2008. PLoS.ONE 3 e2517.
Lanitis, E. et al. Chimeric antigen receptor T Cells with dissociated signaling domains exhibit focused antitumor activity with reduced potential for toxicity in vivo. Cancer immunology research 1, 43-53 (2013).
Lanzavecchia, A. and F. Sallusto, Science, 2000. 290: p. 92-96.
Lapointe R, et al., Eur J Immunol. 2000;30:3291-3298.
Lee DW, Gardner R, Porter DL, et al: Current concepts in the diagnosis and management of cytokine release syndrome. Blood 124:188-95, 2014.
Levrero et al., Gene, 101:195-202, 1991.
Leyton, J.V. et al. Engineered humanized diabodies for microPET imaging of prostate stem cell antigen-expressing tumors. Protein engineering, design & selection: PEDS 22, 209-216 (2009).
Leyton, J.V. et al. Humanized radioiodinated minibody for imaging of prostate stem cell antigen-expressing tumors. Clinical cancer research: an official journal of the American Association for Cancer Research 14, 7488-7496 (2008).
Li, V., et al., 2000. Virology 272:417-28.
Linette, G.P. et al. Cardiovascular toxicity and titin cross-reactivity of affinity-enhanced T cells in myeloma and melanoma. Blood 122, 863-871 (2013).
Liu H, et al., Cancer Res. 57: 3629-34, 1997.
Liu H, et al., Cancer Res. 58: 4055-60, 1998.
Luft T, et al., Blood. 2002;100:1362-1372.
Luo, Z. et al., Nature 1996,383:181-185.
MacCorkle, R. A. et al., Proc Natl Acad Sci USA 1998, 95:3655-3660.
Macejak and Sarnow, Nature, 353:90-94, 1991.
Maher J, Brentjens RJ, Gunset G, et al: Human T-lymphocyte cytotoxicity and proliferation directed by a single chimeric TCRzeta /CD28 receptor. Nat Biotechnol 20:70-5, 2002.
Malin, A.S., et al., 2000. Microbes Infect. 2:1677-85.
Mann et al., (1983) Cell, 33,153-159.
Martin S, Pahari S, Sudan R, et al: CD40 signaling in CD8⁺CD40⁺ T cells turns on contra-T regulatory cell functions. J Immunol 184:5510-8, 2010.
Maude, S.L. et al. Chimeric antigen receptor T cells for sustained remissions in leukemia. The New England journal of medicine 371, 1507-1517 (2014).
McCown et al., (1996) Brain Res., 713,99-107.
McWhirter, S. M., et al., Proc Natl Acad Sci U S A, Jul. 20, 1999, 96: p. 8408-13.
Medzhitov et al., "A human homologue of the *Drosophila* Toll protein signals activation of immunity," Letters to Nature, Nature vol. 388:394-397, Jul. 24, 1997.
Meylan, E., et al., Nature (2006) 442:39-44.

Milone MC, Fish JD, Carpenito C, et al: Chimeric receptors containing CD137 signal transduction domains mediate enhanced survival of T cells and increased antileukemic efficacy in vivo. Mol Ther 17:1453-64, 2009.
Mizukami et al., (1996) Virology, 217,124-130.
Montgomery, D.L., et al., 1993. DNA Cell Biol. 12:777-83.
Morgan, R.A., et al., "Case Report of a Serious Adverse Event Following the Administration of T Cells Transduced With a Chimeric Antigen Receptor Recognizing ERBB2" (2010) Molecular Therapy 18:843-851.
Nabel et al., Science, 244(4910):1342-1344, 1989.
Narayanan P, Lapteva N, Seethammagari M, et al: A composite MyD88/CD40 switch synergistically activates mouse and human dendritic cells for enhanced antitumor efficacy. J Clin Invest 121:1524-34, 2011.
Narum, D.L., et al., 2001. 69:7250-55.
Ni, C., et al., PNAS, 2000, 97(19): 10395-10399.
Nicolau et al., (1987) Methods Enzymol., 149,157-176.
Nociari et al., J. Immunol. Methods, 213(2): 157-167, 1998.
Ohshima, Y., et al., J Immunol, Oct. 15, 1997, 159: p. 3838-48.
Oliviero et al., (1987) EMBO J., 6, 1905-1912.
O'Neill DW, et al., Blood. 2004;104:2235-2246.
Page, B., et al., Anticancer Res. Jul.-Aug. 1998;18(4A):2313-6.
Park JR, Digiusto DL, Slovak M, et al: Adoptive transfer of chimeric antigen receptor re-directed cytolytic T lymphocyte clones in patients with neuroblastoma. Mol Ther 15:825-33, 2007.
Paskind et al., (1975) Virology, 67,242-248.
Pelletier and Sonenberg, Nature, 334:320-325, 1988.
Perales et al., Proc. Natl. Acad. Sci. USA, 91:4086-4090, 1994.
Philip, B. et al. A highly compact epitope-based marker/suicide gene for easier and safer T-cell therapy. Blood 124, 1277-1287 (2014).
Ping et al., (1996) Microcirculation, 3,225-228.
Pinto JT, et al., Clin Cancer Res. 2: 1445-51, 1996.
Poli and Cortese, (1989) Proc. Nat'l Acad. Sci. USA, 86,8202-8206.
Porter, D.L., Levine, B.L., Kalos, M., Bagg, A. & June, C.H. Chimeric antigen receptor-modified T cells in chronic lymphoid leukemia. The New England journal of medicine 365, 725-733 (2011).
Potter et al., (1984) Proc. Nat'l Acad. Sci. USA, 81, 7161-7165.
Prowse and Baumann, (1988) Mol Cell Biol, 8,42-51.
Pule, et al: A chimeric T cell antigen receptor that augments cytokine release and supports clonal expansion of primary human T cells. Mol Ther 12:933-41, 2005.
Pule, et al: Virus-specific T cells engineered to coexpress tumor-specific receptors: persistence and antitumor activity in individuals with neuroblastoma. Nat Med 14:1264-70, 2008.
Pullen, S.S., et al., J Biol Chem, May 14, 1999, 274: p. 14246-54.
Ramos CA, Dotti G: Chimeric antigen receptor (CAR)-engineered lymphocytes for cancer therapy. Expert Opin Biol Ther 11:855-73, 2011.
Renan, M. J. (1990) Radiother Oncol., 19, 197-218.
Rescigno M, et al., J Exp Med. 1998;188:2175-2180.
Rickert, R.C., Jellusova, J. & Miletic, A.V. Signaling by the tumor necrosis factor receptor superfamily in B-cell biology and disease. Immunological reviews 244, 115-133 (2011).
Ridge, J. P., D. R. F, and P. Nature, Jun. 4, 1998. 393: p. 474-8.
Rippe et al., Mol. Cell Biol., 10:689-695, 1990.
Rivera, V. M. et al., Nat.Med. 1996, 2:1028-1032.
Riviere, et al., "Effects of retroviral vector design on expression of human adenosine deaminase in murine bone marrow transplant recipients engrafted with genetically modified cells" PNAS, USA 92, 6733-6737 (1995).
Ron, et al., (1991) Mol. Cell. Biol., 2887-2895.
Rosenberg SA, Immunity. 1999;10:281-287.
Roux, et al., (1989) Proc. Nat'l Acad. Sci. USA, 86, 9079-9083.
Sallusto, F., et al., Eur J Immunol, Sep. 28, 1998: p. 2760-9.
Samulski et al., J. Virol., 61:3096-3101 (1987).
Sardesai, N.Y., and Weiner, D.B., Current Opinion in Immunotherapy 23:421-9 (2011).
Savoldo B, Ramos CA, Liu E, et al: CD28 costimulation improves expansion and persistence of chimeric antigen receptor-modified T cells in lymphoma patients. J Clin Invest 121:1822-6, 2011.
Scandella E, et al., Blood. 2002;100:1354-1361.

(56) References Cited

OTHER PUBLICATIONS

Schellhammer PF, et al., J Urol. 157: 1731-5, 1997.
Schenten D, Nish SA, Yu S, et al: Signaling through the adaptor molecule MyD88 in CD4+ T cells is required to overcome suppression by regulatory T cells. Immunity 40:78-90, 2014.
Scher HI, et al., J Natl Cancer Inst. 88: 1623-34, 1996.
Scher, H.I. and Kelly, W.K., Journal of Clinical Oncology 11, 1566-72 (1993).
Schneider, R. M., et al., 1997. J. Virol. 71:4892-4903.
Schoenberger, S. P., et al., Nature, Jun. 4, 1998 393: p. 480-3.
Schweitzer et al., J. Org. Chem., 59:7238-7242 (1994).
Silver DA, et al., Clin Cancer Res. 3: 81-5, 1997.
Simpson et al., Gastroenterology, 115(4):849-855, 1998.
Small EJ and Srinivas S, Cancer. 76: 1428-34, 1995.
Small EJ and Vogelzang NJ, J Clin Oncol. 15: 382-8, 1997.
Smith, J.M., et al., 2004. AIDS Res. Hum. Retroviruses 20:1335-47.
Snyder DS, Nature. 1982;299:163-165.
Song, D.G. et al. CD27 costimulation augments the survival and antitumor activity of redirected human T cells in vivo. Blood 119, 696-706 (2012).
Spencer D. M. et al., Curr Biol 1996, 6:839-847.
Spencer D. M. et al., Proc.Natl.Acad.Sci. USA 1995, 92:9805-9809.
Spencer DM, et al., Science. 1993;262:1019-1024.
Steinman RM, Annu Rev Immunol. 2003;21:685-711.
Straathof, K.C. et al. An inducible caspase 9 safety switch for T-cell therapy. Blood 105, 4247-4254 (2005).
Strober, W., et al., Nature Reviews (2006) 6:9-20.
Su SL, et al., Cancer Res. 55: 1441-3, 1995.
Subramanian et al. "Gene set enrichment analysis: a knowledge-based approach for interpreting genome-wide expression profiles", PNAS, USA, 102, 15545-15550 (2005).
Tai et al., Cancer Research 64, 2846-2852 (2004).
Ten Klooster JP et al, Biology of the Cell (2007) 99, 1-12.
Tepler, I, et al. (1989) J. Biol. Chem. 264:5912.
Termeer, C. C., et al., J Immunol, Aug. 15, 2000. 165: p. 1863-70.
Tibbetts et. al. (1977) Cell, 12,243-249.
Till, et al: "CD20-specific adoptive immunotherapy for lymphoma using a chimeric antigen receptor with both CD28 and 4-1BB domains: pilot clinical trial results". Blood 119:3940-50, 2012.
Tone, M., et al., Proc Natl Acad Sci U S A, 2001. 98(4): p. 1751-1756.
Troyer JK, et al., Int J Cancer. 62: 552-8, 1995.
Tur-Kaspa et al., (1986) Mol. Cell Biol., 6,716-718.
Van der Pouw Kraan TC, et al., J Exp Med. 1995;181:775-779.
Vera, J. et al. "T lymphocytes redirected against the kappa light chain of human immunoglobulin efficiently kill mature B lymphocyte-derived malignant cells", Blood 108, 3890-3897 (2006).
Vieweg J, et al., Springer Semin Immunopath. 2005;26:329-341.
Vincent, S., et al., Nature Biotechnology 21:936-40, 1098 (2003).
Wagner et al., Proc. Natl. Acad. Sci. USA, 87(9):3410-3414, 1990.
Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
Wang, S., et al., 2006. Vaccine 24:4531-40.
Werts C., et al., Cell Death and Differentiation (2006) 13:798-815.
Wilson et al., (1990) Mol. Cell. Biol., 6181-6191.
Wilson et al., Science, 244:1344-1346, 1989.
Wright GL, Jr., et al., Urology. 48: 326-34, 1996.
Wu and Wu, (1987) J. Biol. Chem., 262, 4429-4432.
Wu and Wu, Adv. Drug Delivery Rev., 12:159-167, 1993.
Wu, X., et al., 2004. Biochem. Biophys. Res. Commun. 313:89-96.
Xiao et al., (1996) J. Virol., 70,8098-8108.
Xu, Z.L., et al. 2001. Gene 272:149-56.
Yadava, A., and Ockenhouse, C.F., 2003. Infect. Immun. 71:4962-69.
Yan, J. et al., 2007. Mol. Ther. 15:411-21.
Yang et al., (1990) Proc. Nat'l Acad. Sci. USA, 87, 9568-9572.
Yang, J.S., et al., 2002. Emerg. Infect. Dis. 8:1379-84.
Yvon E, Del Vecchio M, Savoldo B, et al: Immunotherapy of metastatic melanoma using genetically engineered GD2-specific T cells. Clin Cancer Res 15:5852-60, 2009.
Zechner et al., Mol. Cell. Biol., 2394-2401, 1988.
Zhang, W., et al., 2006. Biochem. Biophys. Res. Commun. 349:69-78.
Zhang, Y., et al., "Transduction of human T cells with a novel T-cell receptor confers anti-HCV reactivity", PLoS Pathog. Jul. 29, 2010;6(7).
Zhao Y, Wang QJ, Yang S, et al: A herceptin-based chimeric antigen receptor with modified signaling domains leads to enhanced survival of transduced T lymphocytes and antitumor activity. J Immunol 183:5563-74, 2009.
Zhong XS, et al., Mol Ther. Feb. 2010; 18(2):413-20.
Zhou, W., et al., 2002. Vet. Microbiol. 88:127-51.
Zitvogel L, et al., J Exp Med 1996. 183:87-97.
Zlakine et al., J. Cell Science 110: 673-679 (1997).
zur Megede, J., et al., 2000. J. Virol. 74:2628-2635.
International Search Report and Written Opinion dated Dec. 3, 2014 in International Application No. PCT/US2014/26734 filed Mar. 13, 2014 and published as: WO 2014/151960 on: Sep. 24, 2014.
ARIAD Pharmaceuticals, Inc., "ARGENT Regulated Homodimerization Kit" Version 2.0, product brochure, Sep. 9, 2002.
"Sipuleucel-T:APC 8015, APC-8015, prostate cancer vaccine—Dendreon." Drugs R D. 2006;7(3):197-201.
Adam et al., "Cross-linking of the p55 Tumor NecrosIs Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.
Adema et al., "Migration of dendritic cell based cancer vaccines: in vivo veritas?" Curr Opin Immunol. Apr. 2005;17(2):170-174.
Albert et al., "Dendritic cell maturation is required for the cross-tolerization of CD8+ T cells." Nat Immunol. Nov. 2001;2(11):1010-1017.
Aliprantis et al., "The apoptotic signaling pathway activated by Toll-like receptor-2," EMBO J. 19(13):3325-3336, (2000).
Amara et al, "A versatile synthetic dimerizer for the regulation of protein-protein interactions." PNAS 1997;94:10618-10623.
Amara et al., "Cell surface tagging and a suicide mechanism in a single chimeric human protein" Hum. Gene Ther. (1999) 10(16):2651-5.
Banchereau et al., "Dendritic cells as therapeutic vaccines against cancer." Nat Rev Immunol. Apr. 2005;5(4):296-306.
Belshaw et al. (Sep. 1996). "Controlling programmed cell death with a cyclophilin-cyclosporin-based chemical inducer of dimerization." Chemistry & Biology. 3(9): pp. 731-738.
Bennett et al., "Apoptosis of rat vascular smooth muscle cells is regulated by p53-dependent and -independent pathways." Circ Res. Aug. 1995;77(2):266-273.
Beutler B., "Inferences, questions and possibilities in Toll-like receptor signalling." Nature. Jul. 8, 2004;430(6996):257-263.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Bloom, J.D. and F.H. Arnold, In the light of directed evolution: pathways of adaptive protein evolution. Proc Natl Acad Sci U S A, 2009. 106 Suppl 1: p. 9995-10000.
Boatright, K.M. and G.S. Salvesen, Mechanisms of Caspase activation. Curr Opin Cell Biol, 2003. 15(6): p. 725-31.
Boatright, K.M., et al., A unified model for apical Caspase activation. Mol Cell, 2003. 11(2): p. 529-41.
Boldin et al., "Involvement of MACH, a Novel MORT1/FADD-Interacting Protease, in Fas/APO-1- and TNF Receptor-Induced Cell Death," Cell vol. 85, 803-815, Jun. 14, 1996.
Bonnert et al., GeneBank: AAC50954.1; GI: 1814020; Feb. 2, 1997.
Bonnert et al., GenBank Accession No. U84408, 1997.
Boss, W.F., et al., Basal signaling regulates plant growth and development. Plant Physiol, 2010. 154(2): p. 439-43.
Bowie et al, "Deciphering the message in protein sequences: tolerance to amino acid substitutions." Science Mar. 1990; 247:1306-1310.

(56) References Cited

OTHER PUBLICATIONS

Brady, S.C., L.A. Allan, and P.R. Clarke, Regulation of Caspase-9 through phosphorylation by protein kinase C zeta in response to hyperosmotic stress. Mol Cell Biol, 2005. 25(23): p. 10543-55.

Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.

Cardone, M.H., et al., Regulation of cell death protease Caspase-9 by phosphorylation. Science, 1998. 282(5392): p. 1318-21.

Caux et al., "Activation of human dendritic cells through CD40 cross-linking" J. Exp. Med. (1994) 180:1263-72.

Caux et al., "In vitro regulation of development and function of dendritic cells." Hematol Cell Ther. Oct. 1996;38(5):463.

Chan et al., "A Domain in TNF Receptors that mediates ligand-independent receptor assembly and signaling," Science 288, 2351-2354, (2001).

Chang, W.C., et al., Modifying ligand-induced and constitutive signaling of the human 5-HT4 receptor. PLoS One, 2007. 2(12): p. e1317.

Chan, Francis Ka-Ming, "Three is Better Than One: Pre-Ligand Receptor Assembly in the Regulation of TNF Receptor Signaling," Cytokine, Feb. 2007; 37(2) 101-107.

Chao, Y., et al., Engineering a dimeric Caspase-9: a re-evaluation of the induced proximity model for Caspase activation. PLoS Biol, 2005. 3(6): p. e183.

Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous Tumor-Associated Antigens, and Prime Naive Mice for a Cytotoxic T Lymphocyte Response," J. Exp. Med. vol. 190, No. 1, Jul. 5, 1999. pp. 125-133.

Choe et al., "Crystal structure of human toll-like receptor 3 (TLR3) ectodomain." Science. Jul. 22, 2005;309(5734):581-585.

Cisco et al., "Induction of human dendritic cell maturation using transfection with RNA encoding a dominant positive toll-like receptor 4." J Immunol. Jun. 1, 2004;172(11):7162-7168.

Clackson et al., "Redesigning an FKBP-ligand interface to generate chemical dimerizers with novel specificity." Proc Natl Acad Sci USA. Sep. 1, 1998;95(18):10437-10442.

Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.

Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).

Coffin "Molecular Mechanisms of Nucleic Acid Integration," Journal of Mecical Virology, 31:43-19 (1990).

Contin et al., "Membrane-anchored CD40 is processed by the tumor necrosis factor-alpha-converting enzyme. Implications for CD40 signaling." J Biol Chem. Aug. 29, 2003;278(35):32801-32809.

Cranmer et al., "Clinical applications of dendritic cell vaccination in the treatment of cancer." Cancer Immunol Immunother. Apr. 2004;54(4):275-306.

Cremer et al., "Long-lived immature dendritic cells mediated by TRANCE-RANK interaction." Blood. Nov. 15, 2002;100(10):3646-3655.

Cristofanilli et al., "Circulating tumor cells, disease progression, and survival in metastatic breast cancer." N Engl J Med. Aug. 19, 2004;351(8):781-91.

Cyster JG., "Chemokines and cell migration in secondary lymphoid organs." Science. Dec. 10, 1999;286(5447):2098-2102.

Dallal RM, Lotze MT., "The dendritic cell and human cancer vaccines." Curr Opin Immunol. Oct. 2000;12(5):583-588.

Davis et al., "Crystal structure of prostate-specific membrane antigen, a tumor marker and peptidase." Proc Natl Acad Sci USA. Apr. 26, 2005;102(17):5981-5986.

De Becker et al., "The adjuvant monophosphoryl lipid A increases the function of antigen-presenting cells." Int Immunol. Jun. 2000;12(6):807-815.

de Gruijl et al, "Prolonged Maturation and Enhanced Transduction of Dendritic Cells Migrated from Human Skin Explants After In Situ Delivery of CD40-Targeted Adenoviral Vectors," The Journal of Immunology vol. 169,2002 PQS 5322-5331.

De Vries et al., "Effective migration of antigen-pulsed dendritic cells to lymph nodes in melanoma patients is determined by their maturation state." Cancer Res. Jan. 1, 2003;63(1):12-17.

Deonarain, "Ligand-targeted receptor-mediated vectors for gene delivery," 1998, Expert Opin. Ther. Pat., vol. 8, pp. 53-69.

Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.

Donnelly et al., "DNA vaccines." Annu Rev Immunol. 1997;15:617-48.

Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.

Elgueta et al., "Molecular mechanism and function of CD40/CD40L engagement in the immune system," Immunological Reviews, 229, (2009) 152-172.

Evel-Kabler et al., "SOCS1 restricts dendritic cells' ability to break self tolerance and induce antitumor immunity by regulating IL-12 production and signaling." J Clin Invest. Jan. 2006;116(1):90-100.

Fan et al., "Improved artificial death switches based on caspases and FADD." Hum Gene Ther. Sep. 20, 1999;10(14):2273-2285.

Flotte TR, Carter BJ. "Adeno-associated virus vectors for gene therapy." Gene Ther. Aug. 1995;2(6):357-362.

Flotte, "Prospects for Virus-Based Gene Therapy for Cystic Fibrosis," Journal of Bioenergetics and Bioinformatics, vol. 25, No. 1, 1993.

Fujio Y, Walsh K., "Akt mediates cytoprotection of endothelial cells by vascular endothelial growth factor in an anchorage-dependent manner." J Biol Chem. Jun. 4, 1999;274(23):16349-16354.

GenBank Accession No. M29540,Human carcinoembryonic antigen mRNA (CEA), complete cds, Nov. 1, 1994.

Glode, "The case for adjuvant therapy for prostate cancer" Journal of Urology (2006) 176:S30-S33.

Granucci et al., "Early events in dendritic cell maturation induced by LPS." Microbes Infect. Nov. 1999;1(13):1079-1084.

Granucci et al., "Inducible IL-2 production by dendritic cells revealed by global gene expression analysis." Nat Immunol. Sep. 2001;2(9):882-888.

Granucci et al., "Modulation of cytokine expression in mouse dendritic cell clones." Eur J Immunol. Oct. 1994;24(10):2522-2526.

Grewal IS, Flavell RA., "CD40 and CD154 in cell-mediated immunity." Annu Rev Immunol. 1998;16:111-135.

Giudicelli et al., "IMGT/LIGM-DB, the IMGT comprehensive database of immunoglobulin and T cell receptor nucleotide sequences" Nucleic Acids Research (2006) 34:D781-4.

Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.

Harbury et al., "Crystal structure of an isoleucine-zipper trimer," Nature, vol. 371, Sep. 1, 1994, 80-83.

He et al., "A simplified system for generating recombinant adenoviruses." Proc Natl Acad Sci USA. Mar. 3, 1998;95(5):2509-2514.

Hermans et al., "CD8+ T cell-dependent elimination of dendritic cells in vivo limits the induction of antitumor immunity." J Immunol. Mar. 15, 2000;164(6):3095-3101.

Hodge et al., "Vector-based delivery of tumor-associated antigens and T-cell co-stimulatory molecules in the induction of immune responses and anti-tumor immunity," Cancer Detect Prevent 2002; 26;275-291.

Holler et al., "Development of improved soluble inhibitors of FasL and CD40L based on oligomerized receptors," Journal of Immunologial Methods 237(2000) 159-173.

(56) References Cited

OTHER PUBLICATIONS

Hong, T., et al., A simple theoretical framework for understanding heterogeneous differentiation of CD4+ T cells. BMC Syst Biol, 2012. 6: p. 66.
Horng et al., "*Drosophila* MyD88 is an adapter in the Toll signaling pathway," PNAS 98(22):12654-12658, Oct. 23, 2001.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hostager et al., "Different: CD40-mediated Signaling Events Require Distinct CD40 Structural features," J. Immunol. 157:1047-1053, Aug. 1, 1996.
Hou WS, Van Parijs L., "A Bcl-2-dependent molecular timer regulates the lifespan and immunogenicity of dendritic cells." Nat Immunol. Jun. 2004;5(6):583-589.
Hsiao, E.C., et al., Constitutive Gs activation using a single-construct tetracycline-inducible expression system in embryonic stem cells and mice. Stem Cell Res Ther, 2011. 2(2): p. 11.
Inaba et al., "Generation of large numbers of dendritic cells from mouse bone marrow cultures supplemented with granulocyte/macrophage colony-stimulating factor" J. Exp. Med. (1992) 176:1693-702.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.
Josien et al., "TRANCE, a tumor necrosis factor family member, enhances the longevity and adjuvant properties of dendritic cells in vivo." J Exp Med. Feb. 7, 2000;191(3):495-502.
Kagan JC, Medzhitov R., "Phosphoinositide-mediated adaptor recruitment controls Toll-like receptor signaling." Cell. Jun. 2, 2006;125(5):943-955.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kandel ES, Hay N., "The regulation and activities of the multi-functional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7):1099-105.
Kantoff et al., "Sipuleucel-T immunotherapy for castration-resistant prostate cancer." N Engl J Med. Jul. 29, 2010;363(5):411-22.
Kehry, Marilyn R., "CD40-Mediated Signaling in B Cells, Balancing Cell Survival, Growth and Death," The American Association of Immunologists, 1996, 2345-2348.
Kelleher et al., "Lipopolysaccharide Modulation of Dendritic Cells is Insufficient to Mature Dendritic Cells to Generate CTLs from Native Polyclonal CD8+ T Cells In Vitro, Whereas CD40 Ligation is Essential," The Journal of Immunology, The American Society of Immunologists, vol. 167, No. 11, Jan. 1, 2001, pp. 6247-6255.
Kempf et al, "Improved stimulation of human dendritic cells by receptor engagement with surface-modified microparticles," J Drug Target vol. 11 No. 1, Jan. 2003 pp. 11-18.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Kim et al., "High cleavage efficiency of a 2A peptide derived from porcine teschovirus-1 in human cell lines, zebrafish and mice" PLoS One (2011) 6(4):e18556.
Kobayashi et al., "IRAK-M is a negative regulator of Toll-like receptor signaling." Cell. Jul. 26, 2002;110(2):191-202.
Korst et al., "Effect of adenovirus gene transfer vectors on the immunologic functions of mouse dendritic cells." Mol Ther. Mar. 2002;5(3):307-315.
Krug et al., "Toll-like receptor expression reveals CpG DNA as a unique microbial stimulus for plasmacytoid dendritic cells which synergizes with CD40 ligand to induce high amounts of IL-12." Eur J. Immunol. 31:3026-3037.
Kouskoff, V., et al., B cell receptor expression level determines the fate of developing B lymphocytes: receptor editing versus selection. Proc Natl Acad Sci U S A, 2000. 97(13): p. 7435-9.
Kudo et al., "T lymphocytes expressing a CD16 signaling receptor exert antibody-dependent cancer cell killing" Cancer Research (2014) 74:93-103.
Labeur et al., "Generation of tumor immunity by bone marrow-derived dendritic cells correlates with dendritic cell maturation stage." J Immunol. Jan. 1, 1999;162(1):168-175.
Langenkamp et al., "Kinetics of dendritic cell activation: impact on priming of TH1, TH1 and nonpolarized T cells." Nat Immunol. Oct. 2000;1(4):311-316.
Lanzavecchia A, Sallusto F., "Regulation of T cell immunity by dendritic cells." Cell. Aug. 10, 2001;106(3):263-266.
Luning Prak, E.T., M. Monestier, and R.A. Eisenberg, B cell receptor editing in tolerance and autoimmunity. Ann N Y Acad Sci, 2011. 1217: p. 96-121.
Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.
Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.
Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.
Lee et al., "Cytoplasmic domain-mediated dimerizations of toll-like receptor 4 observed by beta-lactamase enzyme fragment complementation." J Biol Chem. Mar. 12, 2004;279(11):10564-10574.
Leo et al., "Partition coefficients and their uses." Chem Rev. Dec. 1971;71(6):525-616.
Li et al., "A novel conditional Akt 'survival+A185 switch' reversibly protects cells from apoptosis." Gene Ther. Feb. 2002;9(4):233-244.
Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.
Livak et al., "Analysis of relative gene expression data using real-time quantitative PCR and the 2(-Delta Delta C(T)) Method." Methods. Dec. 2001;25(4):402-408.
Lodge et al., Dendridic Cell-based Immunotherapy of Prostate Cancer: Immune Monitoring of a Phase II Clincal Trial, Cancer Res. 60:829-833, 2000.
Loiarro et al., "Peptide-mediated interference of TIR domain dimerization in MyD88 inhibits interleukin-1-dependent activation of NF-{kappa}B." J Biol. Chem. Apr. 22, 2005;280(16):15809-15814.
Luke et al., "The family of five: TIR-domain-containing adaptors in Toll-like receptors signaling" Nature Reviews Immunology (2007) 7:353-364.
Luliucci et al., "Intravenous safety and pharmacokinetics of a novel dimerizer drug, AP1903, in healthy volunteers" J. Clin. Pharmacol. (2001) 41:870-879.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.

(56) References Cited

OTHER PUBLICATIONS

Malissen B, Ewbank JJ., "'TaiLoRing' the response of dendritic cells to pathogens." Nat Immunol. Aug. 2005;6(8):750-769.
Marsland et al., "CCL19 and CCL21 induce a potent proinflammatory differentiation program in licensed dendritic cells." Immunity. Apr. 2005;22(4):493-505.
Martin, M.C., et al., Protein kinase A regulates Caspase-9 activation by Apaf-1 downstream of cytochrome c. J Biol Chem, 2005. 280(15): p. 15449-55.
Martln-Fontecha et al., "Regulation of dendritic cell migration to the draining lymph node: impact on T lymphocyte traffic and priming." J Exp Med. Aug. 18, 2003;198(4):615-621.
Mazouz et al., "CD40 triggering increases the efficiency of dendritic cells for antitumoral immunization." Cancer Immun. Mar. 27, 2002;2:2.
McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., Molecular Cell, 2:253-258, 1998.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Miga et al., "Dendritic cell longevity and T cell persistence is controlled by CD154-CD40 interactions." Eur J Immunol. Mar. 2001;31(3):959-965.
Mochizuki et al., "Akt protein kinase inhibits non-apoptotic programmed cell death induced by ceramide." J Biol Chem. Jan. 25, 2002;277(4):2790-2797.
Morgan et al., "Cancer regression in patients after transfer of genetically engineered lymphocytes." Science. Oct. 6, 2006;314(5796):126-129.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nakagami et al., "Safety and efficacy of docetaxel, estramustine phosphate and hydrocortisone in hormone-refractory prostate cancer patients." Int J Urol. Jul. 2010;17(7):629-34.
Napolitani et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1534, and Supplementary Materials pp. 1-16.
Narayanan et al., Abstract: 4761 "The iCD40.MyD88 combovector: A new platform for enhanced DC tumor immunotherapy", Proceedings of the American Association for Cancer Research Annual Meeting, vol. 51, Apr. 15, 2010.
Nestle et al., "Dendritic cells: On the move from bench to bedside." Nat Med. Jul. 2001;7(7):761-765.
Nishiya et al., "Ligand-regulated chimeric receptor approach reveals distinctive subcellular localization and signaling properties of the Toll-like receptors," J. Biol, Chem. 279(18):19008-19017, 2004.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen*," The Journal of Biological Chemistry, vol. 267, No. 15, May 25, 1992 10709-10715.
O'Sullivan B, Thomas R., "CD40 and dendritic cell function." Crit Rev Immunol. 2003;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Palecek et al., "Integrin-ligand binding properties govern cell migration speed through cell-substratum adhesiveness." Nature. Feb. 6, 1997;385(6616):537-540.
Papworth, C., Bauer, J. C., Braman, J. and Wright, D. A. , Site-directed mutagenesis in one day with >80% efficiency. Strategies, 1996. 9(3): p. 3-4.
Park et al, "An essential role for Akt1 in dendritic cell function and tumor immunotherapy," Nature Biology, vol. 24, No. 12, Dec. 2006, pp. 1581-1590.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Pasare C, Medzhitov R., "Toll pathway-dependent blockade of CD4+CD25+ T cell-mediated suppression by dendritic cells." Science. Feb. 14, 2003;299(5609):1033-1036.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.
Pruschy et al., "Mechanistic Sutdies of a Signaling Pathway Activated by the Organic Dimerizer FK1012," Chemistry and Biology 1994 vol. 1, No. 3, 163-172.
Puccetti et al., "Effects of IL-12 and IL-23 on antigen-presenting cells at the interface between innate and adaptive immunity." Crit Rev Immunol. 2002;22(5-6):373-390.
Raina, D., et al., c-Abl tyrosine kinase regulates Caspase-9 autocleavage in the apoptotic response to DNA damage. J Biol Chem, 2005. 280(12): p. 11147-51.
Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.
Randall, K.L., et al., Dock8 mutations cripple B cell immunological synapses, germinal centers and long-lived antibody production. Nat Immunol, 2009. 10(12): p. 1283-91.
Re F, Strominger JL., "Toll-Ike receptor 2(TLR2) and TLR4 differentially activate human dendritic cells." J Biol Chem. Oct. 5, 2001;276(40):37692-37699.
Reis e Sousa C., "Dendritic cells as sensors of infection." Immunity. May 2001;14(5):495-498.
Renatus, M., et al., Dimer formation drives the activation of the cell death protease Caspase-9. Proc Natl Acad Sci U S A, 2001. 98(25): p. 14250-5.
Resh et al., "Fatty acylation of proteins: new insights into membrane targeting of myristoylated and palmitoylated proteins" Biochim. Biophys. Acta. (1999) 1451:1-16.
Richard et al, "Expansion of Genetically modified Primary Human HemopOietic cells Using Chemical Inducers of Dimerization," Blood vol. 95, 2000 pp. 430-436.
Ridgway D., "The first 1000 dendritic cell vaccinees." Cancer Invest. 2003;21(6):873-886.
Riol-Blanco et al., "The chemokine receptor CCR7 activates in dendritic cells two signaling modules that independently regulate chemotaxis and migratory speed." J Immunol. Apr. 1, 2005;174(7):4070-4080.

(56) References Cited

OTHER PUBLICATIONS

Rivera, V.M., "Controlling Gene Expression USing SynthetiC Ligands," Methods: A companion to Methods in Enzymology vol. 14,1998 pp. 421-429.
Ronni et al., "Common interaction surfaces of the toll-like receptor 4 cytoplasmic domain stimulate multiple nuclear targets," Molecular and Cellular Biology, Apr. 2003, vol. 23, No. 7, pp. 2543-2555.
Roose, J.P., et al., T cell receptor-independent basal signaling via Erk and Abl kinases suppresses RAG gene expression. PLoS Biol, 2003. 1(2): p. E53.
Rudd, M.L., A. Tua-Smith, and D.B. Straus, Lck SH3 domain function is required for T-cell receptor signals regulating thymocyte development. Mol Cell Biol, 2006. 26(21): p. 7892-900.
Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.
Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.
Sanchez-Sanchez et al., "The multiple personalities of the chemokine receptor CCR7 in dendritic cells." J Immunol. May 1, 2006;176(9):5153-5159.
Sato et al., "Combination of monocyte-derived dendrinic cells and activated T cells which express CD40 ligand" an new approach to cancer Immunotherapy, Cancer Imminol Immunther, vol. 53, No. 1, Jan. 2004, pp. 53-61.
Scandella et al., "CCL19/CCL21-triggered signal transduction and migration of dendritic cells requires prostaglandin E2." Blood. Mar. 1, 2004;103(5):1595-1601.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7)1148-59.
Schuler et al., "The use of dendritic cells in cancer immunotherapy." Curr Opin Immunol. Apr. 2003; 15(2):138-147.
Schram, B.R., et al., B cell receptor basal signaling regulates antigen-induced Ig light chain rearrangements. J Immunol, 2008. 180(7): p. 4728-41.
Schuler et al., "Dendritic cells as adjuvants for immune-mediated resistance to tumors" J. Exp. Med. (1997) 186:1183-7.
Schultz et al., "CD40 triggering of heterodimeric IL-12 p70 production by dendritic cells in vivo requires a microbial priming signal," Immunity, vol. 13, No. 4, Oct. 2000. pp. 453-462.
Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).
Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
Shaffer et al., "Circulating tumor cell analysis in patients with progressive castration-resistant prostate cancer." Clin Cancer Res. Apr. 1, 2007;13(7):2023-9.
Shen et al., "Silencing of SOCS1 enhances antigen presentation by dendritic cells and antigen-specific anti-tumor immunity." Nat Biotechnol. Dec. 2004;22(12):1546-1553.
Shiozaki, E.N., J. Chai, and Y. Shi, Oligomerization and activation of Caspase-9, induced by Apaf-1 CARD. Proc Natl Acad Sci U S A, 2002. 99(7): p. 4197-202.
Shiozaki, E.N., et al., Mechanism of XIAP-mediated inhibition of Caspase-9. Mol Cell, 2003. 11(2): p. 519-27.
Shi, Y., Mechanisms of Caspase activation and inhibition during apoptosis. Mol Cell, 2002. 9(3): p. 459-70.
Smith et al., "Cognate CD4(+) T cell licensing of dendritic cells in CD8(+) T cell immunity." Nat Immunol. Nov. 2004;5(11):1142-1148.

Sonpavde, et al., "Vaccine therapy for prostate cancer", Urologic Oncology, Elsevier, NY, vol. 25, No. 6, Nov. 1, 2007, 451-459.
Sorensen et al., "Endostatin reduces cascularization, blood flow, and growth in a rat gliosarcoma." Neuro Oncol. Jan. 2002;4(1):1-8.
Sorkin, A. and M. von Zastrow, Endocytosis and signalling: intertwining molecular networks. Nat Rev Mol Cell Biol, 2009. 10(9): p. 609-22.
Spiegel, A.M., Defects in G protein-coupled signal transduction in human disease. Annu Rev Physiol, 1996. 58: p. 143-70.
Sporri R, Reis e Sousa C., "Inflammatory mediators are insufficient for full dendritic cell activation and promote expansion of CD4+ T cell populations lacking helper function." Nat Immunol. Feb. 2005;6(2):163-170.
Steinman RM, Pope M., "Exploiting dendritic cells to improve vaccine efficacy." J Clin Invest. Jun. 2002;109(12):1519-1526.
Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.
Stennicke, H.R., et al., Caspase-9 can be activated without proteolytic processing. J Biol Chem, 1999. 274(13): p. 8359-62.
Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.
Straathof, K.C., et al., An inducible Caspase-9 safety switch for T-cell therapy. Blood, 2005. 105(11): p. 4247-54.
Suarez-Alvarez et al, Epigenetic Mechanisms Regulate MHC and Antigen Processing Molecules in Human Embryonic and Induced Pluripotent Stem Cells. PLoS ONE (April) 5(4):e10192, 2010, pp. 1-12.
Suda et al., "Molecular Cloning and Expression of the Fas Ligand, a Novel Member of the Tumor Necrosis Factor Family," Cell vol. 75, 1169-1176 Dec. 17, 1993.
Szymczak et al., "Correction of multi-gene deficiency in vivo using a single 'self-cleaving' 2A peptide-based retroviral vector" Nature Biotechnology (2004) 22:589-94.
Tao, Y.X., Constitutive activation of G protein-coupled receptors and diseases: insights into mechanisms of activation and therapeutics. Pharmacol Ther, 2008. 120(2): p. 129-48.
Temin et al., (1986) In: Gene Transfer, Kucherlapati (ed.), New York: Plenum Press, pp. 149-188.
Thompson et al., "The low-toxicity versions of LPS, MPL adjuvant and RC529, are efficient adjuvants for CD4+ T Cells." J Leukoc Biol. Dec. 2005;78(6):1273-1280.
Timmerman et al., "Dendritic cell vaccines for cancer immunotherapy", Annu. Rev. Med. (1999) 50:507-29.
Tong et al, "Prospects for CD40-directed Experimental Therapy of Human Cancer," Cancer Gene Therapy vol. 10, 2003,pp. 1-13.
Tze, L.E., et al., Basal immunoglobulin signaling actively maintains developmental stage in immature B cells. PLoS Biol, 2005. 3(3): p. e82.
Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg, "Immunotherapy for Advanced Prostate Cancer," vol. 9 Suppl. 1 (2007) Reviews in Urology S29-S38.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "IL-12p70-Dependent Th1 Induction by Human B Cells Requires Combined Activation with CD40 Ligand and CpG DNA", Journal of Immunology, vol. 172, 2004, 954-963.
Waldner, C., et al., Double conditional human embryonic kidney cell line based on FLP and PhiC31 mediated transgene integration. BMC Res Notes, 2011. 4: p. 420.
Werneburg et al., "Molecular Characterization of CD40 Signaling Intermediates," The Journal of Biological Chemistry, vol. 276, Nov. 16, 2001, 43334-43342.

(56) References Cited

OTHER PUBLICATIONS

Wesemann et al., "Suppressor of cytokine signaling 1 inhibits cytokine induction of CD40 expression in macrophages." J Immunol. Sep. 1, 2002;169(5):2354-2360.
Wolchok et al., "Guidelines for the Evaluation of Immune Therapy Activity in Solid Tumors: Immune-Related Response Criteria," Clin Cancer Res 2009;15(23) Dec. 1, 2009, pp. 7412-7420.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Yanagawa Y, Onoe K., "CCL19 induces rapid dendritic extension of murine dendritic cells." Blood. Sep. 15, 2002;100(6):1948-1956.
Zhang et al., "Anti-melanoma activity of T cells redirected with a TCR-like chimeric antigen receptor" Scientific Reports (2014) 4:3571.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "Retargeting NK-92 for anti-melanoma activity by a TCR-like single-domain antibody" Immunol. Cell. Biol. (2013) 91(10):615-24.
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
zur Medege et al., "Expression and immunogenicity of sequence-modified human immunodeficiency virus type 1 subtype B pol and gagpol DNA vaccines." J Virol. Jun. 2003;77(11):6197-6207.
International Search Report and Written Opinion dated Jun. 29, 2015 in International Application No. PCT/US2015/015829, filed on Feb. 13, 2015 and published as WO 2015/123527 on Aug. 20, 2015.
International Preliminary Report on Patentability dated Sep. 24, 2015 in International Application No. PCT/US2014/026734, filed on Mar. 13, 2014 and published as WO 2014/151960 on Sep. 25, 2014.
International Search Report and Written Opinion dated Dec. 28, 2015 in International Application No. PCT/US2015/047957, filed on Sep. 1, 2015 and published as WO 2016/036749 on Mar. 10, 2016.
Geng et al., "Amplifying TLR-MyD88 signals within tumor-specific T cells enhances antitumor activity to suboptimal levels of weakly immunogenic tumor antigens" Cancer Research (2010) 70(19):7442-7454.
International Preliminary Report on Patentability dated Aug. 25, 2016 in International Application No. PCT/US2015/015829, filed on Feb. 13, 2015 and published as WO 2015/123527 on Aug. 20, 2015.
Extended European Search Report dated Sep. 21, 2016 in European Patent Application No. 14770399.5, filed on Mar. 13, 2014 and published as EP 2 968 502 on Jan. 20, 2016.
Search Report and Written Opinion dated Oct. 4, 2016 in Singapore Patent Application No. 11201506974X, filed on Mar. 13, 2014.
Curran et al., "Chimeric antigen receptors for T cell immunotherapy: current understanding and future directions" J. Gene Med. (2012) 14:405-415.
Extended European Search Report dated Jul. 4, 2017 in European Patent Application No. 15748478.3, filed on Feb. 13, 2015 and published as EP 3 104 866 on Dec. 21, 2016.
Collinson-Pautz et al., "MyD88/CD40 Genetic Adjuvant Function in Cutaneous Atypical Antigen-Presenting Cells Contributes to DNA Vaccine Immunogenicity" PLOS ONE (2016) 11(10):e0164547.
Foster et al., "Regulated Expansion and Survival of Chimeric Antigen Receptor-Modified T Cells Using Small Molecule-Dependent Inducible MyD88/CD40" Molecular Therapy (2017) 25(9):1-13.
Office Action dated May 8, 2017 in U.S. Appl. No. 14/191,167, filed Feb. 26, 2014 and Published as 2014-0287490 on Sep. 25, 2014.
Hacker et al., "Specificity in Toll-like receptor signalling through distinct effector functions of TRAF3 and TRAF6" Nature (2006) 439:204-207.
Nelson et al., "Toll-like receptor agonist therapy can profoundly augment the antitumor activity of adoptively transferred CD8(+) T cells without host preconditioning" J. Immunother. Cancer (2016) 4:6.
Paulos et al., "Microbial translocation augments the function of adoptively transferred self/tumor-specific CD8+ T cells via TLR4 signaling" J. Clin. Invest. (2007) 117:2197-2204.
International Preliminary Report on Patentability dated Mar. 16, 2017 in International Application No. PCT/US2015/047957, filed on Sep. 1, 2015 and published as WO 2016/036749 on Mar. 10, 2016.
Office Action dated Aug. 7, 2017 in U.S. Appl. No. 14/622,018, filed on Feb. 13, 2015 and published as US 2016-0046700 on Feb. 18, 2016.
Chicaybam et al., "Chimeric Antigen Receptors in Cancer Immuno-Gene Therapy: Current Status and Future Directions" International Reviews of Immunology (2011) 30(5-6):294-311.
Koehler et al., "Engineered T Cells for the Adoptive Therapy of B-Cell Chronic Lymphocytic Leukaemia" Advances in Hematology (2012) 2012:595060. doi: 10.1155/2012/595060 1-13.

* cited by examiner

```
                        SEQUENCE LISTING

<160> NUMBER OF SEQ ID NOS: 115

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atggggagta gcaagagcaa gcctaaggac cccagccagc gc                          42

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Gly Ser Ser Lys Ser Lys Pro Lys Asp Pro Ser Gln Arg
1               5                   10

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcgagtctg gcggtggatc cggag                                             25

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Glu Ser Gly Gly Gly Ser Gly
1               5
```

-continued

<210> SEQ ID NO 5
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ggcgttcaag tagaaacaat cagcccagga gacggaagga ctttccccaa acgaggccaa      60
acatgcgtag ttcattatac tgggatgctc gaagatggaa aaaaagtaga tagtagtaga     120
gaccgaaaca aaccatttaa atttatgttg ggaaaacaag aagtaataag gggctgggaa     180
gaaggtgtag cacaaatgtc tgttggccag cgcgcaaaac tcacaatttc tcctgattat     240
gcttacggag ctaccggcca ccccggcatc ataccccctc atgccacact ggtgtttgac     300
gtcgaattgc tcaaactgga a                                                321

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 gtcgag                                                                   6

<210> SEQ ID NO 8
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Glu
1

<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agccttcaa gttcatgctc ggcaagcagg aggtgatccg ggggtgggag     180
gagggcgtgg ctcagatgtc ggtcgggcaa cgagcgaagc ttaccatctc acccgactac     240
gcgtatgggg caacggggca tccgggaatt atccctcccc acgctacgct cgtattcgat     300
gtggagctct tgaagcttga g                                              321
```

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
tctggcggtg gatccggagt cgag                                            24
```

<210> SEQ ID NO 12
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 12

Ser Gly Gly Gly Ser Gly Val Glu
1               5

<210> SEQ ID NO 13
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ttctgggtac tggttgtagt cggtggcgta cttgcttgtt attctcttct tgttaccgta      60
gccttcatta tattctgggt ccgatcaaag cgctcaagac tcctccattc cgattatatg     120
aacatgacac ctcgccgacc tggtcctaca cgcaaacatt atcaaccota cgcaccccco     180 cgagacttcg ctgcttatcg atcc                                            204

<210> SEQ ID NO 14
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 ggatcc                                                                  6

<210> SEQ ID NO 16
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Gly Ser
1

<210> SEQ ID NO 17
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
agtgtagtta aaagaggaag aaaaaagttg ctgtatatat ttaaacaacc atttatgaga      60
ccagtgcaaa ccacccaaga agaagacgga tgttcatgca gattcccaga agaagaagaa     120
ggaggatgtg aattg                                                      135

<210> SEQ ID NO 18
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Val Val Lys Arg Gly Arg Lys Lys Leu Leu Tyr Ile Phe Lys Gln
1               5                   10                  15

Pro Phe Met Arg Pro Val Gln Thr Thr Gln Glu Glu Asp Gly Cys Ser
            20                  25                  30

Cys Arg Phe Pro Glu Glu Glu Gly Gly Cys Glu Leu
        35                  40                  45

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 acgcgt                                                                  6

<210> SEQ ID NO 20
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Arg
1

<210> SEQ ID NO 21
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cgggtcaaat tcagccggag tgctgacgcc ccagcatacc aacagggaca aaaccaactc    60
tacaacgagc tcaacctggg tagacgcgag gagtacgacg ttctggataa gaggcggggc   120
cgggacccag agatggggggg caaacctcag cggcggaaga acccgcagga gggtctttat   180
aacgagctcc agaaggacaa gatggcgaaa gcctattcag aaattgggat gaaaggcgag   240
agacgcaggg gaaaaggtca cgatggtctg tatcaaggac tgtcaaccgc caccaaagac   300
acttacgatg cgctccacat gcaggccctc cctccccgc                         339

<210> SEQ ID NO 22
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 gtcgac                                                               6

<210> SEQ ID NO 24
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Asp
1

<210> SEQ ID NO 25
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 25
cgcgcaaagc gt                                                              12

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Lys Arg
1

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaaaaccta tacctaatcc attgctgggc ttagactcaa ca                             42

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Pro Ile Pro Asn Pro Leu Leu Gly Leu Asp Ser Thr
1               5                   10

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggcagcggaa gc                                                              12

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ser Gly Ser
1

<210> SEQ ID NO 31
<211> LENGTH: 57
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcaacgaatt tttccctgct gaaacaggca ggggacgtag aggaaaatcc tggtcct          57

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Thr Asn Phe Ser Leu Leu Lys Gln Ala Gly Asp Val Glu Glu Asn
1               5                   10                  15

Pro Gly Pro

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 acgcgt                                                                   6

<210> SEQ ID NO 34
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Arg
1

<210> SEQ ID NO 35
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgccccctc ctagactgct gttttttcctg ctctttctca ccccaatgga agttagacct      60
gaggaaccac tggtcgttaa agtggaagaa ggtgataatg ctgtcctcca atgccttaaa     120
gggaccagcg acggaccaac gcagcaactg acttggagcc gggagtcccc tctcaagccg     180
tttctcaagc tgtcacttgg cctgccaggt cttggtattc acatgcgccc ccttgccatt     240
tggctcttca tattcaatgt gtctcaacaa atgggtggat ctacctttg ccagcccggc      300 cccccttctg agaaagcttg gcagcctgga tggaccgtca atgttgaagg ctccggtgag     360
ctgtttagat ggaatgtgag cgaccttggc ggactcggtt gcggactgaa aaataggagc     420
tctgaaggac cctcttctcc ctccggtaag ttgatgtcac ctaagctgta cgtgtgggcc     480
```

```
aaggaccgcc ccgaaatctg ggagggcgag cctccatgcc tgccgcctcg cgattcactg    540
aaccagtctc tgtcccagga tctcactatg gcgcccggat ctactctttg gctgtcttgc    600
ggcgttcccc cagatagcgt gtcaagagga cctctgagct ggacccacgt acaccctaag    660
ggccctaaga gcttgttgag cctggaactg aaggacgaca gacccgcacg cgatatgtgg    720
gtaatggaga ccggccttct gctccctcgc gctaccgcac aggatgcagg gaaatactac    780
tgtcatagag ggaatctgac tatgagcttt catctcgaaa ttacagcacg gcccgttctt    840
tggcattggc tcctccggac tggaggctgg aaggtgtctg ccgtaacact cgcttacttg    900 atttttttgcc tgtgtagcct ggttgggatc ctgcatcttc agcgagccct tgtattgcgc    960
cgaaaaagaa aacgaatgac tgaccctaca cgacgattct ga                      1002
```

<210> SEQ ID NO 36
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Pro Pro Pro Arg Leu Leu Phe Phe Leu Leu Phe Leu Thr Pro Met
1               5                   10                  15

Glu Val Arg Pro Glu Glu Pro Leu Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
```

-continued

```
                    260                 265                 270
Glu Ile Thr Ala Arg Pro Val Leu Trp His Trp Leu Leu Arg Thr Gly
            275                 280                 285
Gly Trp Lys Val Ser Ala Val Thr Leu Ala Tyr Leu Ile Phe Cys Leu
        290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe
                    325                 330
```

<210> SEQ ID NO 37
<211> LENGTH: 63
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 37
atggagtttg gctgtcatg gctgttcctc gtggccattc tcaaagggggt ccagtgttct    60 cgc    63

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 38

```
Met Gly Phe Gly Leu Ser Trp Leu Phe Leu Val Ala Ile Leu Lys Gly
1               5                   10                  15
Val Gln Cys Ser Arg
            20
```

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 39
gggggaggag gttctggagg cggcgggagc ggaggaggag gcagc    45

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 40

```
Gly Gly Gly Gly Ser Gly Gly Gly Gly Ser Gly Gly Gly Gly Ser
1               5                   10                  15
```

<210> SEQ ID NO 41
<211> LENGTH: 6
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 41 ggatcc 6

<210> SEQ ID NO 42
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Gly Ser
1

<210> SEQ ID NO 43
<211> LENGTH: 714
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43

```
gatccagccg aacccaaatc ccccgataaa acacatactt gccccccttg tcccgcacca      60
gaattgcttg gcggaccttc cgttttcctt tttcccccca aacctaaaga taccctgatg     120
atttcccgaa cccctgaagt tacgtgcgta gtcgtagatg tgtctcacga agatccagaa     180
gtaaaattta actggtacgt agatggagtc gaagttcaca acgcaaagac gaagccccga     240
gaagaacaat ataattccac ataccgagta gttagcgttc tcaccgtact gcatcaggac     300
tggcttaacg gcaaagaata taaatgtaag gtctcaaaca aagcactccc agcccctatc     360
gaaaagacta tctccaaagc taaggacaa ccccgcgaac cccaggtcta tacacttccc     420
ccctcacgcg atgaactcac taaaaatcag gtttcccttaa cttgtcttgt caaaggcttc     480
taccctagcg atatcgcagt cgaatgggaa tccaatggcc agcccgaaaa caactataaa     540
acaaccccac ctgtcctcga ttcagatggc tcattctttc tctattccaa actgactgta     600
gacaaatccc gatggcaaca aggtaacgtg ttctcttgct cagtcatgca tgaagcgctt     660
cataaccatt acacacaaaa atctctctca ctgtctcccg aaagaagga cccc           714
```

<210> SEQ ID NO 44
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Asp Pro Ala Glu Pro Lys Ser Pro Asp Lys Thr His Thr Cys Pro Pro
1               5                  10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

```
Trp Tyr Val Asp Gly Val Glu Val His Asn Ala Lys Thr Lys Pro Arg
 65                  70                  75                  80

Glu Glu Gln Tyr Asn Ser Thr Tyr Arg Val Val Ser Val Leu Thr Val
             85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys Lys Asp Pro
225                 230                 235

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 ctcgag                                                                       6

<210> SEQ ID NO 46
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Glu
1

<210> SEQ ID NO 47
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
aaactgtgtt acctcctcga tggcatcctc tttatttatg gcgtgattct gaccgcattg     60
tttctccgag taaaattctc tagatccgca gacgctcccg catatcagca aggacaaaat    120
cagctttata cgaacttaa cctcggcaga cgcgaagaat acgatgtact ggacaagaga    180
agaggaagag atcccgaaat gggcggaaaa ccccagagaa gaagaatcc ccaagaaggt    240
```

```
ctttataacg aactgcagaa agataaaatg gccgaagcgt acagtgaaat tggtatgaaa     300
ggagaaagaa gacgcggaaa aggacatgac ggactctacc aaggactctc aactgctact     360
aaagatacat acgacgccct tcatatgcaa gccctccccc cgagataa                  408
```

```
<210> SEQ ID NO 48
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

Lys Leu Cys Tyr Leu Leu Asp Gly Ile Leu Phe Ile Tyr Gly Val Ile
1               5                   10                  15

Leu Thr Ala Leu Phe Leu Arg Val Lys Phe Ser Arg Ser Ala Asp Ala
            20                  25                  30

Pro Ala Tyr Gln Gln Gly Gln Asn Gln Leu Tyr Asn Glu Leu Asn Leu
        35                  40                  45

Gly Arg Arg Glu Glu Tyr Asp Val Leu Asp Lys Arg Arg Gly Arg Asp
    50                  55                  60

Pro Glu Met Gly Gly Lys Pro Gln Arg Arg Lys Asn Pro Gln Glu Gly
65                  70                  75                  80

Leu Tyr Asn Glu Leu Gln Lys Asp Lys Met Ala Glu Ala Tyr Ser Glu
                85                  90                  95

Ile Gly Met Lys Gly Glu Arg Arg Arg Gly Lys Gly His Asp Gly Leu
            100                 105                 110

Tyr Gln Gly Leu Ser Thr Ala Thr Lys Asp Thr Tyr Asp Ala Leu His
        115                 120                 125

Met Gln Ala Leu Pro Pro Arg
    130                 135

```
<210> SEQ ID NO 49
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gttgccgcca tcctgggcct gggcctggtg ctggggctgc tgggccccct ggccatcctg      60
ctggccctgt acctgctccg ggaccagagg ctgccccccg atgcccacaa gccccctggg     120
ggaggcagtt tccggacccc catccaagag gagcaggccg acgcccactc caccctggcc     180
aagatc                                                                186
```

```
<210> SEQ ID NO 50
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

Val Ala Ala Ile Leu Gly Leu Gly Leu Val Leu Gly Leu Leu Gly Pro
1               5                   10                  15

Leu Ala Ile Leu Leu Ala Leu Tyr Leu Leu Arg Arg Asp Gln Arg Leu
            20                  25                  30

Pro Pro Asp Ala His Lys Pro Pro Gly Gly Gly Ser Phe Arg Thr Pro
        35                  40                  45

Ile Gln Glu Glu Gln Ala Asp Ala His Ser Thr Leu Ala Lys Ile
    50                  55                  60

<210> SEQ ID NO 51
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
tgaaagaccc cacctgtagg tttggcaagc tagcttaagt aacgccattt tgcaaggcat    60
ggaaaaatac ataactgaga atagaaaagt tcagatcaag gtcaggaaca gatggaacag   120
ctgaatatgg gccaaacagg atatctgtgg taagcagttc ctgccccggc tcagggccaa   180
gaacagatgg aacagctgaa tatgggccaa acaggatatc tgtggtaagc agttcctgcc   240
ccggctcagg gccaagaaca gatggtcccc agatgcggtc cagccctcag cagtttctag   300
agaaccatca gatgtttcca gggtgcccca aggacctgaa atgaccctgt gccttatttg   360
aactaaccaa tcagttcgct tctcgcttct gttcgcgcgc ttatgctccc cgagctcaat   420
aaaagagccc acaacccctc actcggggcg ccagtcctcc gattgactga gtcgcccggg   480
tacccgtgta tccaataaac cctcttgcag ttgcatccga cttgtggtct cgctgttcct   540
tgggagggtc tcctctgagt gattgactac ccgtcagcgg gggtctttca              590

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gccgagggca ggggaagtct tctaacatgc ggggacgtgg aggaaaatcc cgggccc       57

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Glu Gly Arg Gly Ser Leu Leu Thr Cys Gly Asp Val Glu Glu Asn
1               5                   10                  15

Pro Gly Pro

<210> SEQ ID NO 54
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
tgaaagaccc cacctgtagg tttggcaagc tagcttaagt aacgccattt tgcaaggcat    60

```
ggaaaaatac ataactgaga atagagaagt tcagatcaag gtcaggaaca gatggaacag    120
ctgaatatgg gccaaacagg atatctgtgg taagcagttc ctgccccggc tcagggccaa    180
gaacagatgg aacagctgaa tatgggccaa acaggatatc tgtggtaagc agttcctgcc    240
ccggctcagg gccaagaaca gatggtcccc agatgcggtc cagccctcag cagtttctag    300
agaaccatca gatgtttcca gggtgcccca aggacctgaa atgaccctgt gccttatttg    360
aactaaccaa tcagttcgct tctcgcttct gttcgcgcgc ttctgctccc cgagctcaat    420
aaaagagccc acaacccctc actcggggcg ccagtcctcc gattgactga gtcgcccggg    480
tacccgtgta tccaataaac cctcttgcag ttgcatccga cttgtggtct cgctgttcct    540
tgggagggtc tcctctgagt gattgactac ccgtcagcgg gggtctttca              590
```

```
<210> SEQ ID NO 55
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
```

```
ctcgagtctg gcggtggatc cggaggcgtt caagtagaaa caatcagccc aggagacgga     60
aggactttcc ccaaacgagg ccaaacatgc gtagttcatt atactgggat gctcgaagat    120
ggaaaaaaag tagatagtag tagagaccga acaaaccat ttaaatttat gttgggaaaa     180
caagaagtaa taaggggctg ggaagaaggt gtagcacaaa tgtctgttgg ccagcgcgca    240
aaactcacaa tttctcctga ttatgcttac ggagctaccg ccacccccgg catcataccc    300
cctcatgcca cactggtgtt tgacgtcgaa ttgctcaaac tggaagtcga gggagtgcag    360
gtggagacga ttagtcctgg ggatgggaga acctttccaa agcgcggtca gacctgtgtt    420
gtccactaca ccggtatgct ggaggacggg aagaaggtgg actcttcacg cgatcgcaat    480
aagcctttca gttcatgct cggcaagcag gaggtgatcc gggggtggga ggagggcgtg    540
gctcagatgt cggtcgggca acgagcgaag cttaccatct cacccgacta cgcgtatggg    600
gcaacggggc atccgggaat tatccctccc cacgctacgc tcgtattcga gtggagctc    660 ttgaagcttg agtctggcgg tggatccgga gtcgac                              696
```

```
<210> SEQ ID NO 56
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56
```

Leu Glu Ser Gly Gly Gly Ser Gly Gly Val Gln Val Glu Thr Ile Ser
1               5                   10                  15

Pro Gly Asp Gly Arg Thr Phe Pro Lys Arg Gly Gln Thr Cys Val Val
            20                  25                  30

His Tyr Thr Gly Met Leu Glu Asp Gly Lys Lys Val Asp Ser Ser Arg
        35                  40                  45

Asp Arg Asn Lys Pro Phe Lys Phe Met Leu Gly Lys Gln Glu Val Ile
    50                  55                  60

Arg Gly Trp Glu Glu Gly Val Ala Gln Met Ser Val Gly Gln Arg Ala
65                  70                  75                  80

```
Lys Leu Thr Ile Ser Pro Asp Tyr Ala Tyr Gly Ala Thr Gly His Pro
                85                  90                  95

Gly Ile Ile Pro Pro His Ala Thr Leu Val Phe Asp Val Glu Leu Leu
            100                 105                 110

Lys Leu Glu Val Glu Gly Val Gln Val Glu Thr Ile Ser Pro Gly Asp
        115                 120                 125

Gly Arg Thr Phe Pro Lys Arg Gly Gln Thr Cys Val Val His Tyr Thr
    130                 135                 140

Gly Met Leu Glu Asp Gly Lys Lys Val Asp Ser Ser Arg Asp Arg Asn
145                 150                 155                 160

Lys Pro Phe Lys Phe Met Leu Gly Lys Gln Glu Val Ile Arg Gly Trp
                165                 170                 175

Glu Glu Gly Val Ala Gln Met Ser Val Gly Gln Arg Ala Lys Leu Thr
            180                 185                 190

Ile Ser Pro Asp Tyr Ala Tyr Gly Ala Thr Gly His Pro Gly Ile Ile
        195                 200                 205

Pro Pro His Ala Thr Leu Val Phe Asp Val Glu Leu Leu Lys Leu Glu
    210                 215                 220

Ser Gly Gly Gly Ser Gly Val Asp
225                 230

<210> SEQ ID NO 57
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
ggcgttcaag tagaaacaat cagcccagga gacggaagga ctttccccaa acgaggccaa      60
acatgcgtag ttcattatac tgggatgctc gaagatggaa aaaaagtaga tagtagtaga    120
gaccgaaaca aaccatttaa atttatgttg ggaaaacaag aagtaataag gggctgggaa    180
gaaggtgtag cacaaatgtc tgttggccag cgcgcaaaac tcacaatttc tcctgattat    240
gcttacggag ctaccggcca ccccggcatc atacccccctc atgccacact ggtgtttgac    300
gtcgaattgc tcaaactgga a                                              321

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80
```

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agcctttcaa gttcatgctc ggcaagcagg aggtgatccg ggggtgggag     180
gagggcgtgg ctcagatgtc ggtcgggcaa cgagcgaagc ttaccatctc acccgactac     240
gcgtatgggg caacggggca tccgggaatt atccctcccc acgctacgct cgtattcgat     300
gtggagctct tgaagcttga g                                              321

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 61

<400> SEQUENCE: 61

000

<210> SEQ ID NO 62

<400> SEQUENCE: 62

000

<210> SEQ ID NO 63

-continued

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75
<400> SEQUENCE: 75

000

<210> SEQ ID NO 76
<400> SEQUENCE: 76

000

<210> SEQ ID NO 77
<400> SEQUENCE: 77

000

<210> SEQ ID NO 78
<400> SEQUENCE: 78

000

<210> SEQ ID NO 79
<400> SEQUENCE: 79

000

<210> SEQ ID NO 80
<400> SEQUENCE: 80

000

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
atggggagta gcaagagcaa gcctaaggac cccagccagc gc            42

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Met Gly Ser Ser Lys Ser Lys Pro Lys Asp Pro Ser Gln Arg
1               5                   10

<210> SEQ ID NO 83
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 ctcgag                                                                6

<210> SEQ ID NO 84
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Glu
1

<210> SEQ ID NO 85
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atggccgctg ggggcccagg cgccggatca gctgctcccg tatcttctac ttcttctttg     60
ccgctggctg ctctgaacat gcgcgtgaga agacgcctct ccctgttcct taacgttcgc    120
acacaagtcg ctgccgattg gaccgccctt gccgaagaaa tggactttga atacctggaa    180
attagacaac ttgaaacaca ggccgacccc actggcagac tcctggacgc atggcaggga    240
agacctggtg caagcgttgg acggctcctg gatctcctga caaaactggg acgcgacgac    300
gtactgcttg aactcggacc tagcattgaa gaagactgcc aaaaatatat cctgaaacaa    360
caacaagaag aagccgaaaa acctctccaa gtcgcagcag tggactcatc agtaccccga    420
acagctgagc ttgctgggat tactacactc gacgacccac tcggacatat gcctgaaaga    480
ttcgacgctt tcatttgcta ttgcccctct gacata                              516

<210> SEQ ID NO 86
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Glu Glu Ala Glu Lys Pro
            115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 87
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
aagaaagttg caaagaaacc cacaaataaa gccccacacc ctaaacagga accccaagaa      60
atcaatttcc cagatgatct ccctggatct aatactgccg ccccggtcca agaaaccctg     120
catggttgcc agcctgtcac ccaagaggac ggaaaagaat cacggattag cgtacaagag    180
agacaa                                                                186

<210> SEQ ID NO 88
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtcgagtctg gcggtggatc cgga                                             24

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Glu Ser Gly Gly Gly Ser Gly
1               5

<210> SEQ ID NO 91
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
ggcgttcaag tagaaacaat cagcccagga gacggaagga ctttccccaa acgaggccaa      60
acatgcgtag ttcattatac tgggatgctc gaagatggaa aaaagtaga tagtagtaga     120 gaccgaaaca aaccatttaa atttatgttg ggaaaacaag aagtaataag gggctgggaa    180
gaaggtgtag cacaaatgtc tgttggccag cgcgcaaaac tcacaatttc tcctgattat    240
gcttacggag ctaccggcca ccccggcatc ataccccctc atgccacact ggtgtttgac    300
gtcgaattgc tcaaactgga a                                              321

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 93
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 gtcgag                                                                 6

<210> SEQ ID NO 94
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Glu
1

<210> SEQ ID NO 95
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agcctttcaa gttcatgctc ggcaagcagg aggtgatccg ggggtgggag     180
gagggcgtgg ctcagatgtc ggtcgggcaa cgagcgaagc ttaccatctc acccgactac     240
gcgtatgggg caacggggca tccgggaatt atccctcccc acgctacgct cgtattcgat     300
gtggagctct tgaagcttga g                                               321

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tctggcggtg gatccggagt cgac                                             24

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Gly Gly Ser Gly Val Asp
1               5

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cgcgcaaagc gt                                                          12

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Lys Arg
1

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggaaaaccta tacctaatcc attgctgggc ttagactcaa ca                        42

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Lys Pro Ile Pro Asn Pro Leu Leu Gly Leu Asp Ser Thr
1               5                   10

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggcagcggaa gc                                                         12

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ser Gly Ser
1

<210> SEQ ID NO 104
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcaacgaatt tttccctgct gaaacaggca ggggacgtag aggaaaatcc tggtcct        57

<210> SEQ ID NO 105
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Thr Asn Phe Ser Leu Leu Lys Gln Ala Gly Asp Val Glu Glu Asn
1               5                   10                  15

Pro Gly Pro

<210> SEQ ID NO 106
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 acgcgt                                                                    6

<210> SEQ ID NO 107
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Arg
1

<210> SEQ ID NO 108
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atgccccctc ctagactgct gtttttcctg ctctttctca ccccaatgga agttagacct         60
gaggaaccac tggtcgttaa agtggaagaa ggtgataatg ctgtcctcca atgccttaaa        120
gggaccagcg acggaccaac gcagcaactg acttggagcc gggagtcccc tctcaagccg        180
tttctcaagc tgtcacttgg cctgccaggt cttggtattc acatgcgccc ccttgccatt        240
tggctcttca tattcaatgt gtctcaacaa atgggtggat tctacctttg ccagcccggc        300 ccccttctg agaaagcttg gcagcctgga tggaccgtca atgttgaagg ctccggtgag         360
ctgtttagat ggaatgtgag cgaccttggc ggactcggtt gcggactgaa aaataggagc        420
tctgaaggac cctcttctcc ctccggtaag ttgatgtcac ctaagctgta cgtgtgggcc        480
aaggaccgcc ccgaaatctg ggagggcgag cctccatgcc tgccgcctcg cgattcactg        540
aaccagtctc tgtcccagga tctcactatg gcgcccggat ctactctttg gctgtcttgc        600
ggcgttcccc cagatagcgt gtcaagagga cctctgagct ggacccacgt acaccctaag        660
ggccctaaga gcttgttgag cctggaactg aaggacgaca gacccgcacg cgatatgtgg        720
gtaatggaga ccggccttct gctccctcgc gctaccgcac aggatgcagg gaaatactac        780
tgtcatagag ggaatctgac tatgagcttt catctcgaaa ttacagcacg gccgttctt        840 tggcattggc tcctccggac tggaggctgg aaggtgtctg ccgtaacact cgcttacttg        900 atttttgcc tgtgtagcct ggttgggatc ctgcatcttc agcgagccct tgtattgcgc        960
cgaaaaagaa aacgaatgac tgaccctaca cgacgattct ga                         1002

<210> SEQ ID NO 109
<211> LENGTH: 333
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Met Pro Pro Pro Arg Leu Leu Phe Phe Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe
                325                 330
```

<210> SEQ ID NO 110
<211> LENGTH: 107
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 110

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 111
<211> LENGTH: 16
<212> TYPE: PRT
<213> ORGANISM: Homo sapiens

<400> SEQUENCE: 111

Met Gly Ser Asn Lys Ser Lys Pro Lys Asp Ala Ser Gln Arg Arg Arg
1               5                   10                  15

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 112

Met Gly Cys Xaa Cys
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ser Gly Gly Gly Ser
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 114

Ser Gly Gly Gly Ser
1               5

<210> SEQ ID NO 115
<211> LENGTH: 7
<212> TYPE: PRT
<213> ORGANISM: Homo sapiens

<400> SEQUENCE: 115

Thr Asp Pro Thr Arg Arg Phe
1               5
```

METHODS FOR CONTROLLING T CELL PROLIFERATION

RELATED PATENT APPLICATIONS

Priority is claimed to U.S. Provisional Patent Application Ser. No. 61/783,445, filed Mar. 14, 2013, and entitled "Method for Controlling T Cell Proliferation," which is referred to and incorporated by reference herein in its entirety.

FIELD

The technology relates generally to the field of immunology and relates in part to compositions and methods for controlling the proliferation of T cells, for example, therapeutic T cells. The methods further relate to compositions and methods for inducing an immune response in a subject.

SEQUENCE LISTING

The instant application contains a Sequence Listing, which has been submitted electronically in ASCII format and is hereby incorporated by reference in its entirety. Said ASCII copy, created on Jun. 3, 2014, is named BEL-2010-UT_SL.txt and is 52,357 bytes in size.

BACKGROUND

T cell activation is an important step in the protective immunity against pathogenic microorganisms (e.g., viruses, bacteria, and parasites), foreign proteins, and harmful chemicals in the environment. T cells express receptors on their surfaces (i.e., T cell receptors) that recognize antigens presented on the surface of antigen-presenting cells. During a normal immune response, binding of these antigens to the T cell receptor initiates intracellular changes leading to T cell activation.

Chimeric antigen receptors (CARs) are artificial receptors designed to convey antigen specificity to T cells. They include an antigen-specific component, a transmembrane component, and an intracellular component selected to activate the T cell and provide specific immunity. Chimeric antigen receptor-expressing T cells may be used in various therapies, including cancer therapies. While effective against tumors, in some cases these therapies have led to side effects due, in part to non-specific attacks on healthy tissue. A method for controllable T cell therapy is needed that provides a strong immunotherapeutic response and avoids toxic side effects.

SUMMARY

Provided in part are CID-inducible chimeric signaling molecules (CSMs), that may be used, for example, to induce or increase an immune response. The CSMs may be used alone, or in combination with chimeric antigen receptors (CARs), which allows the immune response to be specifically directed against particular tumor cells. The controlled T cell activation methods avoid many of the toxic side effects of earlier CAR-based treatments.

The chimeric signaling molecules discussed herein allow for a sustained, modulated control of a chimeric antigen receptor (CAR) that is co-expressed in the cell. The activation of the antigen-specific T cell, designed to target a cellular antigen implicated in a disease or condition, is dependent on the administration of a ligand inducer. The ligand inducer activates the CAR-expressing cell by multimerizing the chimeric signaling molecule, which, in turn, activates NF-κB signaling, which activates the cell, for example, a T cell, a tumor-infiltrating lymphocyte, a natural killer cell, or a natural killer T cell. (see, for example, FIG. 20) In the absence of the ligand inducer, the T cell is quiescent, or has a basal level of activity. A regular dosing schedule of the ligand determines the rate and magnitude of the CAR-expressing T cell proliferation and activation.

Full activation and tumor cell killing remains dependent on antigen recognition and additional activation of NFAT via CD3 zeta signaling. Once a complete response (CR) is achieved, the dosing of the ligand is ceased. If the disease or condition reoccurs, the ligand dosing is reinitiated, leading to re-expansion and reactivation of quiescent, tumor-target, T cells.

In one example of cell therapy, T cells transduced with a nucleic acid encoding a chimeric antigen receptor have been administered to patients to treat cancer (Zhong, X.-S., (2010) Molecular Therapy 18:413-420). For example, T cells expressing a chimeric antigen receptor based on the humanized monoclonal antibody Trastuzumab (Herceptin) has been used to treat cancer patients. Adverse events are possible, however, and in at least one reported case, the therapy had fatal consequences to the patient (Morgan, R. A., et al., (2010) Molecular Therapy 18:843-851). Transducing the cells with a controllable inducible safety switch, as presented herein, would provide a safety switch that could stop the adverse event from progressing, by stopping the administration of the ligand inducer. Although a low level basal activity might remain, removing the presence of the inducer should drastically reduce, if not cease, the symptoms of the adverse event.

In another example of cell therapy, T cells are modified so that they express a non-functional TGF-beta receptor, rendering them resistant to TGF-beta. This allows the modified T cells to avoid the cytotoxicity caused by TGF-beta, and allows the cells to be used in cellular therapy (Bollard, C. J., et al., (2002) Blood 99:3179-3187; Bollard, C. M., et al., (2004) J. Exptl. Med. 200:1623-1633).

However, it also could result in a T cell lymphoma, or other adverse effect, as the modified T cells now lack part of the normal cellular control; these therapeutic T cells could themselves become malignant. Transducing these modified T cells with an inducible CSM polypeptide-based safety switch as presented herein, would provide a safety switch that could avoid this result.

Thus, featured in some embodiments is a composition, comprising a nucleic acid that comprises a polynucleotide encoding an inducible chimeric signaling molecule, wherein the inducible chimeric signaling molecule comprises a membrane-targeting region, a multimerizing region and a co-stimulatory polypeptide cytoplasmic signaling region selected from the group consisting of CD27, CD28, ICOS, 4-1BB, CD40, RANK/TRANCE-R, CD3 zeta chain, and OX40. In some embodiments, the membrane-targeting region is selected from the group consisting of myristoylation-targeting sequence, palmitoylation-targeting sequence, prenylation sequences (i.e., farnesylation, geranyl-geranylation, CAAX Box), protein-protein interaction motifs and transmembrane sequences (utilizing signal peptides) from receptors. In certain aspects, the membrane-targeting region is a myristoylation targeting sequence. In some embodiments, the inducible chimeric signaling molecule further comprises a second co-stimulatory polypeptide cytoplasmic signaling region selected from the group consisting of CD27, CD28, ICOS, 4-1BB, CD40, RANK/

TRANCE-R, CD3 zeta chain, and OX40. In some embodiments, the co-stimulatory polypeptide cytoplasmic signaling regions comprise a CD28 cytoplasmic signaling region and a 4-1BB cytoplasmic signaling region. In some embodiments, wherein the co-stimulatory polypeptide cytoplasmic signaling regions comprise an OX40 cytoplasmic signaling region polypeptide and a 4-1BB cytoplasmic signaling region polypeptide. In some embodiments, the inducible chimeric signaling molecule further comprises a CD3ζ polypeptide.

In some embodiments, multimerizing region is selected from the group consisting of FKBP, cyclophilin receptor, steroid receptor, tetracycline receptor, heavy chain antibody subunit, light chain antibody subunit, and mutated sequences thereof. In some embodiments, the multimerizing region is an FKBP12 region. In some embodiments, the FKB12 region is an FKB12v36 region. In some embodiments, the multimerizing region is Fv'Fvls. In some embodiments, the multimerizing region binds a ligand selected from the group consisting of an FK506 dimer and a dimeric FK506 analog ligand. In some embodiments, the ligand is AP1903 or AP20187. In some embodiments, the multimerizing region has an amino acid sequence of SEQ ID NO: 58 or a functional fragment thereof. In some embodiments, the multimerizing region is encoded by a nucleotide sequence in SEQ ID NO: 57, or a functional fragment thereof.

In some embodiments, the multimerizing region further comprises a polypeptide having an amino acid sequence of SEQ ID NO: 60, or a functional fragment thereof. In some embodiments, the multimerizing region further comprises a polypeptide encoded by a nucleotide sequence in SEQ ID NO: 59, or a functional fragment thereof. In some embodiments, the multimerizing region further comprises a polypeptide having an amino acid sequence of SEQ ID NO: 60, or a functional fragment thereof. In some embodiments, the multimerizing region further comprises a polypeptide encoded by a nucleotide sequence in SEQ ID NO: 59, or a functional fragment thereof. In some embodiments, the multimerizing region further comprises a polypeptide having an amino acid sequence of SEQ ID NO: 58 or SEQ ID NO: 60, or a functional fragment thereof. In some embodiments, the multimerizing region further comprises a polypeptide encoded by a nucleotide sequence in SEQ ID NO: 57 or SEQ ID NO: 59, or a functional fragment thereof.

In some embodiments, the nucleic acid comprises a promoter sequence operably linked to the polynucleotide. In some embodiments, the nucleic acid is contained within a viral vector. In some embodiments, the viral vector is a retroviral vector. In some embodiments, the retroviral vector is a murine leukemia virus vector. In some embodiments, the murine leukemia virus vector is a MoMLV vector. In some embodiments, the retroviral vector is an SFG vector. In some embodiments, the viral vector is an adenoviral vector. In some embodiments, the viral vector is a lentiviral vector. In some embodiments, the nucleic acid is contained within a plasmid.

Also featured in the present application is a cell transformed or transfected with any of the compositions of the present application. In some embodiments, the cell is a T cell, tumor infiltrating lymphocyte, B cell, NK cell, or NK-T cell. In some embodiments, cell is a T cell. In some embodiments, the cell is obtained or prepared from bone marrow. In some embodiments, the cell is obtained or prepared from umbilical cord blood. In some embodiments, the cell is obtained or prepared from peripheral blood. In some embodiments, the cell is obtained or prepared from peripheral blood mononuclear cells. In some embodiments, the cell is a human cell.

In other embodiments, the cell is further transformed or transduced with a nucleic acid comprising a polynucleotide that encodes a chimeric polypeptide comprising a signal peptide, a single chain variable fragment, a CH2-CH3 hinge region and a CD3ζ polypeptide. In some embodiments, the single chain variable fragment binds to an antigen on a tumor cell. In some embodiments, the single chain variable fragment binds to an antigen on a cell involved in a hyperproliferative disease. In some embodiments, the single chain variable fragment is selected from the group consisting of αPSMA, αPSCA, αMUC1, αCD19, αROR1, αMesothelin, αGD2, αCD123, αMUC16, and αHer2/Neu single chain variable fragments. In some embodiments, the single chain variable fragment is an αCD19 single chain variable fragment.

Also provided are methods for inducing an immune response, comprising transfecting or transducing a cell in vitro or ex vivo with a composition of the present application. In some embodiments, the method further comprises contacting the cell with a ligand that binds to the multimerizing region resulting in multimerization of the inducible chimeric signaling molecule. In some embodiments, the ligand is dimeric. In some embodiments, the ligand is dimeric FK506, or a dimeric FK506-like analog. In some embodiments, the ligand is AP1903 or AP20187. In some embodiments, the method further comprises administering the transfected or transformed cell to a subject. In some embodiments, the cell is administered to the subject by intravenous administration. In some embodiments, a method is provided for inducing an immune response in vivo, comprising administering to a subject a composition of the present application. In some embodiments, the methods further comprise administering to the subject a composition comprising a ligand that binds to the multimerizing region resulting in multimerization of the inducible chimeric signaling molecule. In some embodiments, the ligand is dimeric. In some embodiments, the ligand is dimeric FK506, or a dimeric FK506-like analog. In some embodiments, the ligand is AP1903 or AP20187.

In some embodiments, the subject treated with the composition or cell of the present application has been diagnosed with a hyperproliferative disease. In other embodiments, wherein the subject has been diagnosed with a tumor. In other embodiments, the subject has cancer. In other embodiments, the subject has a solid tumor. IN other embodiments, the cell is a tumor infiltrating lymphocyte or a T cell. In other embodiments, the cell is delivered to the tumor bed. In other embodiments, the cancer is present in the blood or bone marrow of the subject. In other embodiments, the subject has a blood or bone marrow disease. In other embodiments, the subject has been diagnosed with any condition or disorder that can be alleviated by stem cell transplantation. In other embodiments, the subject has been diagnosed with sickle cell anemia or metachromatic leukodystrophy. In other embodiments, the subject has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder. In other embodiments, the subject has been diagnosed with a condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis. In some embodiments, the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

Also provided is a method for treating leukemia in a subject, comprising administering a cell of the present application, wherein the cell is transduced or transfected with an inducible CSM and a chimeric antigen receptor comprising a single chain variable fragment, and administering a multimeric ligand to the subject. In some embodiments, the single chain variable fragment binds to CD19. In some embodiments, the multimeric ligand is AP1903 or AP20187. In some embodiments, the cell is a T cell.

In some embodiments, the subject is human. In some embodiments, the methods further comprise determining whether an additional dose of the multimeric ligand should be administered to the subject. In some embodiments, the methods further comprise administering an additional dose of the multimeric ligand to the subject, wherein the disease or condition symptoms remain or are detected following a reduction in symptoms. In some embodiments, the subject has been diagnosed with a disease or condition before administration of the composition or cell of the present application, and after administration of the multimeric ligand the disease or condition is detected, an additional dose of the multimeric ligand is administered to the subject.

In some embodiments, the methods further comprise identifying the presence, absence or stage of a condition or disease in a subject, and transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

In some embodiments, the condition is cancer. In some embodiments, the condition is leukemia. In some embodiments, the condition is a solid tumor.

In other embodiments, the methods further comprise determining the presence or absence of a tumor size increase and/or increase in the number of tumor cells in a subject relative to the tumor size and/or the number of tumor cells following administration of the multimeric ligand, and administering an additional dose of the multimeric ligand to the subject in the event the presence of a tumor size increase and/or increase in the number of tumor cells is determined. In some embodiments, the tumor size and/or the number of tumor cells is decreased following administration of the multimeric ligand relative to the tumor size and/or number of tumor cells before administration of the multimeric ligand.

In some embodiments, the methods further comprise determining the presence or absence of an increase in CD19-expressing B cells in the subject relative to the level of CD19-expressing B cells following administration of the multimeric ligand, and administering an additional dose of the multimeric ligand to the subject in the event the presence of an increase in CD19-expressing B cells in the subject is determined. In some embodiments, the level of CD19-expressing B cells is decreased following administration of the multimeric ligand relative to the level of CD19-expressing B cells before administration of the multimeric ligand.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

In general, T cell therapy has involved the difficulty of poor in vivo expansion of the infused cells. One way this issue has been addressed is by administering high doses of IL-2 to the patient. This therapy helps T cell growth and anti-tumor function, but is also very toxic to the patient. This has generally been used in melanoma as high dose IL-2 is considered a standard-of-care therapy for that disease. Most other T cell therapy applications have not used IL-2 with T cell therapy due to toxic effects. Another issue arising in T cell therapy is the poor engraftment and persistence of infused T cells (also a function of in vivo proliferation), which has been addressed by lymphodepleting conditioning prior to T cell infusion. Investigators generally use chemotherapy (cyclophosphamide in particular) to achieve this, although some use antibodies including Campath. Conditioning appears to greatly facilitate T cell therapy through creating lymphoid "space" and depleting regulatory immune cells that compete for growth and survival factors. However, it is very toxic to the patient, completely ablates normal immune cells (e.g. pathogen-specific) and cannot be readily used for some types of cancer or older patients. In addition, use of a lymphodepleting regimen might push a T cell therapy toward a "procedure" rather than a standalone therapeutic.

T cell therapy has largely been considered a boutique therapy since each patient needs to have a unique cell product manufactured for them. Conventional T cell therapies (generated by repetitive antigen stimulation or isolation of tumor infiltrating lymphocytes (TILs)) are not reproducible in their specificity or function and lead to extremely variable results, and in some cases the inability to produce a product for treatment. Gene transfer of natural or chimeric T cell receptors has started to solve this problem (where highly tumor specific T cells can be generated in less than 2 weeks), but it is apparent that gene-modified T cells can function differently than naturally occurring T cells. In addition, highly specific CAR T cells or T cells expressing optimized TCR alpha and beta chains can cause off-target toxicity, necessitating the inclusion of a suicide gene.

Figure 1:
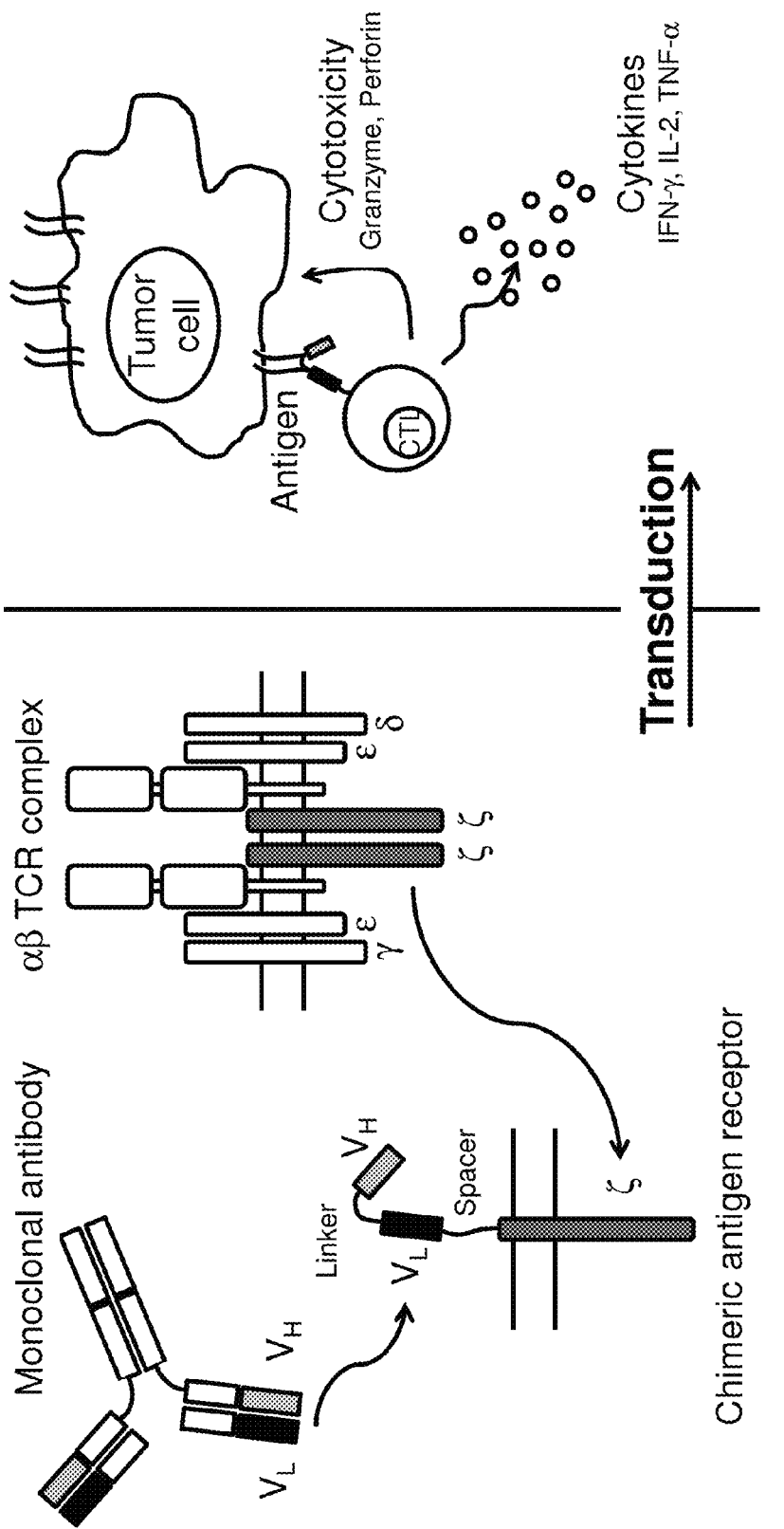
FIG. 1 provides an illustration of gene transfer of chimeric antigen receptors (CARs).

FIG. 1 illustrates the most basic components of a chimeric antigen receptor (CAR). The variable heavy ($V_H$) and light ($V_L$) chains for a tumor-specific monoclonal antibody are fused in-frame with the CD3 zeta chain ($\zeta$) from the T cell receptor complex. The $V_H$ and $V_L$ are generally connected together using a flexible glycine-serine linker, and then attached to the transmembrane domain by a spacer (CH2CH3) to extend the scFv away from the cell surface so that it can interact with tumor antigens.

Following transduction, T cells now express the CAR on their surface, and upon contact and ligation with a tumor antigen, signal through the CD3 zeta chain inducing cytotoxicity and cellular activation.

Figure 2:
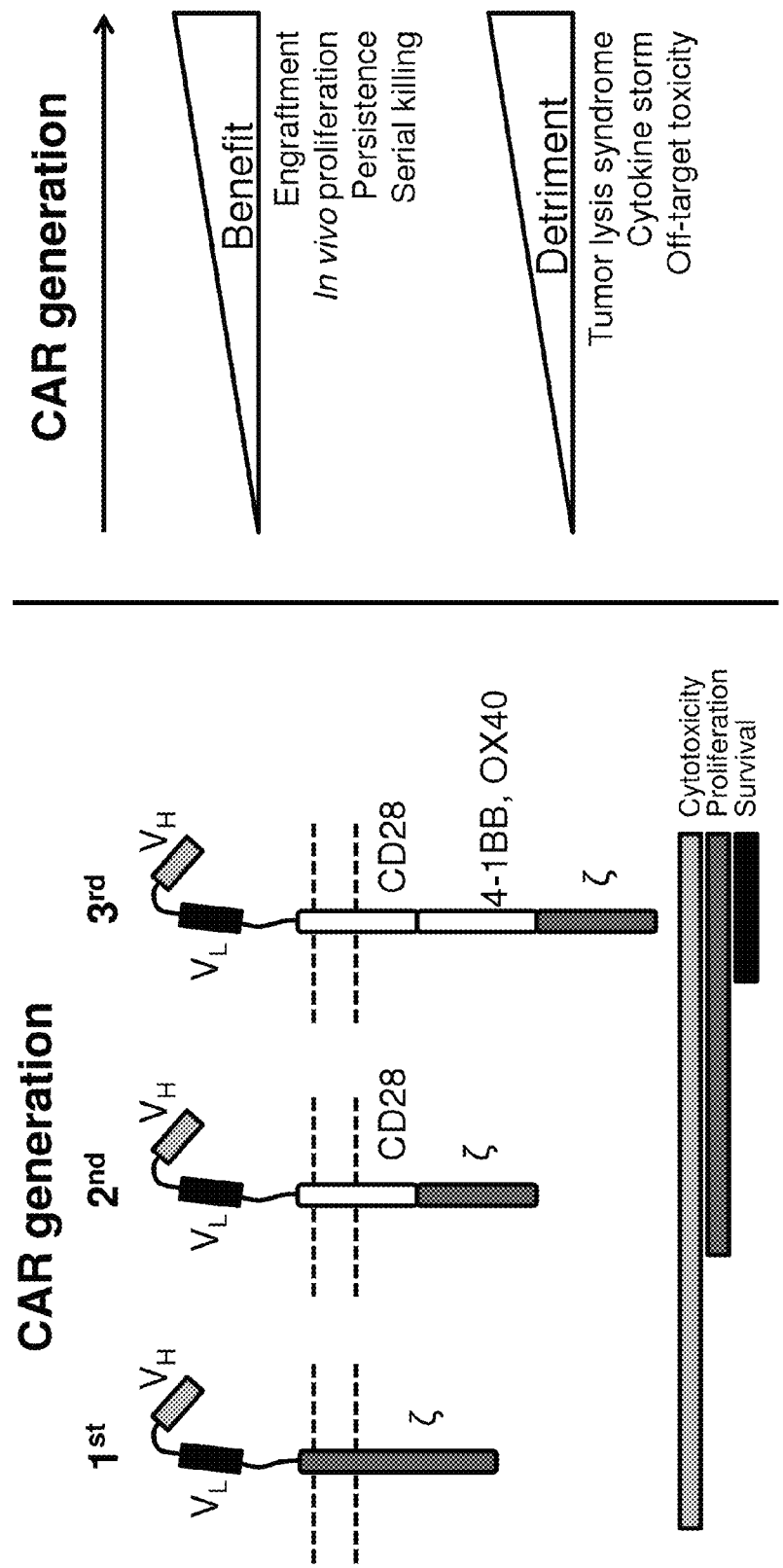
FIG. 2 provides an illustration of CAR improvements and associated toxicity.

FIG. 2 illustrates the development of various chimeric antigen receptors. Investigators have noted that activation of T cells through CD3 zeta is sufficient to induce a tumor-specific killing, but is insufficient to induce T cell proliferation and survival. Early clinical trials using T cells modified with CARs expressing only the zeta chain showed that gene-modified T cells exhibited poor survival and proliferation in vivo. These constructs are termed $1^{st}$ generation CARs.

As co-stimulation through the B7 axis is necessary for complete T cell activation, investigators added the co-stimulatory polypeptide CD28 signaling domain to the CAR construct. This region generally contains the transmembrane region (in place of the CD3 zeta version) and the YMNM motif for binding PI3K and Lck. In vivo comparisons between T cells expressing CARs with only zeta or CARs with both zeta and CD28 demonstrated that CD28 enhanced expansion in vivo, in part due to increased IL-2 production following activation. The inclusion of CD28 is called a $2^{nd}$ generation CAR.

The use of co-stimulatory polypeptides 4-1BB or OX40 in CAR design has further improved T cell survival and efficacy. 4-1BB in particular appears to greatly enhance T cell proliferation and survival. This $3^{rd}$ generation design (with 3 signaling domains) has been used in PSMA CARs (Zhong X S, et al., Mol Ther. 2010 February; 18(2):413-20), and in CD19 CARs, most notably for the treatment of CLL (Milone, M. C., et al., (2009) Mol. Ther. 17:1453-1464; Kalos, M., et al., Sci. Transl. Med. (2011) 3:95ra73; Porter, D., et al., (2011) N. Engl. J. Med. 365: 725-533). These cells showed impressive function in 3 patients, expanding more than a 1000-fold in vivo, and resulted in sustained remission in all three patients.

However, as CARs have improved in their anti-tumor effects, they have also become more dangerous. There have been two high-profile deaths using $2^{nd}$ and $3^{rd}$ generation CARs, which is high considering only a handful of patients have been treated. These deaths resulted from sepsis due to cytokine storm and tumor lysis syndrome caused by highly activated T cells (Morgan, R. A., et al. (2010) Mol. Ther. 14:843-851).

A suicide gene provides ample protection against unwanted side-effects from adoptively transferred T cells; however, elimination of gene-modified T cells following toxicity may also ablate the therapeutic efficacy of the treatment.

T cell receptor signaling can be induced using a chemical inducer of dimerization (CID) in combination with a chimeric receptor that includes a multimerization region that binds to the CID, T cells were engineered to express the CD3 zeta chain, which was linked with 1, 2, or 3 FKBP fragments. The cells expressed the chimeric receptor, and demonstrated CID-dependent T cell activation (Spencer, D. M., et al., Science, 1993. 262: p. 1019-1024). The present application provides, in part, inducible chimeric signaling molecules (CSMs) that are controlled by CID. Contacting T cells that express the inducible CSMs with a CID results in cell activation, and induction of an immune response.

Figure 3:
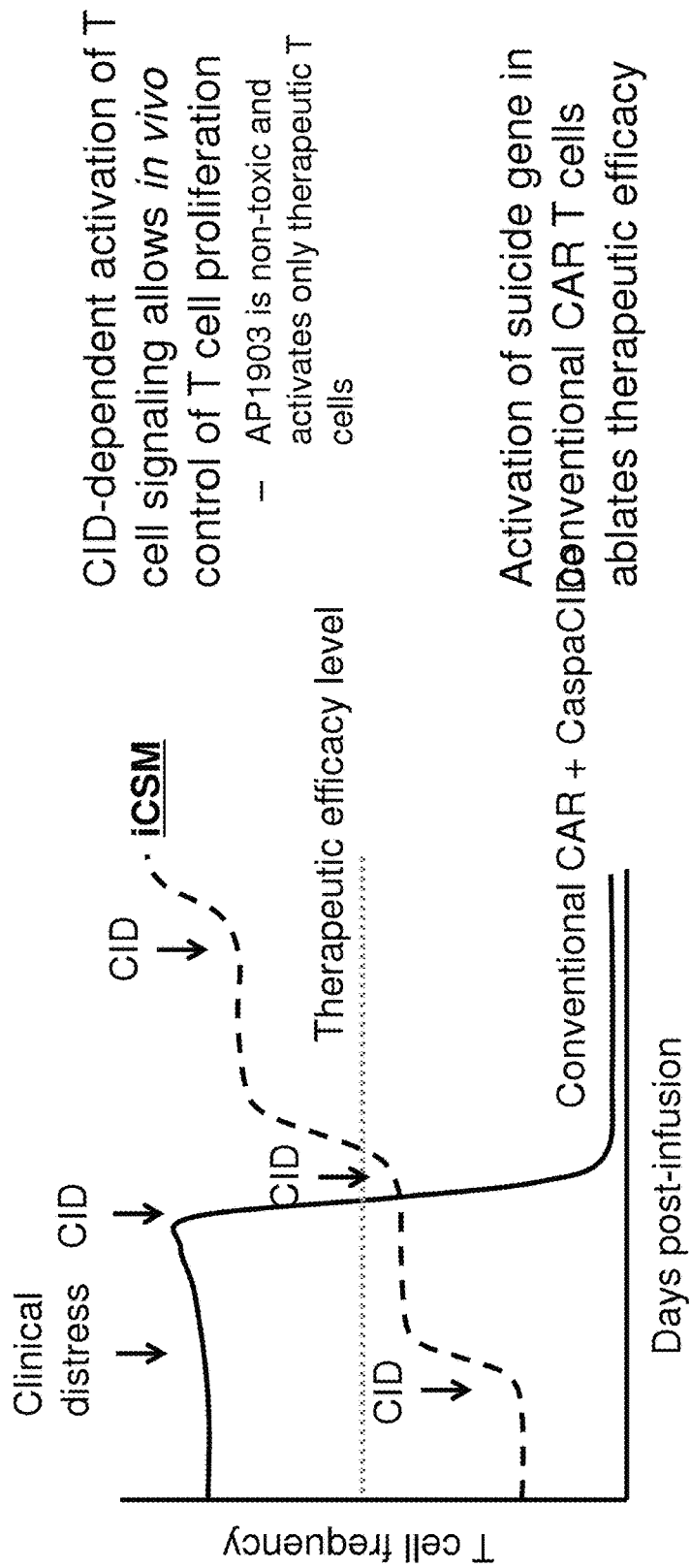
FIG. 3 provides a graphical depiction of a theoretical analysis of a CID-controlled chimeric signaling molecule compared to CAR-expressing cells that also express a suicide (apoptosis) gene.

FIG. 3 compares the therapies of the present application with methods of CAR treatment using a suicide gene. The present application provides, in part, a gene-engineering approach to amplify T cell proliferation and function in vivo so that the anti-tumor effect is gradually increased. A chemical inducer of dimerization is used in a controllable system for activating T cells in vivo to increase their function and frequency.

Figure 4:
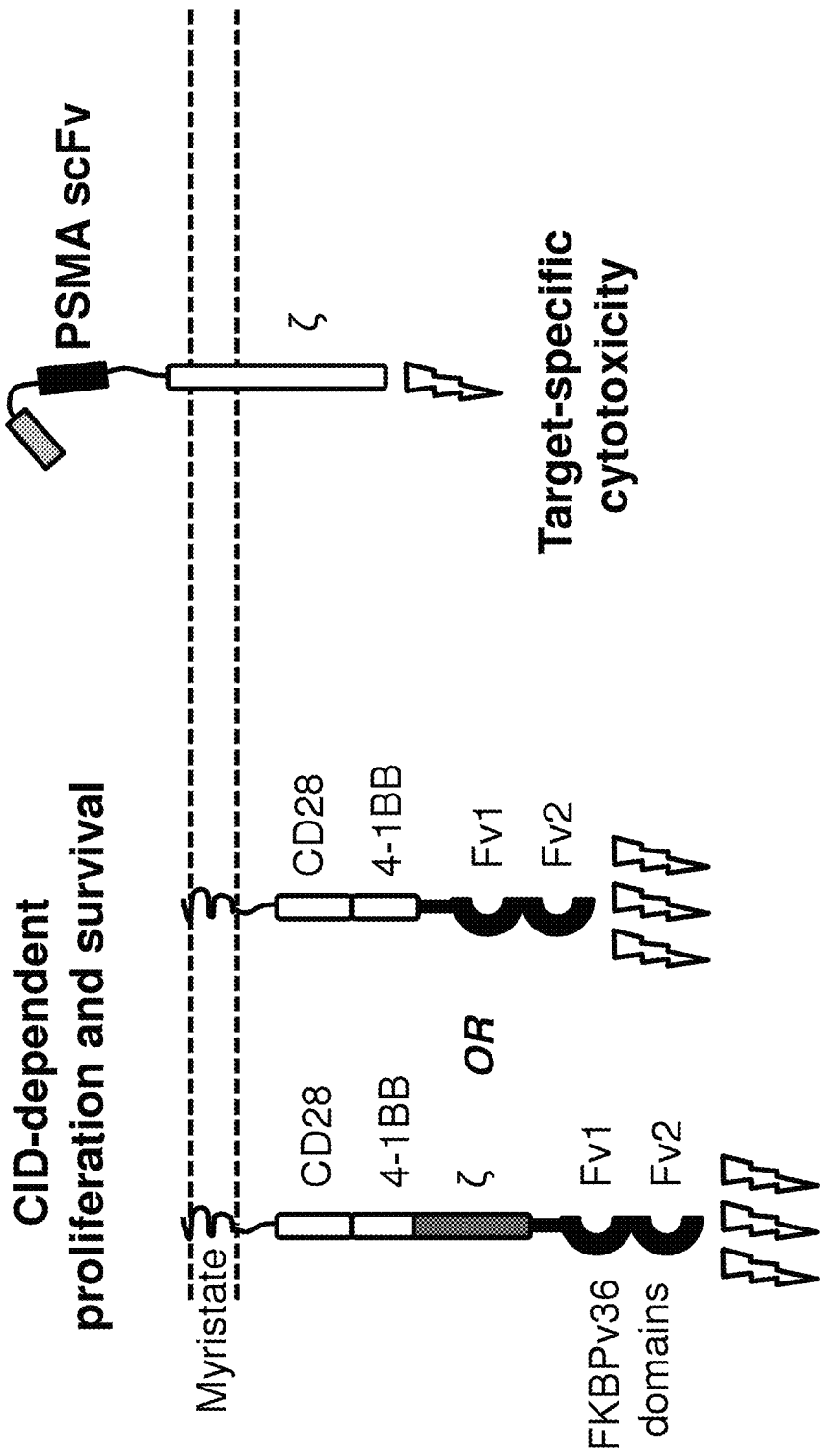
FIG. 4 provides an illustration of some examples of CID-controlled CSMs.
Figure 5:
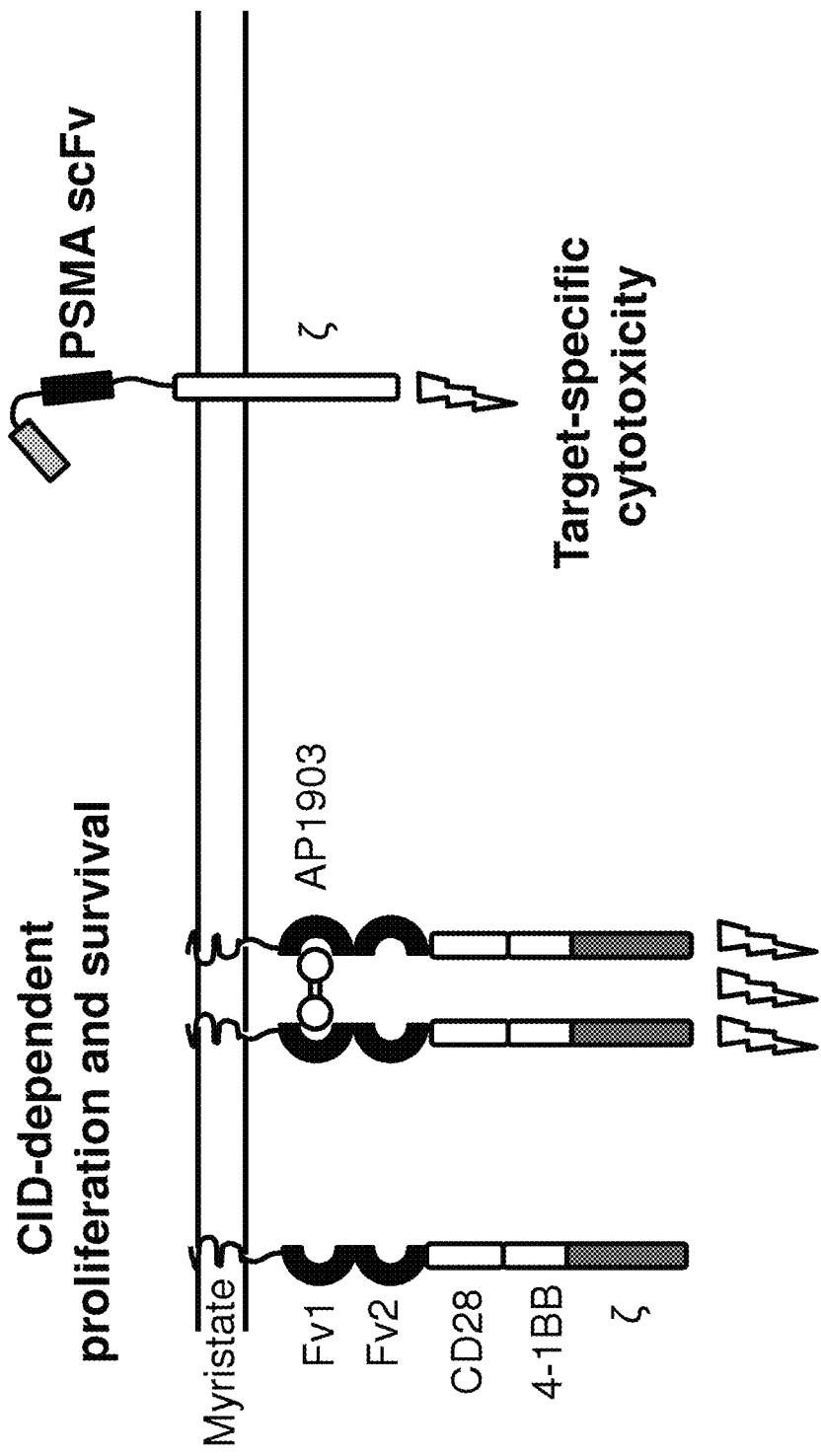
FIG. 5 provides an illustration of CID-induction of a CSM, and inducible CSM activation of a T cell comprising a CAR.

As shown in FIGS. 4 and 5, in some embodiments the CSM uses a multimerization region, such as Fv domains, in tandem with one or more co-stimulatory polypeptides, such as, for example, CD28 and 4-1BB, with and without the CD3 zeta chain to enable CID-dependent proliferation and co-stimulation. The CSM may be used alone to provide co-stimulation, and increase a T cell immune response. Using this method, a population of T cells, for example a population with non-specific targets, may be transfected or transformed with DNA coding for CSM, then administered to a subject to enhance a general immune response.

Figure 6:
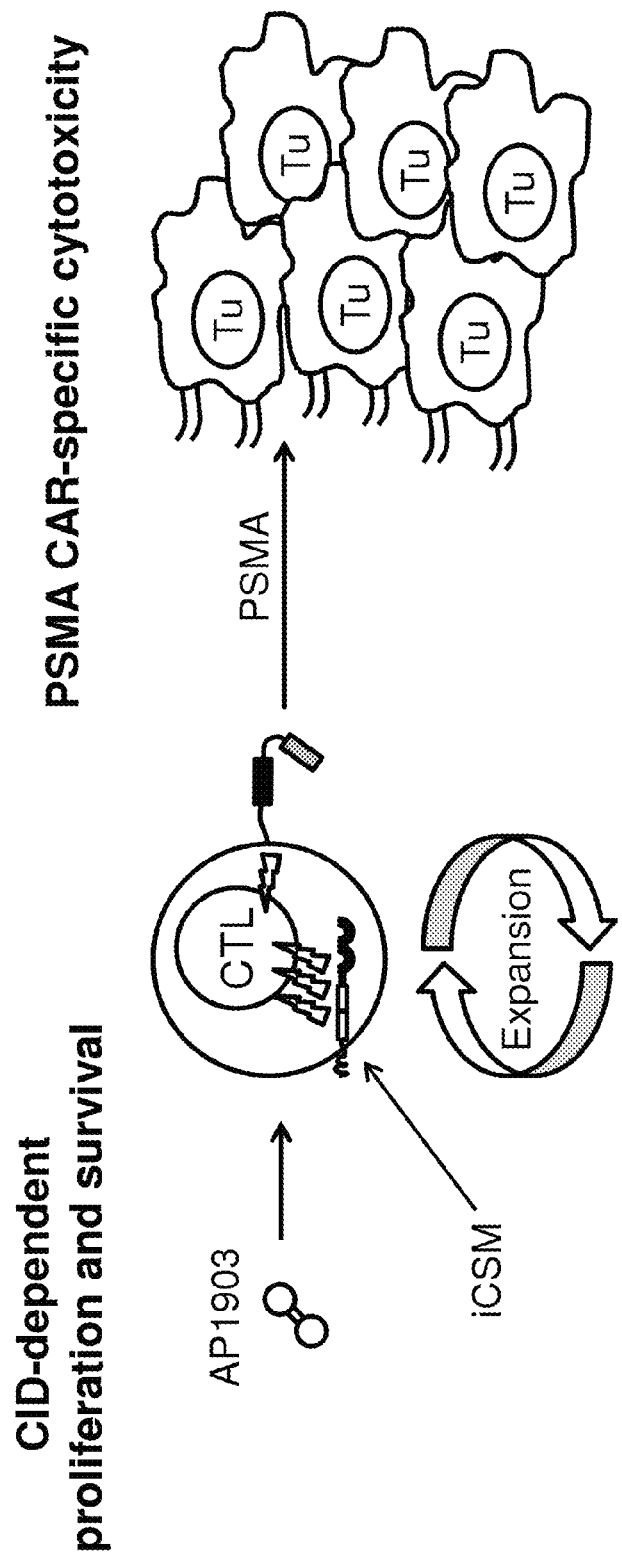
FIG. 6 provides an illustration of CID-controlled T cell killing of tumor cells.
Figure 7:
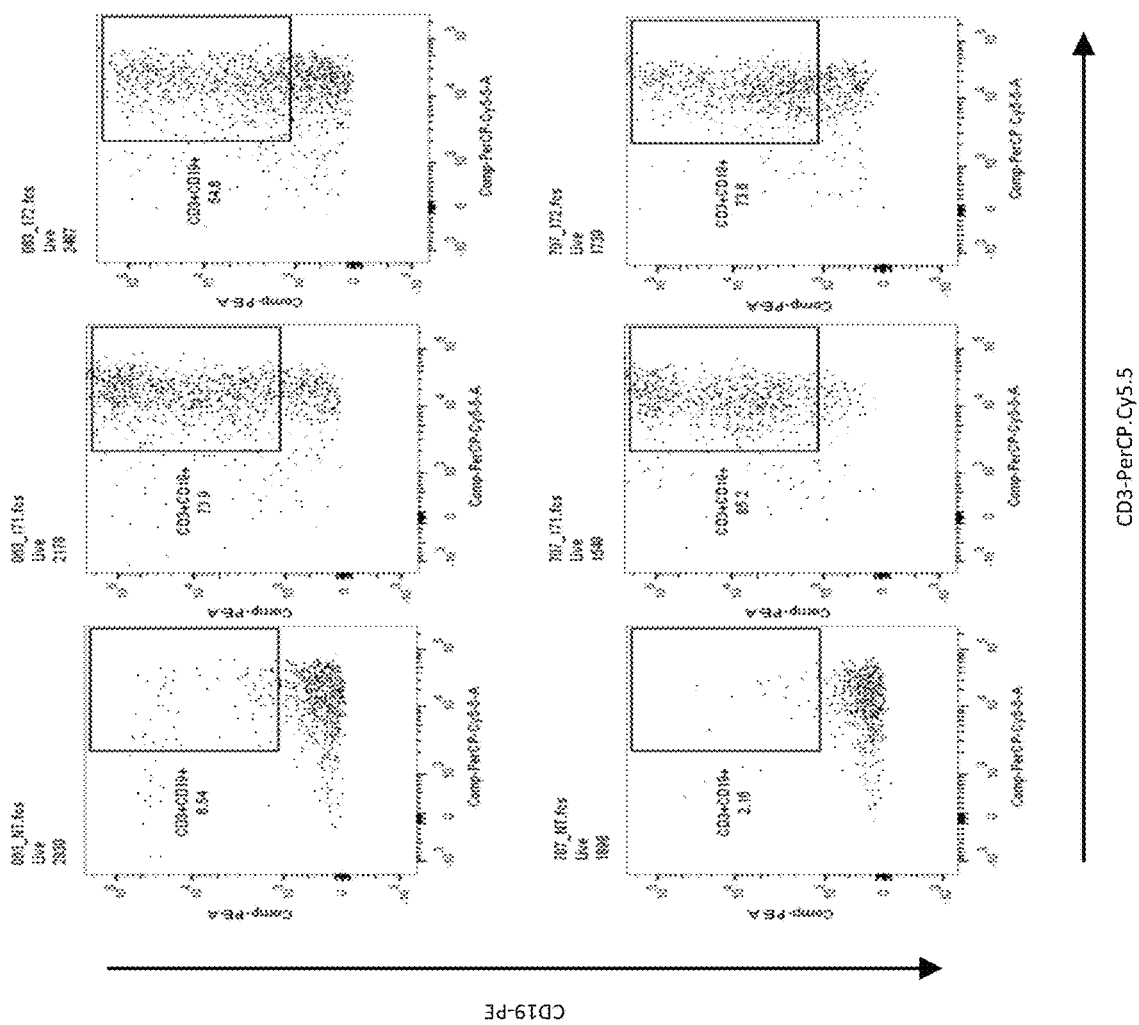
FIG. 7 provides the results of FACs sorting analysis of modified T cells.
Figure 8:
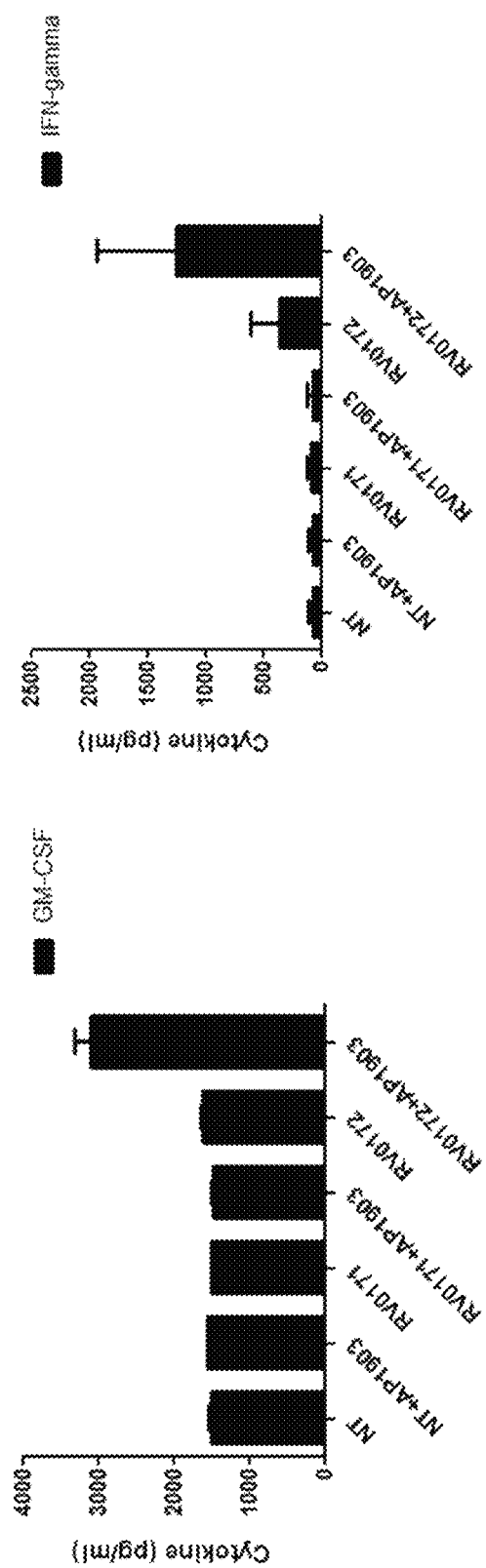
FIG. 8 provides bar graphs of GM-CSF and Interferon gamma levels in the modified and control T cells.
Figure 9:
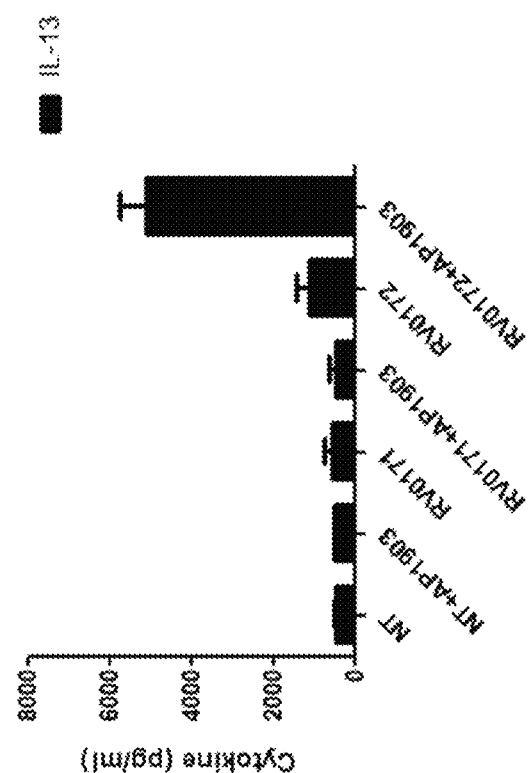
FIG. 9 provides bar graphs of IL-10 and IL-13 levels in the modified and control T cells.
Figure 9:
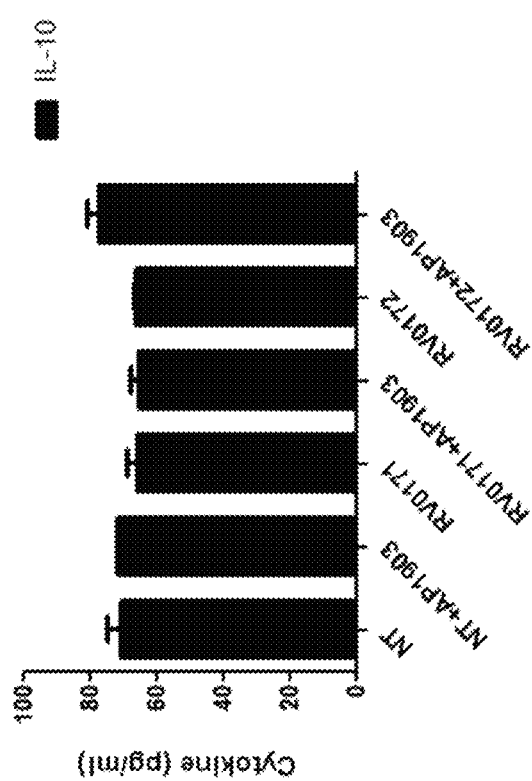
Figure 10:
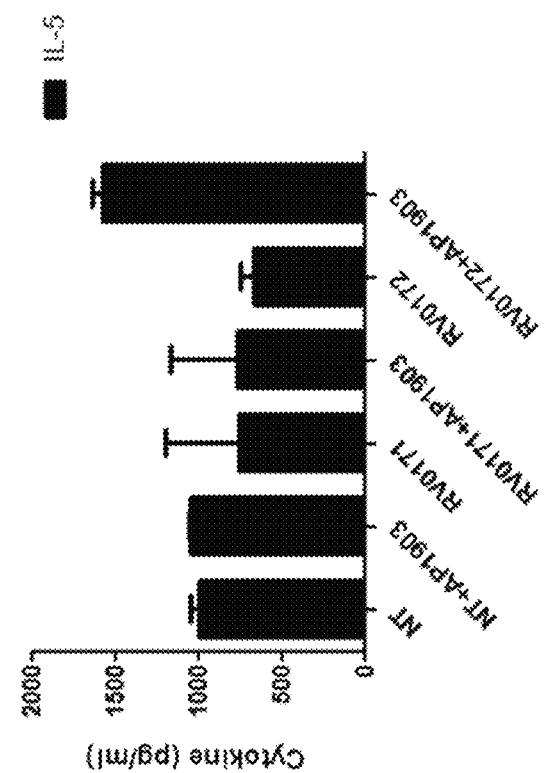
FIG. 10 provides bar graphs of IL-4 and IL-5 levels in the modified and control T cells.
Figure 10:
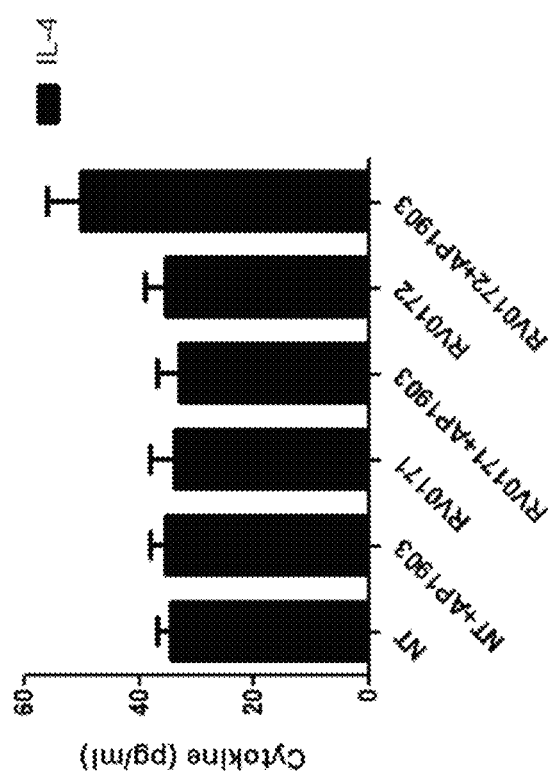
Figure 11:
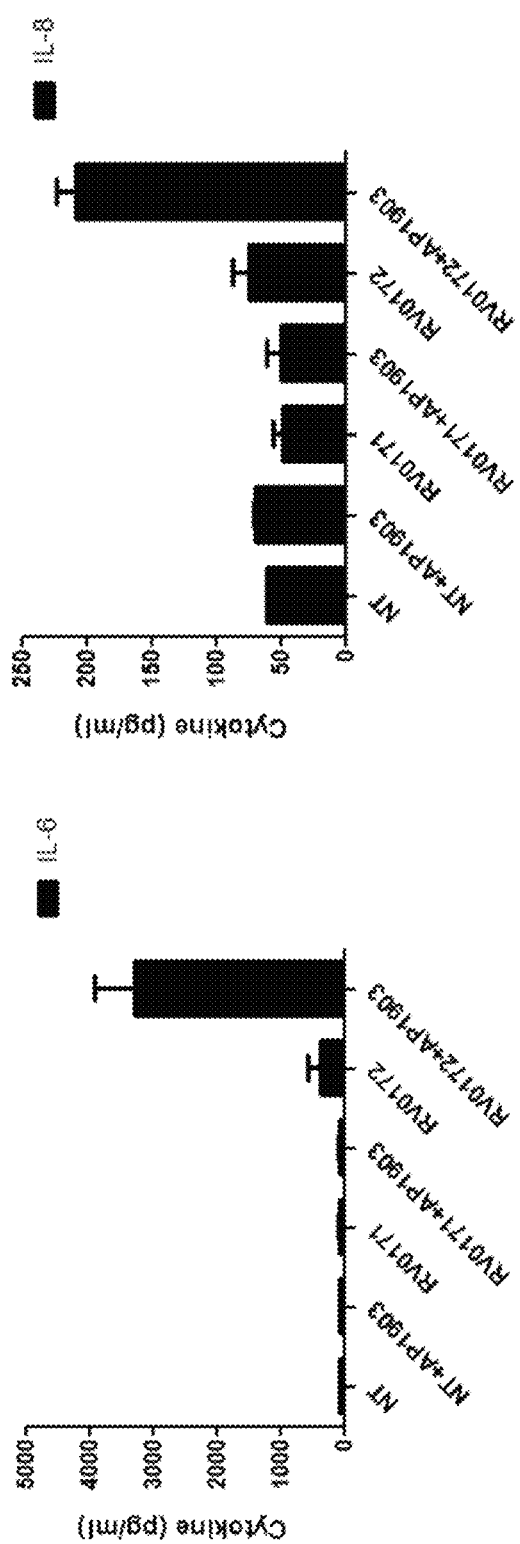
FIG. 11 provides bar graphs of IL-6 and IL-8 levels in the modified and control T cells.
Figure 12:
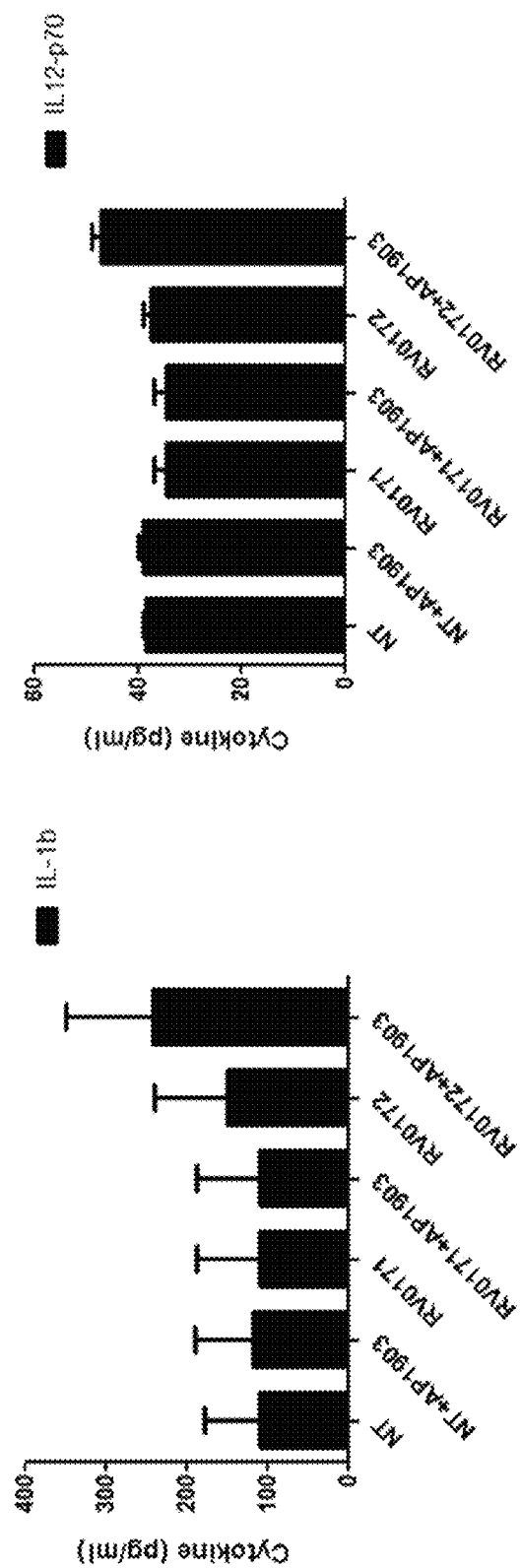
FIG. 12 provides bar graphs of IL-1β and IL-12-p70 levels in the modified and control T cells.
Figure 13:
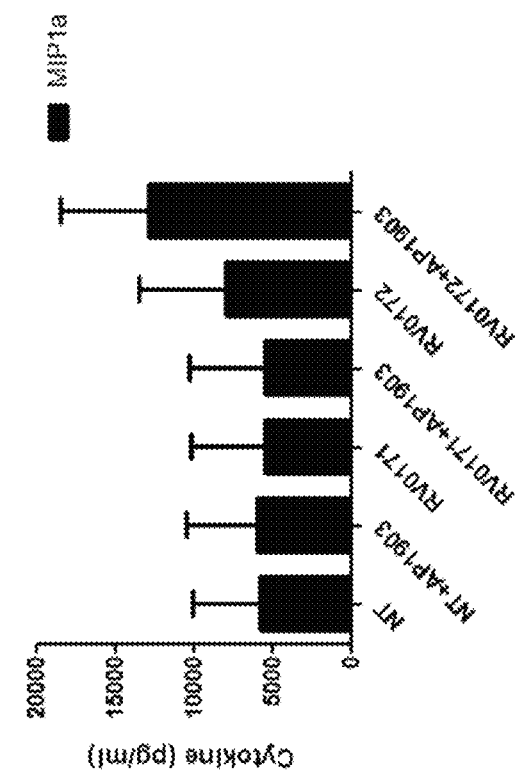
FIG. 13 provides bar graphs of IP-10 and MIP1α levels in the modified and control T cells.
Figure 13:
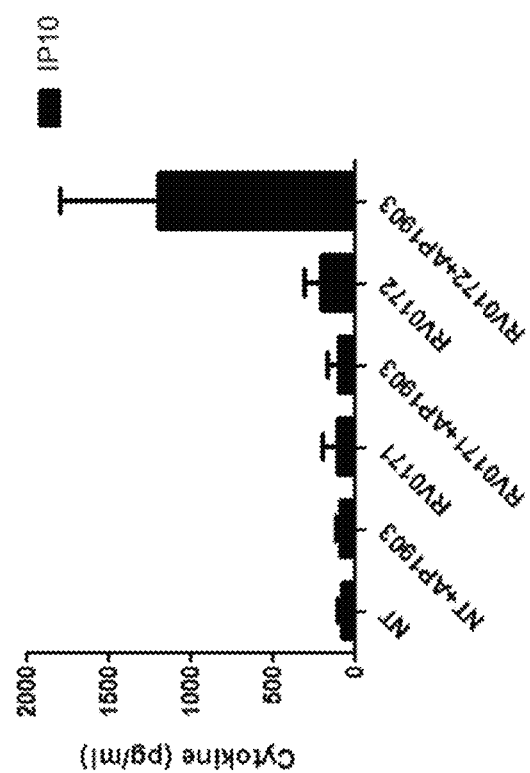
Figure 14:
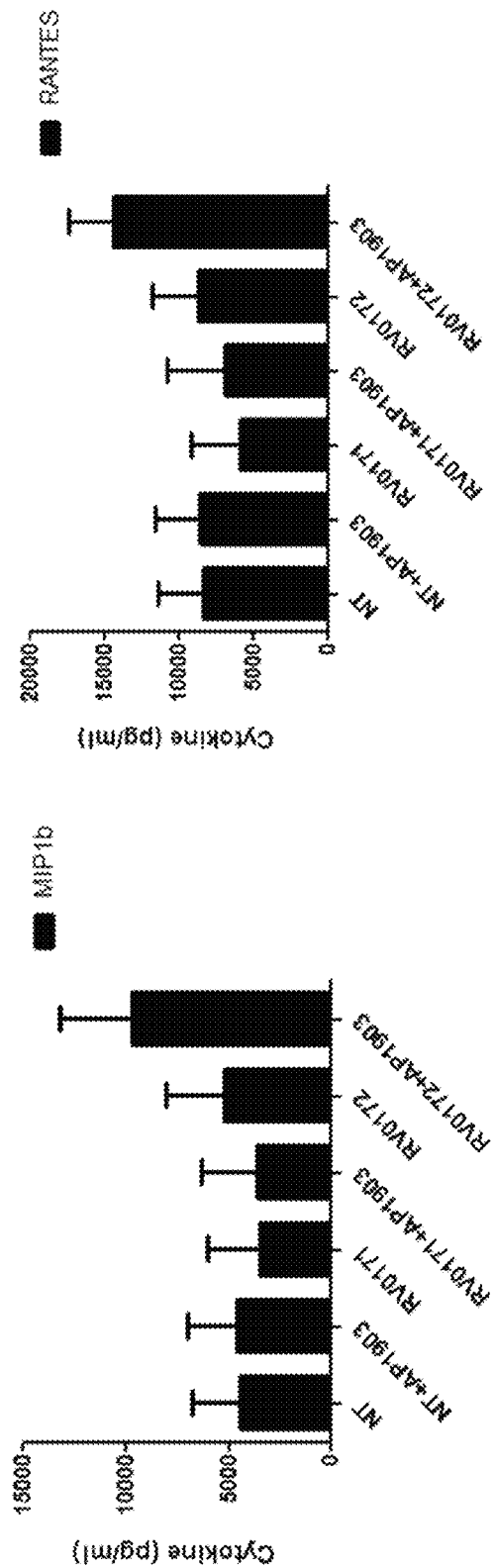
FIG. 14 provides bar graphs of MIP1β and RANTES levels in the modified and control T cells.
Figure 15:
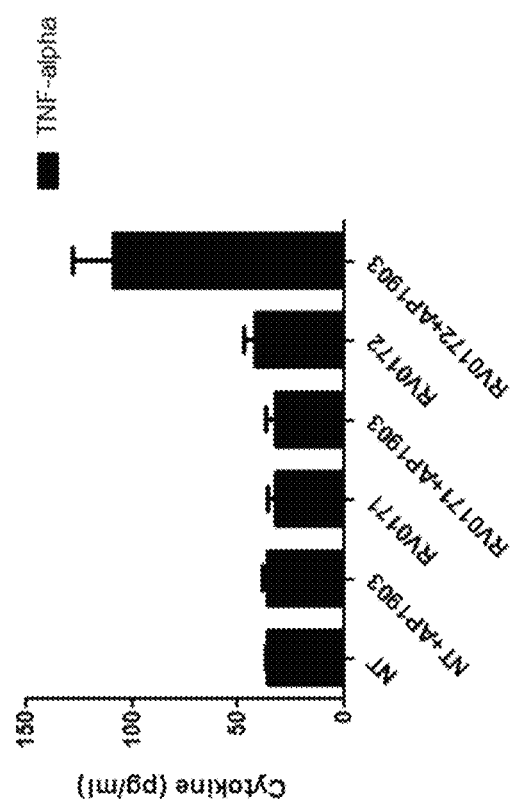
FIG. 15 provides a bar graph TNF-α levels in the modified and control T cells.
Figure 16:
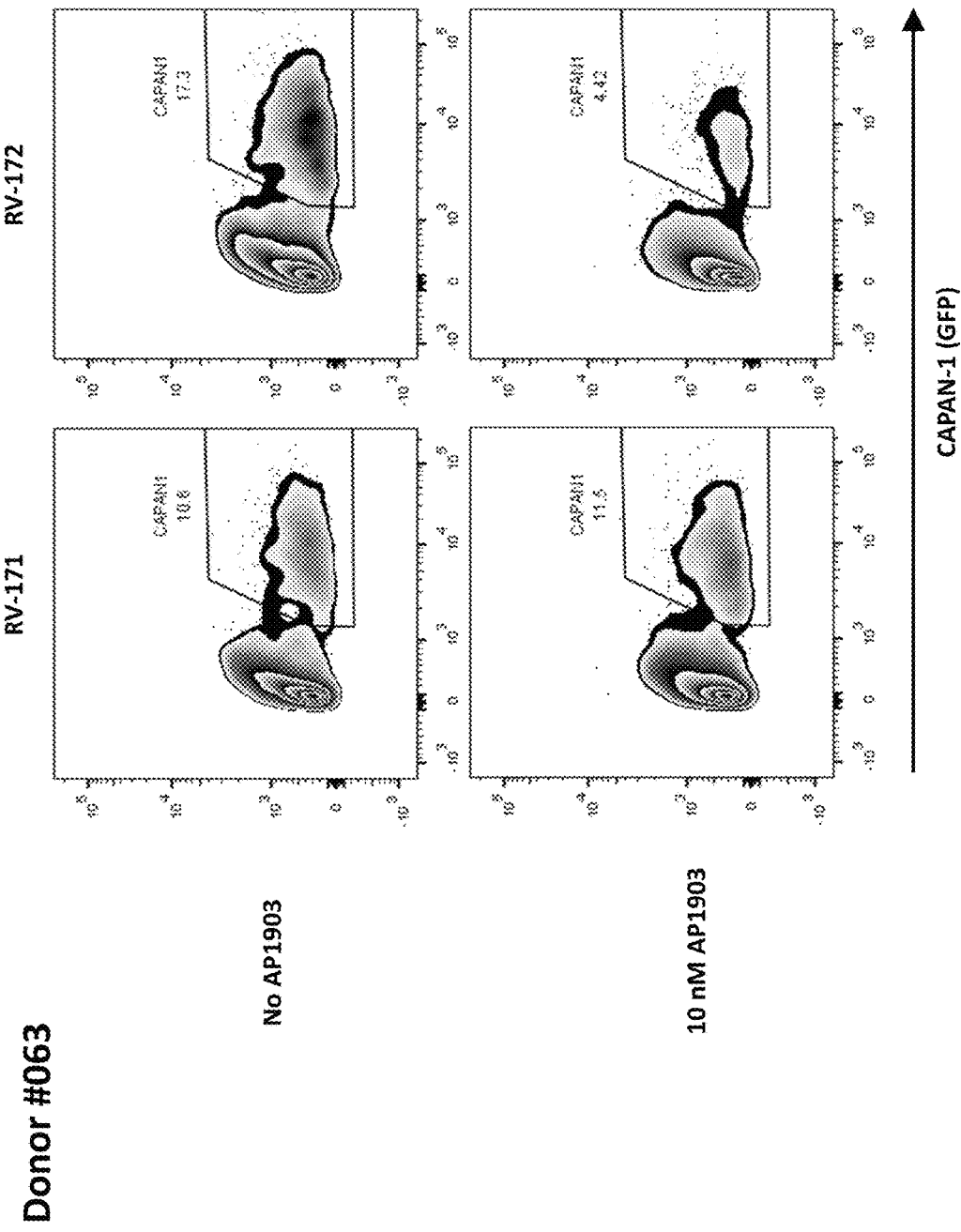
FIG. 16: Activation of iMC-transduced T cells with AP1903 induces T cell killing of tumor cells. T cells transduced with a control vector (lacking MyD88/CD40 signaling domains) or with iMC were cultured with CAPAN-1-GFP tumor cells at a ratio of 5:1 T cells to tumor cells. Co-cultures were cultured with or without 10 nM AP1903. After 72 hours, co-cultures were analyzed for GFP$^+$ tumor cells (X-axis) by flow cytometry.
Figure 17:
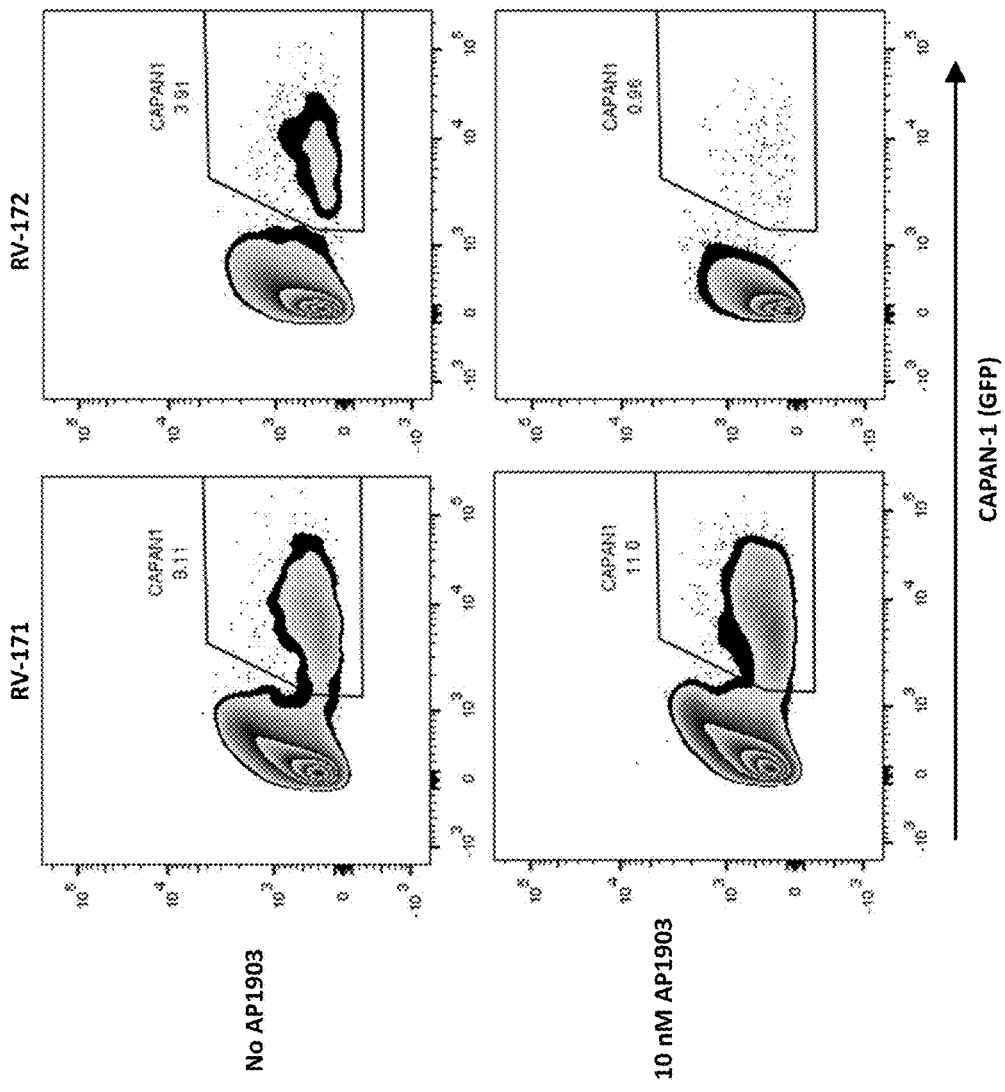
FIG. 17 depicts the results of a similar experiment to that discussed for FIG. 16, for a different donor.
Figure 18:
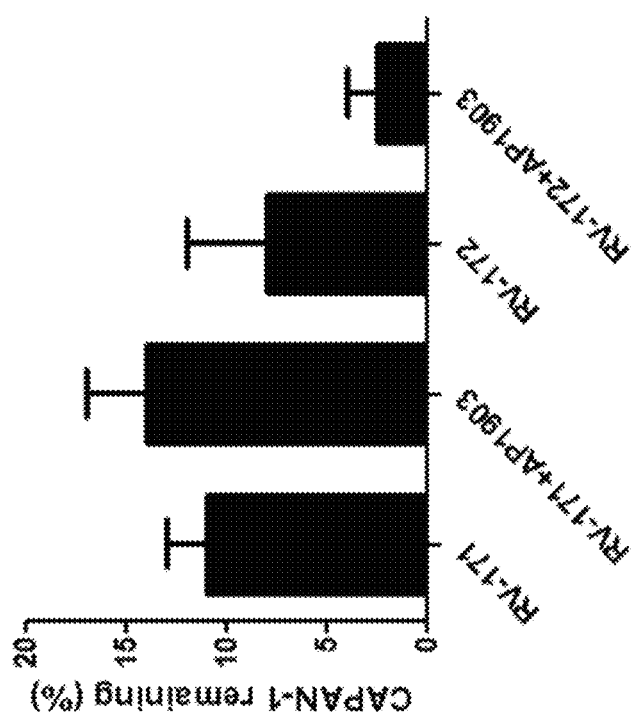
FIG. 18: Activation of iMC-transduced T cells with AP1903 induces T cell killing of tumor cells. T cells transduced with a control vector (lacking MyD88/CD40 signaling domains) or with iMC were cultured with CAPAN-1-GFP tumor cells at a ratio of 5:1 T cells to tumor cells. Co-cultures were cultured with or without 10 nM AP1903. After 72 hours, co-cultures were analyzed for GFP+ tumor cells by flow cytometry (n=2).
Figure 19:
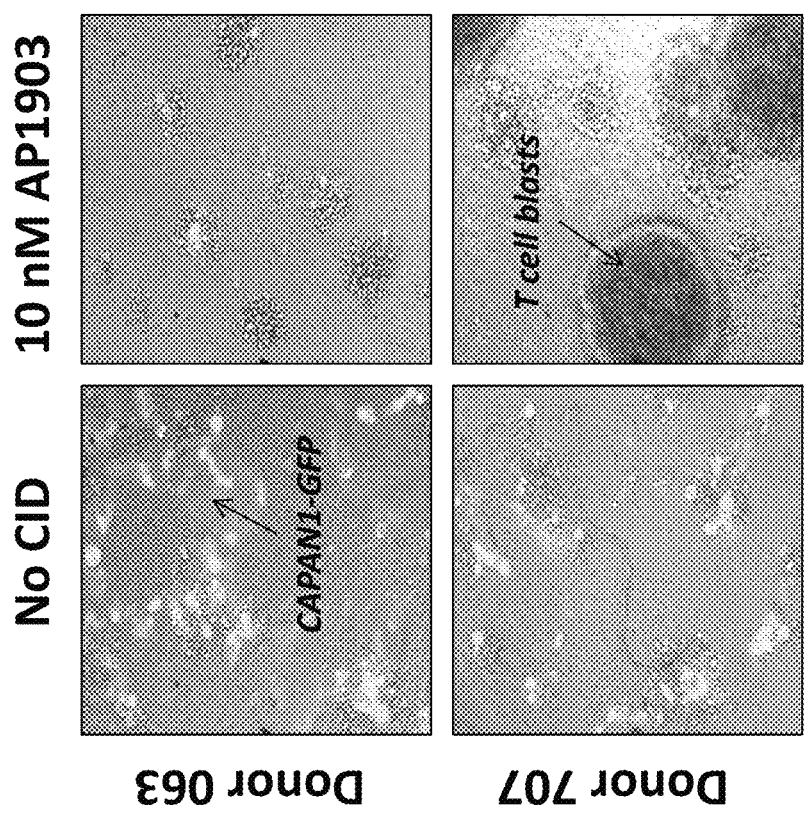
FIG. 19: Activation of iMC-transduced T cells with AP1903 induces T cell killing of tumor cells. T cells transduced with a control vector (lacking MyD88/CD40 signaling domains) or with iMC were cultured with CAPAN-1-GFP tumor cells at a ratio of 5:1 T cells to tumor cells. Co-cultures were cultured with or without 10 nM AP1903. After 72 hours, co-cultures were analyzed by fluorescent microscopy, showing the activation of T cell blasts (right two panels) and the elimination of GFP+ tumor cells when activated with 10 nM AP1903.
Figure 20:
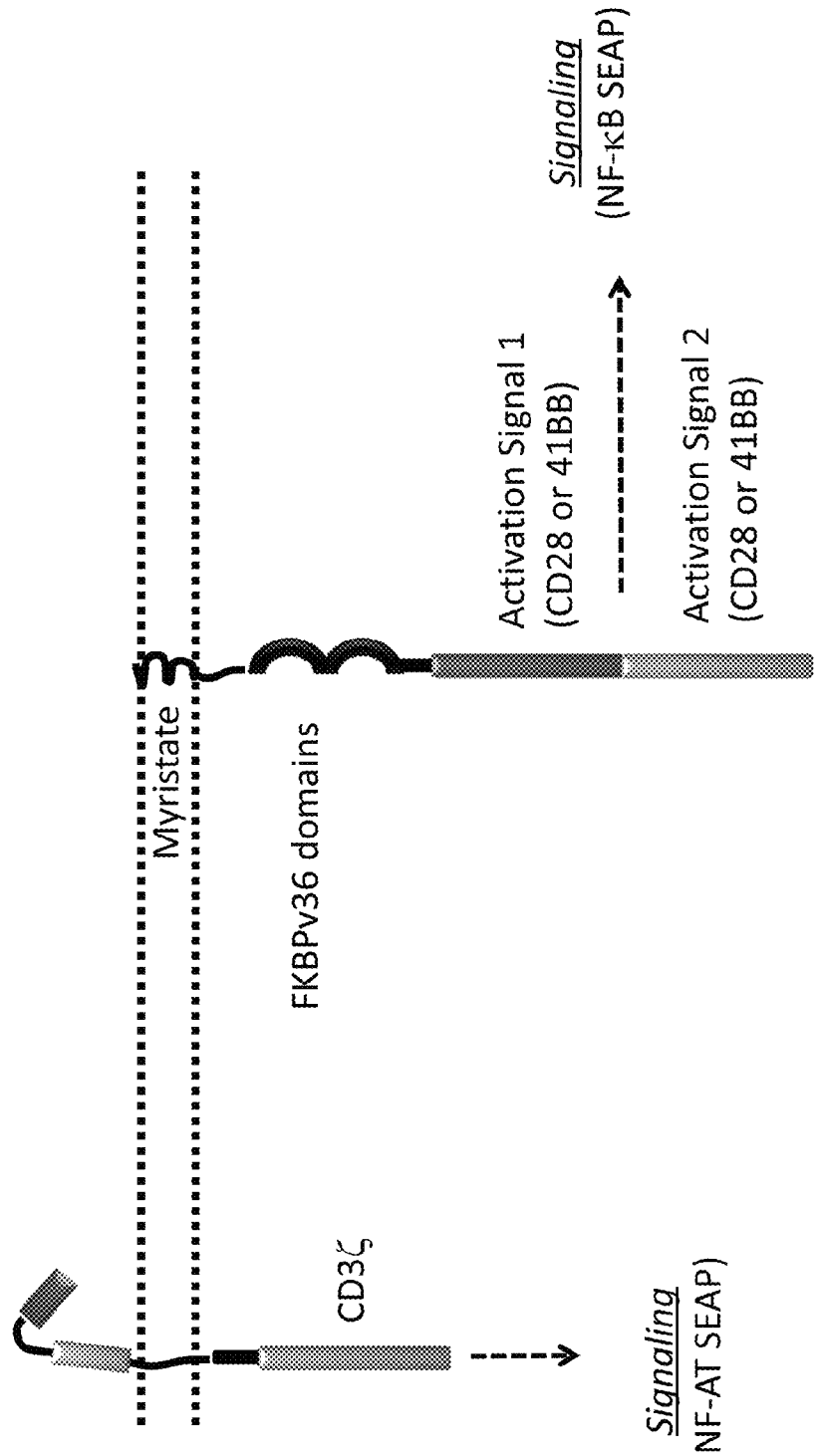
FIG. 20 is a schematic of a cell transduced or transfected with a chimeric antigen receptor (left) and an example of a chimeric signaling molecule as provided herein.

This CSM may also be expressed in a cell along with a CAR, which may, for example, comprise the scFv polypeptide, and the CD3 zeta chain. In this method, an inducible CSM molecule is used in combination with a CAR, thereby segregating CAR signaling into two separate functions. This second function, provided by the CAR, provides antigen-specific cytotoxicity to the engineered T cells. In FIG. 4, the example shows a CAR with specificity against PSMA; these engineered T cells may, for example, be administered to a subject to generate a specific immune response, for example one directed against a prostate cancer tumor (FIG. 6).

Figure 22:
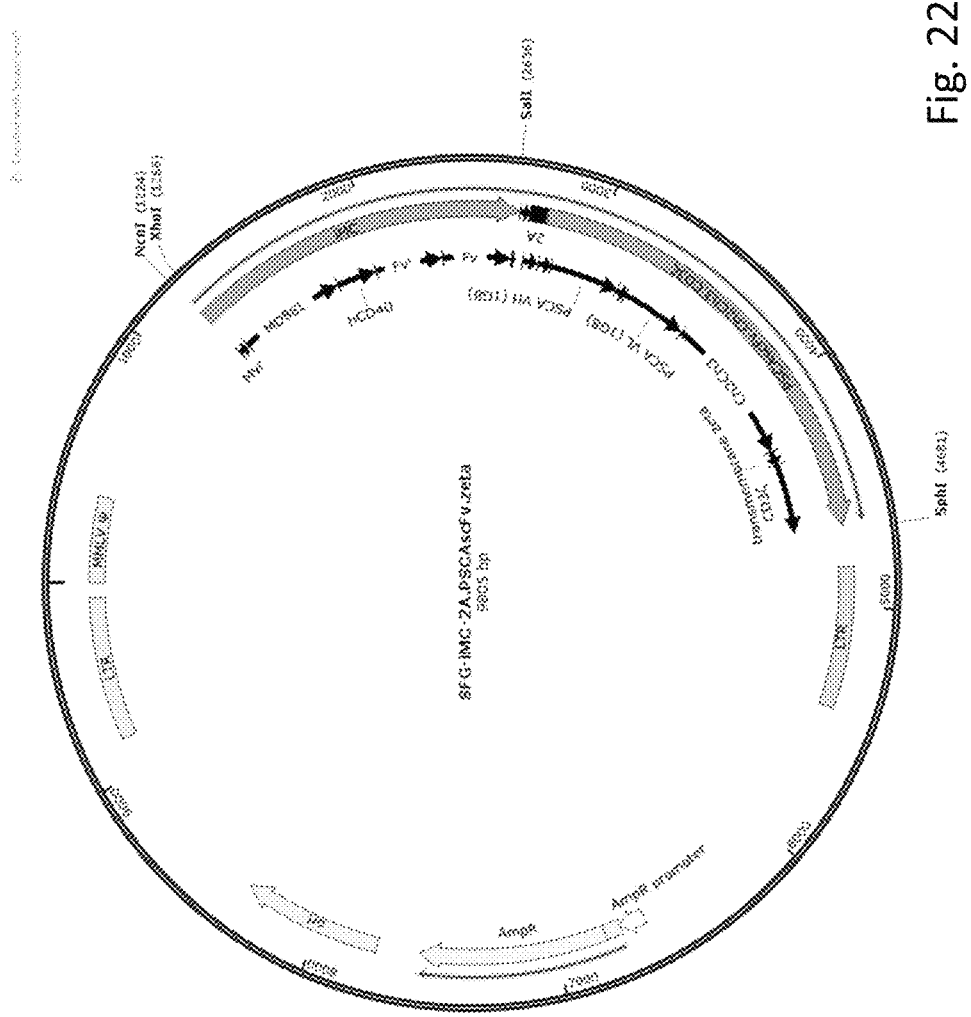
FIG. 22 is a plasmid map of an inducible chimeric antigen receptor.

As shown in FIG. 22, in some embodiments, the inducible co-stimulatory polypeptide, such as, for example, a CD40 cytoplasmic region polypeptide or a truncated MyD88 polypeptide is used to control activation of the chimeric antigen receptor itself. A polynucleotide that encodes this modified inducible chimeric antigen receptor may be used to transduce cells, such as, for example T cells. The cells may further express a chimeric signaling molecule as discussed herein, and in certain embodiments, the chimeric signaling molecule comprises a CD3 zeta polypeptide. In some embodiments, the inducible chimeric antigen receptor comprises both a CD40 cytoplasmic region polypeptide and a MyD88 polypeptide.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct between the host and donor cells.

Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorfei, Plasmodium*, herpes simplex viruses, human immunodeficiency virus, papillomavirus, *Vibrio cholera, E. coli*, measles virus, rotavirus, *shigella, Salmonella typhi, Neisseria gonorrhea*.

Therefore, any macromolecules, including virtually all proteins or peptides, can serve as antigens. Furthermore, antigens can be derived from recombinant or genomic DNA. Any DNA that contains nucleotide sequences or partial nucleotide sequences of a pathogenic genome or a gene or a fragment of a gene for a protein that elicits an immune response results in synthesis of an antigen. Furthermore, the present methods are not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

As used herein, the term "ex vivo" refers to "outside" the body. The terms "ex vivo" and "in vitro" can be used interchangeably herein.

As used herein, the term "functionally equivalent," as it relates to a co-stimulatory polypeptide, the cytoplasmic region, or the signaling region, as it refers to nucleic acid fragment, variant, or analog, refers to a nucleic acid that codes for a co-stimulatory that stimulates an immune response to destroy tumors or hyperproliferative disease. "Functionally equivalent" refers, for example, to a co-stimulatory polypeptide that is lacking the extracellular domain, but is capable of amplifying the T cell-mediated tumor killing response when expressed in T cells.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human. In some embodiments, the subject is a mammal. In some embodiments, the subject is a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. Nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, polynucleotides include mutations of the polynucleotides, include but are not limited to, mutation of the nucleotides, or nucleosides by methods well known in the art. A nucleic acid may comprise one or more polynucleotides.

As used herein, the term "polypeptide" is defined as a chain of amino acid residues, usually having a defined sequence. As used herein the term polypeptide may be interchangeable with the term proteins.

As used herein, the term "promoter" is defined as a DNA sequence recognized by the synthetic machinery of the cell, or introduced synthetic machinery, required to initiate the specific transcription of a gene.

As used herein, the terms "regulate an immune response," "modulate an immune response," or "control an immune response," refer to the ability to modify the immune response. For example, the composition is capable of enhancing and/or activating the immune response. Still further, the composition is also capable of inhibiting the immune response. The form of regulation is determined by the ligand that is used with the composition. For example, a dimeric analog of the chemical results in dimerization of the co-stimulatory polypeptide leading to activation of the T cell, however, a monomeric analog of the chemical does not result in dimerization of the co-stimulatory polypeptide, which would not activate the T cells.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeably.

The term "terms "patient" or "subject"" are interchangeable, and, as used herein includes include, but is are not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "vaccine" refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy. When used with respect to a solid tumor, such as a cancerous solid tumor, for example, the term refers to prevention by prophylactic treatment, which increases the subject's resistance to solid tumors or cancer. In some examples, the subject may be treated to prevent cancer, where the cancer is familial, or is genetically associated. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

Blood disease: The terms "blood disease", "blood disease" and/or "diseases of the blood" as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

Bone marrow disease: The term "bone marrow disease" as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnocytopenia, anemia, multiple myeloma and the like.

T cells and Activated T cells (include that this means CD3+ cells): T cells (also referred to as T lymphocytes) belong to a group of white blood cells referred to as lymphocytes. Lymphocytes generally are involved in cell-mediated immunity. The "T" in "T cells" refers to cells derived from or whose maturation is influenced by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histocompatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD 4 expression are referred to as CD3+ or CD4+). CD3 and CD4 proteins are cell surface receptors or co-receptors that may be directly and/or indirectly involved in signal transduction in T cells.

Peripheral blood: The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

By "kill" or "killing" as in a percent of cells killed, is meant the death of a cell through apoptosis, as measured using any method known for measuring apoptosis. The term may also refer to cell ablation.

Donor T cell: The term "donor T cell" as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GVHD). Certain activated donor T cells can cause a higher or lower GvHD response than other activated T cells. Donor T cells may also be reactive against recipient tumor cells, causing a beneficial graft vs. tumor effect.

Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the preferred settings are those that results in the highest sequence similarity.

Mesenchymal stromal cell: The terms "mesenchymal stromal cell" or "bone marrow derived mesenchymal stromal cell" as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

Embryonic stem cell: The term "embryonic stem cell" as used herein, refers to pluripotent stem cells derived from the inner cell mass of the blastocyst, an early-stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from mutipotent in that pluripotent cells can generate all cell types, while multipotent cells (e.g., adult stem cells) can only produce a limited number of cell types.

Inducible pluripotent stem cell: The terms "inducible pluripotent stem cell" or "induced pluripotent stem cell" as used herein refers to adult, or differentiated cells, that are "reprogrammed" or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells.

CD34+ cell: The term "CD34+ cell" as used herein refers to a cell expressing the CD34 protein on its cell surface. "CD34" as used herein refers to a cell surface glycoprotein (e.g., sialomucin protein) that often acts as a cell-cell adhesion factor and is involved in T cell entrance into lymph nodes, and is a member of the "cluster of differentiation" gene family. CD34 also may mediate the attachment of stem cells to bone marrow, extracellular matrix or directly to stromal cells. CD34+ cells often are found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population of dendritic cells (which are factor XIIIa negative) in the interstitium and around the adnexa of dermis of skin, as well as cells in certain soft tissue tumors (e.g., alveolar soft part sarcoma, pre-B acute lymphoblastic leukemia (Pre-B-ALL), acute myelogenous leukemia (AML), AML-M7, dermatofibrosarcoma protuberans, gastrointestinal stromal tumors, giant cell fibroblastoma, granulocytic sarcoma, Kaposi's sarcoma, liposarcoma, malignant fibrous histiocytoma, malignant peripheral nerve sheath tumors, mengingeal hemangiopericytomas, meningiomas, neurofibromas, schwannomas, and papillary thyroid carcinoma).

Tumor infiltrating lymphocytes (TILs) refer to T cells having various receptors which infiltrate tumors and kill tumor cells in a targeted manor. Regulating the activity of the TILs using the methods of the present application would allow for more direct control of the elimination of tumor cells.

Gene expression vector: The terms "gene expression vector", "nucleic acid expression vector", or "expression vector" as used herein, which can be used interchangeably throughout the document, generally refers to a nucleic acid molecule (e.g., a plasmid, phage, autonomously replicating sequence (ARS), artificial chromosome, yeast artificial chromosome (e.g., YAC)) that can be replicated in a host cell and be utilized to introduce a gene or genes into a host cell. The genes introduced on the expression vector can be endogenous genes (e.g., a gene normally found in the host cell or organism) or heterologous genes (e.g., genes not normally found in the genome or on extra-chromosomal nucleic acids of the host cell or organism). The genes introduced into a cell by an expression vector can be native genes or genes that have been modified or engineered. The gene expression vector also can be engineered to contain 5' and 3' untranslated regulatory sequences that sometimes can function as enhancer sequences, promoter regions and/or terminator sequences that can facilitate or enhance efficient transcription of the gene or genes carried on the expression vector. A gene expression vector sometimes also is engineered for replication and/or expression functionality (e.g., transcription and translation) in a particular cell type, cell location, or tissue type. Expression vectors sometimes include a selectable marker for maintenance of the vector in the host or recipient cell.

Developmentally regulated promoter: The term "developmentally regulated promoter" as used herein refers to a promoter that acts as the initial binding site for RNA polymerase to transcribe a gene which is expressed under certain conditions that are controlled, initiated by or influenced by a developmental program or pathway. Developmentally regulated promoters often have additional control regions at or near the promoter region for binding activators or repressors of transcription that can influence transcription of a gene that is part of a development program or pathway. Developmentally regulated promoters sometimes are involved in transcribing genes whose gene products influence the developmental differentiation of cells.

Developmentally differentiated cells: The term "developmentally differentiated cells", as used herein refers to cells that have undergone a process, often involving expression of specific developmentally regulated genes, by which the cell evolves from a less specialized form to a more specialized form in order to perform a specific function. Non-limiting examples of developmentally differentiated cells are liver cells, lung cells, skin cells, nerve cells, blood cells, and the like. Changes in developmental differentiation generally involve changes in gene expression (e.g., changes in patterns of gene expression), genetic re-organization (e.g., remodeling or chromatin to hide or expose genes that will be silenced or expressed, respectively), and occasionally involve changes in DNA sequences (e.g., immune diversity differentiation). Cellular differentiation during development can be understood as the result of a gene regulatory network. A regulatory gene and its cis-regulatory modules are nodes in a gene regulatory network that receive input (e.g., protein expressed upstream in a development pathway or program) and create output elsewhere in the network (e.g., the expressed gene product acts on other genes downstream in the developmental pathway or program).

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

In some embodiments, the nucleic acid is contained within a viral vector. In certain embodiments, the viral vector is a retroviral or lentiviral vector. It is understood that in some embodiments, the T cell is contacted with the viral vector ex vivo, and in some embodiments, the T cell is contacted with the viral vector in vivo.

Engineering Expression Constructs

Expression constructs encode a co-stimulatory polypeptide and a ligand-binding domain, all operatively linked. In general, the term "operably linked" is meant to indicate that the promoter sequence is functionally linked to a second sequence, wherein the promoter sequence initiates and mediates transcription of the DNA corresponding to the second sequence. More particularly, more than one ligand-binding domain is used in the expression construct. Yet further, the expression construct contains a membrane-targeting sequence. Appropriate expression constructs may include a co-stimulatory polypeptide element on either side of the above FKBP ligand-binding elements. The expression construct may be inserted into a vector, for example a viral vector or plasmid. The steps of the methods provided may be performed using any suitable method, these methods include, without limitation, methods of transducing, transforming, or otherwise providing nucleic acid to the antigen-presenting cell, presented herein.

The expression constructs may further comprise a marker polypeptide. In certain embodiments, the marker polypeptide is linked to the co-stimulatory polypeptide. For example, the marker polypeptide may be linked to the co-stimulatory polypeptide via a polypeptide sequence, such as, for example, a cleavable 2A-like sequence. The marker polypeptide may be, for example, CD19, ΔCD19, or may be, for example, a heterologous protein, selected to not affect the activity of the inducible CSM.

2A-like sequences, or "cleavable" 2A sequences, are derived from, for example, many different viruses, including, for example, from *Thosea asigna*. These sequences are sometimes also known as "peptide skipping sequences." When this type of sequence is placed within a cistron, between two peptides that are intended to be separated, the ribosome appears to skip a peptide bond, in the case of *Thosea asigna* sequence, the bond between the Gly and Pro amino acids is omitted. This leaves two to three polypeptides, in this case the co-stimulatory polypeptide cytoplasmic region and the marker polypeptide. When this sequence is used, the peptide that is encoded 5' of the 2A sequence may end up with additional amino acids at the carboxy terminus, including the Gly residue and any upstream in the 2A sequence. The peptide that is encoded 3' of the 2A sequence may end up with additional amino acids at the amino terminus, including the Pro residue and any downstream in the 2A sequence.

Co-Stimulatory Polypeptides

Co-stimulatory polypeptide molecules are capable of amplifying the cell-mediated immune response through activation of signaling pathways involved in cell survival and proliferation. Co-stimulatory proteins that are contemplated include, for example, but are not limited to, the members of tumor necrosis factor receptor (TNFR) family (i.e., CD40, RANK/TRANCE-R, OX40, 4-1BB) and CD28 family members (CD28, ICOS). Co-stimulatory proteins may include, for example, CD28, 4-1BB, OX40, and the CD3 zeta chain, or, for example, the cytoplasmic regions thereof. More than one co-stimulatory polypeptide, or co-stimulatory polypeptide cytoplasmic region may be used in the inducible chimeric signaling molecules discussed herein. For example, the inducible CSM may comprise a CD28 cytoplasmic polypeptide and a 4-1BB cytoplasmic polypeptide. Or, for example, the inducible CSM may comprise a CD28 cytoplasmic polypeptide and an OX40 cytoplasmic polypeptide. Or, for example, the inducible CSM may further comprise a CD3 zeta domain polypeptide.

Co-stimulatory polypeptides include any molecule or polypeptide that activates the NF-kappaB pathway, Akt pathway, and/or p38 pathway. The cellular activation system is based upon utilizing a recombinant signaling molecule fused to one or more ligand-binding domains (i.e., a small molecule binding domain) in which the co-stimulatory polypeptide is activated and/or regulated with a ligand resulting in oligomerization (i.e., a lipid-permeable, organic, dimerizing drug). Other systems that may be used for crosslinking, or for oligomerization, of co-stimulatory polypeptides include antibodies, natural ligands, and/or artificial cross-reacting or synthetic ligands. Yet further, another dimerization systems contemplated include the coumermycin/DNA gyrase B system.

Co-stimulatory polypeptides that can be used include those that activate NF-kappaB and other variable signaling cascades for example the p38 pathway and/or Akt pathway. Such co-stimulatory polypeptides include, but are not limited to CD28 family members (e.g. CD28, ICOS), TNF receptors (i.e., CD40, RANK/TRANCE-R, OX40, 4-1BB).

In certain embodiments, the present methods involve the manipulation of genetic material to produce expression constructs that encode an inducible form of the co-stimulatory polypeptide (for example, iCD28, i-4-1BB, iCD3-zeta). Such methods involve the generation of expression constructs containing, for example, a heterologous nucleic acid sequence encoding the respective cytoplasmic domain and a means for its expression. The vector can be replicated in an appropriate helper cell, viral particles may be produced therefrom, and cells infected with the recombinant virus particles.

Thus, the co-stimulatory molecule presented herein may, for example, lack the extracellular domain. In specific embodiments, the extracellular domain is truncated or removed. It is also contemplated that the extracellular domain can be mutated using standard mutagenesis, insertions, deletions, or substitutions to produce a co-stimulatory molecule that does not have a functional extracellular domain.

Figure 21:
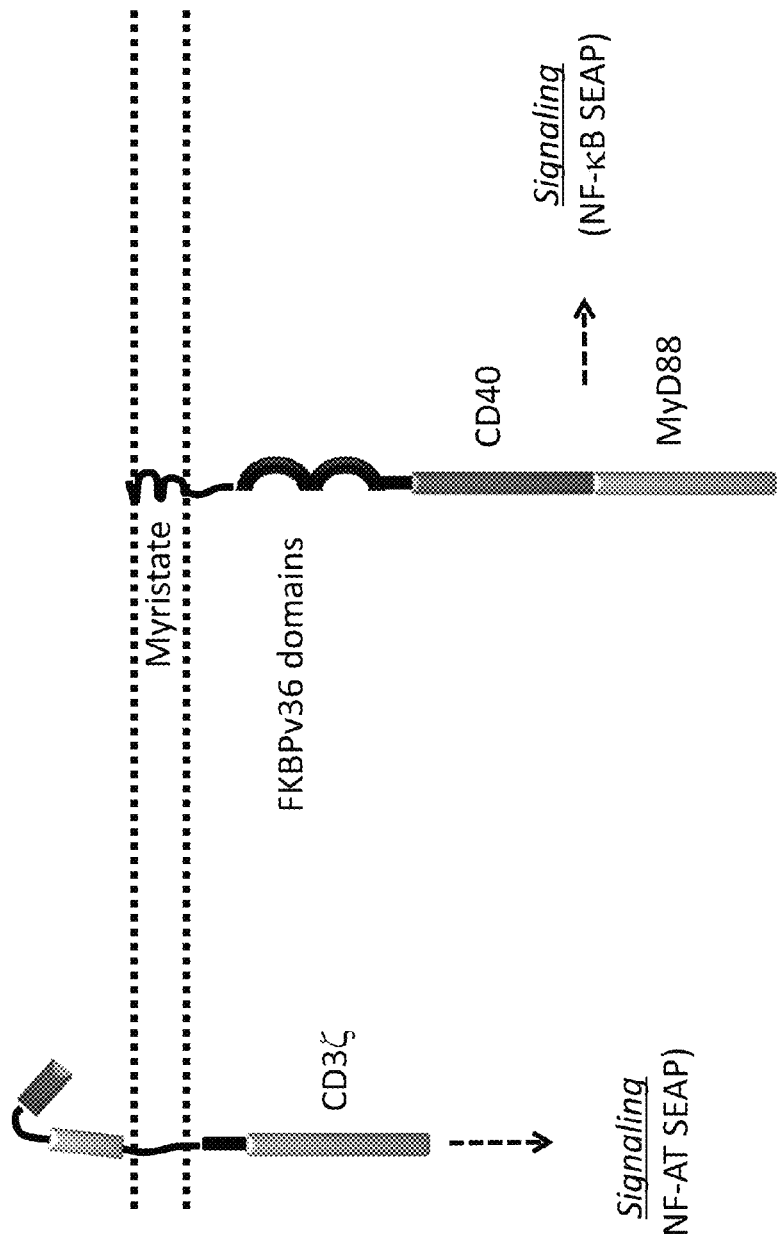
FIG. 21 is a schematic of a cell transduced or transfected with a chimeric antigen receptor (left) and an example of a chimeric signaling molecule as provided herein.

In some embodiments, the chimeric signaling molecule comprises a CD40 cytoplasmic region polypeptide and a truncated MyD88 polypeptide as shown in, for example, FIG. 21. Polypeptides comprising CD40 cytoplasmic region polypeptides and truncated MyD88 polypeptides are discussed in U.S. patent application Ser. No. 12/563,991, filed Sep. 21, 2009, entitled METHODS AND COMPOSITIONS FOR GENERATING AN IMMUNE RESPONSE BY INDUCING CD40 AND PATTERN RECOGNITION RECEPTOR ADAPTERS, which is hereby incorporated by reference herein in its entirety.

In the context of gene therapy, the gene will be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source.

Co-stimulatory polypeptides may comprise, but are not limited to, the amino acid sequences provided herein, may include functional conservative mutations, including deletions or truncations, and may comprise amino acid sequences that are 70%, 75%, 80%, 85%, 90%, 95% or 100% identical to the amino acid sequences provided herein.

Ligand-Binding Regions

The ligand-binding ("dimerization") domain of the expression construct can be any convenient domain that will allow for induction using a natural or unnatural ligand, for example, an unnatural synthetic ligand. The multimerizing region, or ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises an $F_vF_{vls}$ sequence. Sometimes, the $F_v$ $F_{vls}$ sequence further comprises an additional Fv' sequence. Examples include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology From Small Molecules to Systems Biology and Drug Design (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric, nonimmunogenic, have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen).

Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the ligand receptor domain. By "multimeric ligand binding region" is meant a ligand binding region that binds to a multimeric ligand. The term "multimeric ligands" include dimeric ligands. A dimeric ligand will have two binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker domain, or modified receptors, and mutated sequences thereof, and the like, any of a large variety of compounds can be used. A significant characteristic of these ligand units is that each binding site is able to bind the receptor with high affinity and they are able to be dimerized chemically. Also, methods are available to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. FKBP12 variants having amino acid substitutions and deletions, such as FKBP12,36, that bind to a dimerizer drug, may also be used. In addition, the synthetic ligands are resistant to protease degradation, making them more efficient at activating receptors in vivo than most delivered protein agents.

The ligands used are capable of binding to two or more of the ligand-binding domains. The chimeric signaling molecules may be able to bind to more than one ligand when they contain more than one ligand-binding domain. The ligand is typically a non-protein or a chemical. Exemplary ligands include, but are not limited to dimeric FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug AP1903 (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by AP1903.

F36V'-FKBP: F36V'-FKBP is a codon-wobbled version of F36V-FKBP. It encodes the identical polypeptide sequence as F36V-FKPB but has only 62% homology at the nucleotide level. F36V'-FKBP was designed to reduce recombination in retroviral vectors (Schellhammer, P. F. et al., J. Urol. 157, 1731-5 (1997)). F36V'-FKBP was constructed by a PCR assembly procedure. The transgene contains one copy of F36V'-FKBP linked directly to one copy of F36V-FKBP.

In some embodiments, the ligand is a small molecule. The appropriate ligand for the selected ligand-binding region may be selected. Often, the ligand is dimeric, sometimes, the ligand is a dimeric FK506 or a dimeric FK506 analog. In certain embodiments, the ligand is AP1903 (CAS Index Name: 2-Piperidinecarboxylic acid, 1-[(2S)-1-oxo-2-(3,4,5-trimethoxyphenyl)butyl]-, 1,2-ethanediylbis[imino(2-oxo-2,1-ethanediyl)oxy-3,1-phenylene[(1R)-3-(3,4-dimethoxyphenyl)propylidene]]ester, [2S-[1(R*),2R*[S*[S*[1(R*), 2R*]]]]]-(9Cl) CAS Registry Number: 195514-63-7; Molecular Formula: C78H98N4O20 Molecular Weight: 1411.65). In certain embodiments, the ligand is AP20187. In certain embodiments, the ligand is an AP20187 analog, such as, for example, AP1510. In some embodiments, certain analogs will be appropriate for the FKBP12, and certain analogs appropriate for the wobbled version of FKBP12. In certain embodiments, one ligand binding region is included in the chimeric protein. In other embodiments, two or more ligand binding regions are included. Where, for example, the ligand binding region is FKBP12, where two of these regions are included, one may, for example, be the wobbled version.

Other dimerization systems contemplated include the coumermycin/DNA gyrase B system. Coumermycin-induced dimerization activates a modified Raf protein and stimulates the MAP kinase cascade. See Farrar et al., 1996.

Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S-N-K-S-K-P-K-D-A-S-Q-R-R-R (SEQ ID NO: 111)) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 112), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or C10 isoprenyl moieties, from the C-terminus of G-protein gamma subunits and other proteins (e.g., World Wide Web address ebi.ac.uk/interpro/DisplayIproEntry?ac=IPRO01230) also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein. In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition discussed above and tested for antimicrobial activity using known methods and those discussed hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association region.

A chimeric protein herein also may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFbeta, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

Any membrane-targeting sequence can be employed that is functional in the host and may, or may not, be associated with one of the other domains of the chimeric protein. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster J P et al, Biology of the Cell (2007) 99, 1-12, Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-P3, PI (3,4)-P2, PI (4,5)-P2) and thus play a key role in recruiting proteins to different membrane or cellular compartments. Often the phosphorylation state of PI lipids is regulated, such as by PI-3 kinase or PTEN, and thus, interaction of membranes with PH domains is not as stable as by acyl lipids.

AP1903 API is manufactured by Alphora Research Inc. and AP1903 Drug Product for Injection is made by AAI Pharma Services Corp. It is formulated as a 5 mg/mL solution of AP1903 in a 25% solution of the non-ionic solubilizer Solutol HS15 (250 mg/mL, BASF). At room temperature, this formulation is a clear solution. Upon refrigeration, this formulation undergoes a reversible phase transition on extended storage, resulting in a milky solution. This phase transition is reversed upon re-warming to room temperature. The fill is 8 mL in a 10 mL glass vial (~40 mg AP1903 for Injection total per vial).

For use, the AP1903 will be warmed to room temperature and diluted prior to administration. For subjects over 50 kg, the AP1903 is administered via i.v. infusion at a dose of 40 mg diluted in 100 mL physiological saline over 2 hours at a rate of 50 mL per hour using a DEHP-free saline bag and solution set. Subjects less than 50 kg receive 0.4 mg/kg AP1903.

All study medication is maintained at a temperature between 2 degrees C. and 8 degrees C., protected from excessive light and heat, and stored in a locked area with restricted access.

Upon determining a need to administer AP1903 and activate the therapeutic T cells, for example the chimeric antigen-receptor and inducible chimeric signaling molecule-expressing T cells, patients may be, for example, administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by 0%. The calculated dose is diluted in 100 mL in 0.9% normal saline before infusion.

In a previous Phase I study of AP1903, 24 healthy volunteers were treated with single doses of AP1903 for Injection at dose levels of 0.01, 0.05, 0.1, 0.5 and 1.0 mg/kg infused IV over 2 hours. AP1903 plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 for injection used, for example, may be 0.4 mg/kg intravenously infused over 2 hours. The amount of AP1903 needed in vitro for effective signaling of cells is about 10-100 nM (MW: 1412 Da). This equates to 14-140 μg/L or ~0.014-0.14 mg/kg (1.4-140 μg/kg). The dosage may vary according to the application, and may, in certain examples, be more in the range of 0.1-10 nM, or in the range of 50-150 nM, 10-200 nM, 75-125 nM, 100-500 nM, 100-600 nM, 100-700 nM, 100-800 nM, or 100-900 nM. Doses up to 1 mg/kg were well-tolerated in the Phase I study of AP1903 described above.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, beta-gal or chloramphenicol acetyltransferase (CAT). In certain embodiments, the marker protein, such as, for example, CD19 is used for selection of the cells for transfusion, such as, for example, in immunomagnetic selection.

Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that may be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

In other examples, promoters may be selected that are developmentally regulated and are active in particular differentiated cells. Thus, for example, a promoter may not be active in a pluripotent stem cell, but, for example, where the pluripotent stem cell differentiates into a more mature cell, the promoter may then be activated.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity. (Bojak, A., et al., 2002. Vaccine 20:1975-79; Cazeaux, N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29 (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-alpha, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP alpha, IL-1, IL-6 (Poli and Cortese, (1989) Proc. Nat'l Acad. Sci. USA, 86, 8202-8206), Complement C3 (Wilson et al., (1990) Mol. Cell. Biol., 6181-6191), IL-8, alpha-1 acid glycoprotein (Prowse and Baumann, (1988) Mol Cell Biol, 8, 42-51), alpha-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole stimulates transcription at a distance and often independent of orientation; this need not be true of a promoter region or its component elements. On the other hand, a promoter has one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers includes locus-control regions (LCRs) that can not only increase transcriptional activity, but (along with insulator elements) can also help to insulate the transcriptional element from adjacent sequences when integrated into the genome. Any promoter/enhancer combination (as per the Eukaryotic Promoter Data Base EPDB) can be used to drive expression of the gene, although many will restrict expression to a particular tissue type or subset of tissues. (reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Appropriate enhancers may be selected for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. One non-limiting example is the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA. (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. The initiation codon is placed in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been discussed (Pelletier and Sonenberg, 1988), as well an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Sequence Optimization

Protein production may also be increased by optimizing the codons in the transgene. Species specific codon changes may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed. (Kutzler, M. A., and Weiner, D. B., 2008. Nature Rev. Gen. 9:776-88; Yan, J. et al., 2007. Mol. Ther. 15:411-21; Cheung, Y. K., et al., 2004. Vaccine 23:629-38; Narum, D. L., et al., 2001. 69:7250-55; Yadava, A., and Ockenhouse, C. F., 2003. Infect. Immun. 71:4962-69; Smith, J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635). For example, the FBP12 or other multimerizing region polypeptide, the co-stimulatory polypeptide cytoplasmic signaling region, and the CD19 sequences may be optimized by changes in the codons.

Leader Sequences

Leader sequences may be added to enhance the stability of mRNA and result in more efficient translation. The leader sequence is usually involved in targeting the mRNA to the endoplasmic reticulum. Examples include the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; L1, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang, J. S., et al., 2002. Emerg. Infect. Dis. 8:1379-84; Kumar, S., et al., 2006. DNA Cell Biol. 25:383-92; Wang, S., et al., 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression. These methods include, for example, optimizing promoters, delivery methods, and gene sequences, (for example, as presented in Laddy, D. J., et al., 2008. PLoS. ONE 3 e2517; Kutzler, M. A., and Weiner, D. B., 2008. Nature Rev. Gen. 9:776-88).

Nucleic Acids

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the preferred settings are those that results in the highest sequence similarity.

Nucleic Acid Modification

Any of the modifications discussed below may be applied to a nucleic acid. Examples of modifications include alterations to the RNA or DNA backbone, sugar or base, and various combinations thereof. Any suitable number of backbone linkages, sugars and/or bases in a nucleic acid can be modified (e.g., independently about 5%, 10%, 15%, 20%, 25%, 30%, 35%, 40%, 45%, 50%, 55%, 60%, 65%, 70%, 75%, 80%, 85%, 90%, 95%, up to 100%). An unmodified nucleoside is any one of the bases adenine, cytosine, guanine, thymine, or uracil joined to the 1' carbon of beta-D-ribo-furanose.

A modified base is a nucleotide base other than adenine, guanine, cytosine and uracil at a 1' position. Non-limiting examples of modified bases include inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and the like. Other non-limiting examples of modified bases include nitropyrrolyl (e.g., 3-nitropyrrolyl), nitroindolyl (e.g., 4-, 5-, 6-nitroindolyl), hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, difluorotolyl, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl and the like.

In some embodiments, for example, a nucleid acid may comprise modified nucleic acid molecules, with phosphate backbone modifications. Non-limiting examples of backbone modifications include phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl modifications. In certain instances, a ribose sugar moiety that naturally occurs in a nucleoside is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. The hexose may be a D-hexose, glucose, or mannose. In certain instances, the polycyclic heteroalkyl group may be a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane.

Nitropyrrolyl and nitroindolyl nucleobases are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, oligonucleotide duplexes containing 3-nitropyrrolyl nucleobases may be stabilized solely by stacking interactions. The absence of significant hydrogen-bonding interactions with nitropyrrolyl nucleobases obviates the specificity for a specific complementary base. In addition, 4-, 5- and 6-nitroindolyl display very little specificity for the four natural bases. Procedures for the preparation of 1-(2'-O-methyl-beta.-D-ribofuranosyl)-5-nitroindole are discussed in Gaubert, G.; Wengel, J. Tetrahedron Letters 2004, 45, 5629. Other universal bases include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof.

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994);

In addition, chemical substituents, for example cross-linking agents, may be used to add further stability or irreversibility to the reaction. Non-limiting examples of cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

A nucleotide analog may also include a "locked" nucleic acid. Certain compositions can be used to essentially "anchor" or "lock" an endogenous nucleic acid into a particular structure. Anchoring sequences serve to prevent disassociation of a nucleic acid complex, and thus not only can prevent copying but may also enable labeling, modification, and/or cloning of the endogenous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

Nucleic acid molecules need not be limited to those molecules containing only RNA or DNA, but further encompass chemically-modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%).

Nucleic Acid Preparation

In some embodiments, a nucleic acid is provided for use as a control or standard in an assay, or therapeutic, for example. A nucleic acid may be made by any technique known in the art, such as for example, chemical synthesis, enzymatic production or biological production. Nucleic acids may be recovered or isolated from a biological sample. The nucleic acid may be recombinant or it may be natural or endogenous to the cell (produced from the cell's genome). It is contemplated that a biological sample may be treated in a way so as to enhance the recovery of small nucleic acid molecules. Generally, methods may involve lysing cells with a solution having guanidinium and a detergent.

Nucleic acid synthesis may also be performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques or via deoxynucleoside H-phosphonate intermediates. Various different mechanisms of oligonucleotide synthesis have been disclosed elsewhere.

Nucleic acids may be isolated using known techniques. In particular embodiments, methods for isolating small nucleic acid molecules, and/or isolating RNA molecules can be employed. Chromatography is a process used to separate or isolate nucleic acids from protein or from other nucleic acids. Such methods can involve electrophoresis with a gel matrix, filter columns, alcohol precipitation, and/or other chromatography. If a nucleic acid from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column is effective for such isolation procedures.

A nucleic acid isolation processes may sometimes include: a) lysing cells in the sample with a lysing solution comprising guanidinium, where a lysate with a concentration of at least about 1 M guanidinium is produced; b) extracting nucleic acid molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the nucleic acid molecules from the solid support with an ionic solution; and, f) capturing the nucleic acid molecules. The sample may be dried down and resuspended in a liquid and volume appropriate for subsequent manipulation.

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer. A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials.

An appropriate host may be determined. Generally this is based on the vector backbone and the desired result. A plasmid or cosmid, for example, can be introduced into a prokaryote host cell for replication of many vectors. Bacterial cells used as host cells for vector replication and/or expression include DH5alpha, JM109, and KC8, as well as a number of commercially available bacterial hosts such as SURE® Competent Cells and SOLOPACK Gold Cells (STRATAGENE®, La Jolla, Calif.). Alternatively, bacterial cells such as E. coli LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Nucleic acid vaccines may include, for example, non-viral DNA vectors, "naked" DNA and RNA, and viral vectors. Methods of transforming cells with these vaccines, and for optimizing the expression of genes included in these vaccines are known and are also discussed herein.

Examples of Methods of Nucleic Acid or Viral Vector Transfer

Any appropriate method may be used to transfect or transform the cell, for example, the T cells, or to administer the nucleotide sequences or compositions of the present methods. Certain examples are presented herein, and further include methods such as delivery using cationic polymers, lipid like molecules, and certain commercial products such as, for example, IN-VIVO-JET PEI.

1. Ex Vivo Transformation

Various methods are available for transfecting vascular cells and tissues removed from an organism in an ex vivo setting. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism. For example, dendritic cells from an animal, transfect the cells with the expression vector and then administer the transfected or transformed cells back to the animal.

2. Injection

In certain embodiments, an antigen presenting cell or a nucleic acid or viral vector may be delivered to an organelle, a cell, a tissue or an organism via one or more injections (i.e., a needle injection), such as, for example, subcutaneous, intradermal, intramuscular, intravenous, intraprotatic, intratumor, intrintraperitoneal, etc. Methods of injection include, foe example, injection of a composition comprising a saline solution. Further embodiments include the introduction of a polynucleotide by direct microinjection. The amount of the expression vector used may vary upon the nature of the antigen as well as the organelle, cell, tissue or organism used. Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair is clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell Biol., 6, 716-718) in this manner.

In vivo electroporation for vaccines, or eVac, is clinically implemented through a simple injection technique. A DNA vector encoding tumor antigen is injected intradermally in a patient. Then electrodes apply electrical pulses to the intradermal space causing the cells localized there, especially resident dermal dendritic cells, to take up the DNA vector and express the encoded tumor antigen. These tumor antigen-expressing dendritic cells activated by local inflammation can then migrate to lymph-nodes, presenting tumor antigens and priming tumor antigen-specific T cells. A nucleic acid is electroporetically administered when it is administered using electroporation, following, for example, but not limited to, injection of the nucleic acid or any other means of administration where the nucleic acid may be delivered to the cells by electroporation Methods of electroporation are discussed in, for example, Sardesai, N. Y., and Weiner, D. B., Current Opinion in Immunotherapy 23:421-9 (2011) and Ferraro, B. et al., Human Vaccines 7:120-127 (2011), which are hereby incorporated by reference herein in their entirety.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52, 456-467) using this technique. Also in this manner, mouse L(A9), mouse C127, CHO, CV-1, BHK, NIH3T3 and HeLa cells were transfected with a neomycin marker gene (Chen and Okayama, Mol. Cell Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7. Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been discussed (Wu and Wu, Adv. Drug Delivery Rev., 12:159-167, 1993; incorporated herein by reference). In certain aspects, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149, 157-176). It is contemplated that the tissue-specific transforming constructs may be specifically delivered into a target cell in a similar manner.

9. Microprojectile Bombardment

Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods. In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold, including, for example, nanoparticles. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

Examples of Methods of Viral Vector-Mediated Transfer

Any viral vector suitable for administering nucleotide sequences, or compositions comprising nucleotide sequences, to a cell or to a subject, such that the cell or cells in the subject may express the genes encoded by the nucleotide sequences may be employed in the present methods. In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector may permits replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells, such as Tcells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990). Thus, for example, the present technology includes, for example, cells whereby the polynucleotide used to transduce the cell is integrated into the genome of the cell.

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248). An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may be desired.

A different approach to targeting of recombinant retroviruses was designed which used biotinylated antibodies against a retroviral envelope protein and against a specific cell receptor. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

4. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Methods for Treating a Disease

The present methods also encompass methods of treatment or prevention of a disease where administration of cells by, for example, infusion, may be beneficial.

Cells, such as, for example, T cells, tumor infiltrating lymphocytes, natural killer cells, natural killer T cells, or progenitor cells, such as, for example, hematopoietic stem cells, mesenchymal stromal cells, stem cells, pluripotent stem cells, and embryonic stem cells may be used for cell therapy. The cells may be from a donor, or may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. Mesenchymal stromal cells have also, for example, been used to provide immunosuppressive activity, and may be used in the treatment of graft versus host disease and autoimmune disorders.

The cells provided in the present application contain a safety switch that may be valuable in a situation where following cell therapy, the activity of the therapeutic cells needs to be increased, or decreased. For example, where T cells that express a chimeric antigen receptor are provided to the patient, in some situations there may be an adverse event, such as off-target toxicity. Ceasing the administration of the ligand would return the therapeutic T cells to a non-activated state, remaining at a low, non-toxic, level of expression. Or, for example, the therapeutic cell may work to decrease the tumor cell, or tumor size, and may no longer be needed. In this situation, administration of the ligand may cease, and the therapeutic cells would no longer be activated. If the tumor cells return, or the tumor size increases following the initial therapy, the ligand may be administered again, in order to activate the chimeric antigen receptor-expressing T cells, and re-treat the patient.

By "therapeutic cell" is meant a cell used for cell therapy, that is, a cell administered to a subject to treat or prevent a condition or disease.

The term "unit dose" as it pertains to the inoculum refers to physically discrete units suitable as unitary dosages for mammals, each unit containing a predetermined quantity of pharmaceutical composition calculated to produce the desired immune-stimulating effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition, such as the multimeric ligand presented herein, would be the amount that achieves this selected result of activating the inducible CSM-expressing T cells, such that over 60%, 70%, 80%, 85%, 90%, 95%, or 97%, or that under 80%, 70%, 60%, 50%, 40%, 30%, 20%, or 10% of the therapeutic cells are activated. The term is also synonymous with "sufficient amount." The effective amount may also be the amount that achieves the desired therapeutic response, such as, the reduction of tumor size, the decrease in the level of tumor cells, or the decrease in the level of CD19-expressing leukemic cells, compared to the time before the ligand inducer is administered.

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

Optimized and Personalized Therapeutic Treatment

The dosage and administration schedule of the ligand inducer may be optimized by determining the level of the disease or condition to be treated. For example, the size of any remaining solid tumor, or the level of targeted cells such as, for example, tumor cells or CD19-expressing B cells, may that remain in the patient, may be determined.

For example, determining that a patient has clinically relevant levels of tumor cells, or a solid tumor, after initial therapy, provides an indication to a clinician that it may be necessary to activate the chimeric-antigen receptor-expressing T cells by activating the cells by administering the multimeric ligand. In another example, determining that a patient has a reduced level of tumor cells or reduced tumor size after treatment with the multimeric ligand may indicate to the clinician that no additional dose of the multimeric ligand is needed. Similarly, after treatment with the multimeric ligand, determining that the patient continues to exhibit disease or condition symptoms, or suffers a relapse of symptoms may indicate to the clinician that it may be necessary to administer at least one additional dose of multimeric ligand. The term "dosage" is meant to include both the amount of the dose and the frequency of administration, such as, for example, the timing of the next dose. The term "dosage level" refers to the amount of the multimeric ligand administered in relation to the body weight of the subject. Thus increasing the dosage level would mean increasing the amount of the ligand administered relative to the subject's weight. In addition, increasing the concentration of the dose administered, such as, for example, when the multimeric ligand is administered using a continuous infusion pump would mean that the concentration administered (and thus the amount administered) per minute, or second, is increased.

Thus, for example, in certain embodiments, the methods comprise determining the presence or absence of a tumor size increase and/or increase in the number of tumor cells in a subject relative to the tumor size and/or the number of tumor cells following administration of the multimeric ligand, and administering an additional dose of the multimeric ligand to the subject in the event the presence of a tumor size increase and/or increase in the number of tumor cells is determined. The methods also comprise, for example, determining the presence or absence of an increase in CD19-expressing B cells in the subject relative to the level of CD19-expressing B cells following administration of the multimeric ligand, and administering an additional dose of the multimeric ligand to the subject in the event the presence of an increase in CD19-expressing B cells in the subject is determined. In these embodiments, for example, the patient is initially treated with the therapeutic cells and ligand according to the methods provided herein. Following the initial treatment, the size of the tumor, the number of tumor cells, or the number of CD19-expressing B cells, for example, may decrease relative to the time prior to the initial treatment. At a certain time after this initial treatment, the patient is again tested, or the patient may be continually monitored for disease symptoms. If it is determined that the size of the tumor, the number of tumor cells, or the number of CD19-expressing B cells, for example, is increased relative to the time just after the initial treatment, then the ligand may be administered for an additional dose. This monitoring and treatment schedule may continue, because the therapeutic cells that express the inducible CSM remain in the patient, although in a relatively inactive state in the absence of additional ligand.

An indication of adjusting or maintaining a subsequent drug dose, such as, for example, a subsequent dose of the multimeric ligand, and/or the subsequent drug dosage, can be provided in any convenient manner. An indication may be provided in tabular form (e.g., in a physical or electronic medium) in some embodiments. For example, the size of the tumor cell, or the number or level of tumor cells in a sample may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms are provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

Formulations and Routes for Administration to Patients

Where clinical applications are contemplated, it will be necessary to prepare pharmaceutical compositions—expression constructs, expression vectors, fused proteins, transduced cells, activated T cells, transduced T cells—in a form appropriate for the intended application. Generally, this will entail preparing compositions that are essentially free of pyrogens, as well as other impurities that could be harmful to humans or animals.

The multimeric ligand, such as, for example, AP1903, may be delivered, for example at doses of about 0.01 to 1 mg/kg subject weight, of about 0.05 to 0.5 mg/kg subject weight, 0.1 to 2 mg/kg subject weight, of about 0.05 to 1.0 mg/kg subject weight, of about 0.1 to 5 mg/kg subject weight, of about 0.2 to 4 mg/kg subject weight, of about 0.3 to 3 mg/kg subject weight, of about 0.3 to 2 mg/kg subject weight, or about 0.3 to 1 mg/kg subject weight, for example, about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight. In some embodiments, the ligand is provided at 0.4 mg/kg per dose, for example at a concentration of 5 mg/mL. Vials or other containers may be provided containing the ligand at, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

One may generally desire to employ appropriate salts and buffers to render delivery vectors stable and allow for uptake by target cells. Buffers also may be employed when recombinant cells are introduced into a patient. Aqueous compositions comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route.

This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form is sterile and is fluid to the extent that easy syringability exists. It is stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

The administration schedule may be determined as appropriate for the patient and may, for example, comprise a dosing schedule where the cells are administered at week 0, followed by induction by administration of the chemical inducer of dimerization, followed by administration of additional cells and inducer at 2 week intervals thereafter for a total of, for example, 2, 4, 6, 8, 10, 12, 14, 16, 18, 20, 22, 24, 26, 28, or 30 weeks.

Other dosing schedules include, for example, a schedule where one dose of the cells and one dose of the inducer are administered. In another example, the schedule may comprise administering the cells and the inducer are administered at week 0, followed by the administration of additional cells and inducer at 4 week intervals, for a total of, for example, 4, 8, 12, 16, 20, 24, 28, or 32 weeks.

Administration of a dose of cells may occur in one session, or in more than one session, but the term dose may refer to the total amount of cells administered before administration of the ligand.

If needed, the method may further include additional leukaphereses to obtain more cells to be used in treatment.

Methods for Treating a Disease

The present methods also encompass methods of treatment or prevention of a disease caused by pathogenic microorganisms and/or a hyperproliferative disease.

Diseases may be treated or prevented include diseases caused by viruses, bacteria, yeast, parasites, protozoa, cancer cells and the like. The pharmaceutical composition (transduced T cells, expression vector, expression construct, etc.) may be used as a generalized immune enhancer (T cell activating composition or system) and as such has utility in treating diseases. Exemplary diseases that can be treated and/or prevented include, but are not limited to, infections of viral etiology such as HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition (transduced T cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using T cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis. In the method of treatment, the administration of the pharmaceutical composition (expression construct, expression vector, fused protein, transduced cells, activated T cells, transduced T cells) may be for either "prophylactic" or "therapeutic" purpose. When provided prophylactically, the pharmaceutical composition is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the compositions presented herein may be provided either prior to the anticipated exposure to a disease-causing agent or disease state or after the initiation of the infection or disease.

Solid tumors from any tissue or organ may be treated using the present methods, including, for example, any tumor expressing PSA, for example, PSMA, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant myeloma.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

A. Genetic Based Therapies

In certain embodiments, a cell is provided with an expression construct capable of providing a co-stimulatory polypeptide, such as those discussed herein, and, for example, in a T cell. The lengthy discussion of expression vectors and the genetic elements employed therein is incorporated into this section by reference. In certain examples, the expression vectors may be viral vectors, such as adenovirus, adeno-associated virus, herpes virus, vaccinia virus and retrovirus. In another example, the vector may be a lysosomal-encapsulated expression vector.

Gene delivery may be performed in both in vivo and ex vivo situations. For viral vectors, one generally will prepare a viral vector stock. Examples of viral vector-mediated gene delivery ex vivo and in vivo are presented in the present application. For in vivo delivery, depending on the kind of virus and the titer attainable, one will deliver, for example, about 1, 2, 3, 4, 5, 6, 7, 8, or $9\times10^4$, 1, 2, 3, 4, 5, 6, 7, 8, or $9\times10^5$, 1, 2, 3, 4, 5, 6, 7, 8, or $9\times10^6$, 1, 2, 3, 4, 5, 6, 7, 8, or $9\times10^7$, 1, 2, 3, 4, 5, 6, 7, 8, or $9\times10^8$, 1, 2, 3, 4, 5, 6, 7, 8, or $9\times10^9$, 1, 2, 3, 4, 5, 6, 7, 8, or $9\times10^{10}$, 1, 2, 3, 4, 5, 6, 7, 8, or $9\times10^{11}$ or 1, 2, 3, 4, 5, 6, 7, 8, or $9\times10^{12}$ infectious particles to the patient. Similar figures may be extrapolated for liposomal or other non-viral formulations by comparing relative uptake efficiencies. Formulation as a pharmaceutically acceptable composition is discussed below. The multimeric ligand, such as, for example, AP1903, may be delivered, for example at doses of about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight.

B. Cell Based Therapy

Another therapy that is contemplated is the administration of transduced T cells. The T cells may be transduced in vitro. Formulation as a pharmaceutically acceptable composition is discussed herein.

In cell based therapies, the transduced T cells may be, for example, transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vectors presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/alternative therapies.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing. The administration of the pharmaceutical composition may precede, be co-current with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

In some embodiments, the chemotherapeutic agent may be Taxotere (docetaxel), or another taxane, such as, for example, cabazitaxel. The chemotherapeutic may be administered either before, during, or after treatment with the therapeutic cell and inducer. For example, the chemotherapeutic may be administered about 1 year, 11, 10, 9, 8, 7, 6, 5, or 4 months, or 18, 17, 16, 15, 14, 13, 12, 11, 10, 9, 8, 7, 6, 5, 4, 3, 2, weeks or 1 week prior to administering the first dose of T cells. Or, for example, the chemotherapeutic may be administered about 1 week or 2, 3, 4, 5, 6, 7, 8, 9, 10, 11, 12, 13, 14, 15, 16, 17, or 18 weeks or 4, 5, 6, 7, 8, 9, 10, or 11 months or 1 year after administering the first dose of T cells or inducer.

Administration of a chemotherapeutic agent may comprise the administration of more than one chemotherapeutic agent. For example, cisplatin may be administered in addition to Taxotere or other taxane, such as, for example, cabazitaxel.

EXAMPLES

The examples set forth below illustrate certain embodiments and do not limit the technology.

The following sections provide examples of methods of expressing an inducible chimeric signaling molecule in therapeutic cells, for example, T cells, and methods of using the transformed cells. Methods of expressing inducible polypeptides, use of the transformed or transfected cells, and assays are discussed, for example, in Spencer, D. M., et al., Science 262: 1019-1024 (1993); U.S. Pat. No. 7,404,950, entitled "Induced Activation in Dendritic Cells," issued Jul. 29, 2008; U.S. patent application Ser. No. 13/087,329, entitled "Methods for Treating Solid Tumors," filed Apr. 14, 2011; and U.S. patent application Ser. No. 13/112,739, entitled "Methods for Inducing Selective Apoptosis, filed May 20, 2011, which are hereby incorporated by reference herein in their entirety.

Example 1: Construction and Evaluation of Inducible Chimeric Signalling Molecule Expression Vectors Vector Construction and Confirmation of Expression Expression vectors suitable for use as a therapeutic agent are constructed that include a signaling molecule fused to a human FK506-binding protein (FKBP), such as, for example, FKBP12v36. These methods may also be used to express one or more costimulatory polypeptides. The inducible CSMs can be dimerized (or multimerized) using a small molecule pharmaceutical. Nucleic acids coding for the inducible CSMs are fused to nucleic acids coding for the ligand-binding domain, and inserted into the SFG retroviral or pLenti7.3 lentiviral vector, which also allows expression of the fluorescent marker, GFP.

The inducible CSM polypeptide includes 2, 3, or more, in certain embodiments, 2 or 3, FK506-binding proteins (FKBPs for example, FKBP12v36 variants, or FKBP12; GenBank AH002 818) that contains an F36V mutation) linked with a Gly-Ser-Gly-Gly-Gly-Ser linker (SEQ ID NO: 113) to the CSM sequence. The amino acid sequence of one or more of the FKBPs ($F_{v2}$) is codon-wobbled (e.g., the $3^{rd}$ nucleotide of each amino acid codon is altered by a silent mutation that maintained the originally encoded amino acid) to prevent homologous recombination when expressed in a retrovirus. All constructs are cloned into SFG or pLenti7.3.

293T cells are transfected with each of these constructs and 48 hours after transduction expression of the marker gene GFP or ΔCD19 is analyzed by flow cytometry. In addition to the level of GFP or ΔCD19 expression, the expressed gene products are also analyzed by western blot to confirm the expression of the inducible chimeric signaling molecule. For example, antibodies that bind to the costimulatory polypeptides may be used for the western blot.

Transfected 293T cells are resuspended in lysis buffer (50% Tris/Gly, 10% sodium dodecyl sulfate [SDS], 4% beta-mercaptoethanol, 10% glycerol, 12% water, 4% bromophenol blue at 0.5%) containing aprotinin, leupeptin, and phenylmethylsulfonyl fluoride (Boehringer, Ingelheim, Germany) and incubated for 30 minutes on ice. After a 30-minute centrifugation, supernatant is harvested, mixed 1:2 with Laemmli buffer (Bio-Rad, Hercules, Calif.), boiled and loaded on a 10% SDS-polyacrylamide gel. The membrane is probed with rabbit anti-costimulatory polypeptide immunoglobulin G (IgG; Affinity BioReagents, Golden, Colo.; 1:500 dilution) and with mouse anti-GFP IgG (Covance, Berkeley, Calif.; 1:25,000 dilution). Blots are then exposed to appropriate peroxidase-coupled secondary antibodies and protein expression is detected with enhanced chemiluminescence (ECL; Amersham, Arlington Heights, Ill.). The membrane is then stripped and reprobed with goat polyclonal antiactin (Santa Cruz Biotechnology; 1:500 dilution) to check equality of loading.

Evaluation of Inducible CSM Expression Constructs.

Cell Lines

The cancer cell lines LNCaP, PC3, DU145 and A549, and the human embryonic kidney cell line HEK-293T, are obtained from American Type Culture Collection (Rockville, Md.). Cells are maintained in complete IMDM (Sigma, St Louis, Mo.) containing 10% fetal bovine serum (Hyclone, Waltham, Mass.), and 2 mM L-glutamine in a humidified atmosphere containing 5% carbon dioxide ($CO_2$) at 37° C.

Transduced T cells and PHA blasts are maintained in Cellgenix DC (Cellgenix) media supplemented with 100 U/ml IL-2 (Cellgenix)

Activation of T Cells

Activation of T cells for expansion and transduction is performed using soluble αCD3 and αCD28 (Miltenyi Biotec, Auburn, Calif.). PBMCs are resuspended in Cellgenix DC media supplemented with 100 U/ml IL-2 (Cellgenix) at $1 \times 10^6$ cells/ml and stimulated with 0.2 µg/ml αCD3 and 0.5 µg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Retro Viral and Lentiviral Constructs

Inducible CSM (iCSM) and CAR-CD3.zeta constructs comprised of the codon-optimized single-chain variable fragments targeting PSMA, PSCA, MUC1 and Her2/Neu are synthesized by Blue Heron Bio (Bothell, Wash.). iCSM constructs consist of FKBP12v36 domains linked in-frame to costimulatory endodomains, including CD28, 4-1BB, and the CD3 zeta chain of the T cell receptor. CARs constructs are generated by cloning the scFv fragment in-frame with the human IgG1-Ch2Ch3 domain and with the CD3-zeta chain. Both iCSM and CAR-CD3.zeta constructs are subcloned into the SFG retroviral backbone or the pLenti7.3 lentiviral backbone (Invitrogen), which co-expresses emerald GFP. Evaluation of the stimulatory and co-stimulatory effect of the iCSM, and the cytotoxicity of the CAR-CD3.zeta is performed by single or co-transduction of T cells with retro- or lentivirus encoding these transgenes.

Retrovirus Transduction

For the transient production of retrovirus, 293T cells are transfected with iCSM constructs, along with plasmids encoding gag-pol and RD 114 envelope using GeneJuice transfection reagent (Novagen, Madison, Wis.). Virus is harvested 48 to 72 hours after transfection, snap frozen, and stored at ~80° C. until use. For the transient production of lentivirus, 293T cells are transfected with iCAR constructs along with the plasmids pLP1 (gag/pol), pLP2 (rev) and pLP/VSVG (VSVG env) using GeneJuice. Virus is harvested 48 to 72 hours after transfection, snap frozen, and stored at ~80° C. until use. For large-scale retrovirus production, a stable FLYRD 18-derived retroviral producer line is generated by multiple transductions with VSV-G pseudotyped transient retroviral supernatant. FLYRD18 cells with highest transgene expression are single-cell sorted, and the clone that produce the highest virus titer is expanded and used to produce virus for lymphocyte transduction. The transgene expression, function, and retroviral titer of this clone is maintained during continuous culture for more than 8 weeks. Non-tissue culture-treated 24-well plates are coated with 7 µg/ml Retronectin (Takara Bio, Otsu, Shiga, Japan) for 1 hour at 37° C. or overnight at 4° C. The wells are washed with phosphate-buffered saline (PBS) then coated with retroviral supernatant by incubating the plate with 1.5 ml of supernatant for 30 minutes at 37° C. Subsequently, T cell blasts are plated at $5 \times 10^5$ cells per well in viral supernatant supplemented with 100 U/ml IL-2. Transduction is performed over a 60-hour period. Following transduction, cells are harvested and phenotyped for CD19 or GFP expression by flow cytometry.

Cytotoxicity of iCSM/CAR-Transduced T Cells

The cytotoxic activity of each transduced T cell line is evaluated in a standard 4-hour $^{51}Cr$ release assay, as previously presented. T cells transduced with either iCSM, PSMA CAR-CD3.zeta or both iCSM and CAR viruses are compared against $Cr^{51}$-labeled target cells, including autologous phytohaemagglutinin (PHA) stimulated lymphocytes (PHA blasts), LNCaP, PC3 or DU145 and A549 cancer cell lines, and transgenic A549 expressing human PSMA (A549-PSMA). Target cells incubated in complete medium or 1% Triton X-100 (Sigma, St Louis, Mo.) are used to determine spontaneous and maximum $^{51}$Cr release, respectively. The mean percentage of specific lysis of triplicate wells was calculated as 100×(experimental release−spontaneous release)/(maximal release−spontaneous release). In addition to chromium-release assays, co-culture experiments with are performed. Here, the cell lines LNCaP, PC3, DU145, A549 and A549-PSMA are transduced to express fluorescent mOrange and used as target cells. mOrange-expressing tumor cells are co-cultured with non-transduced or CAR-modified T cells at a ratio of 1:10 tumor cells to T cells in the presence of IL-2 (50 U/ml) in complete media. After 24 hours, T cells bearing the iCAR are stimulated with 100 nM AP1903. After 72 hours, cells are collected, counted and labeled with CD3 to detect T cells and percentage of mOrange tumor cells is analyzed by flow cytometry (LSRII; BD).

Phenotyping and Activation Status of iCSM-Transduced T Cells

Cell surface phenotype of iCAR transduced T cells is investigated using the following monoclonal antibodies: CD3, CD4, CD8, CD19, CD25, CD27, CD28, CD44, CD45RA, CD45RO, CD62L, CD80, CD83, CD86, CD127, CD134, CD137, HLA-ABC and HLA-DR. Phenotyping is performed with and without 10-100 nM AP1903 as a iCSM stimulant. Appropriate matched isotype controls are used in each experiment and cells are analyzed with a LSRII flow cytometer (BD). CAR expression was assessed using anti-F(ab')2 (Jackson ImmunoResearch Laboratories, West Grove, Pa.).

Analysis of Cytokine Production of iCSM-Transduced T Cells

The concentration of interferon-γ (IFN-γ), IL-2, IL-4, IL-5, IL-10, and tumor necrosis factor-α (TNFα) in T cell culture supernatants before and after (24 hours) 100 nM AP1903 stimulation is measured using the Human Th1/Th2 cytokine cytometric Bead Array (BD Pharmingen). Induced cytokine production in the culture supernatants is validated by enzyme-linked immunosorbent assay (ELISA; R&D Systems, Minneapolis, Minn.) according to the instructions of the manufacturer.

Proliferation of iCSM-Transduced T Cells

The proliferative effect of AP1903-induced signaling through iCSM is evaluated by measuring cell growth of transduced and non-transduced T cells following exposure to AP1903. T cells are labeled with 10 µM carboxyfluorescein diacetate, succinimidyl ester (CFSE) for 10 minutes at 37° C. After incubation, cells are washed in PBS and then resuspended in Cellgenix DC media. 1×10$^6$ CFSE-labeled iCSM-modified or non-transduced T cells are subsequently cultured in Cellgenix DC media alone, or stimulated with 100 nM AP1903. After 5 days, cells are harvested and labeled with CD3-PerCP.Cy5.5 and CD19-PE and analyzed by flow cytometry for CFSE dilution.

To evaluate whether soluble immunoglobulins affect the proliferation and expansion of CARP T lymphocytes, cells are cultured at 1×10$^5$ cells/well either with serial dilution of human plasma obtained from healthy donors or serial dilution of purified human immunoglobulins (Jackson ImmunoResearch) without any addition of exogenous cytokines. After 72 hours, the cells are pulsed with 1 µCi (0.037 MBq) methyl-$^3$[H]thymidine (Amersham Pharmacia Biotech, Piscataway, N.J.) and cultured for additional 15 hours. The cells were then harvested onto filters and dried, and counts per minute are measured in a β-scintillation counter (TriCarb 2500 TR; Packard BioScience, Meridien, Conn.). The experiments are performed in triplicate. In other experiments, control and CARP T lymphocytes are cultured either with media alone or with media in which serial dilution of plasma or purified immunoglobulins are added every second day. Cells are then counted every third day using trypan blue exclusion.

In Vivo Experiments

Non-obese diabetic severe combined immunodeficient (NOD/SCID) mice, 6 to 8 weeks of age, are irradiated (250 rad) and injected subcutaneously in the right flank with 10×10$^6$ to 15×10$^6$ LNCaP tumor cells resuspended in Matrigel (BD Bioscience). Two weeks later mice bearing tumors that are approximately 0.5 cm in diameter were injected into the tail vein with either non-transduced or iCSM/CAR-transduced T cells (total 15×10$^6$). The mice are randomly segregated in 2 groups: 1 group receives CID (50-125 µg AP1903, intraperitoneally, twice weekly) and 1 group receives carrier only (16.7% propanediol, 22.5% PEG400, and 1.25% Tween 80, intraperitoneally, twice weekly) to expand T cells. Mice are evaluated for tumor growth by caliper measurement for 21 days. Peripheral blood samples are taken by retro-orbital eye bleeding on days 7, 14 and 21 to measure the persistence and expansion of iCSM or control T cells using flow cytometric analysis for human CD3/human CD19 expressing T cells.

Evaluation of iCSM-Transduced Tcell Characteristics In Vivo

To ensure that expression of inducible CSMs do not alter T-cell characteristics, the phenotype, antigen-specificity, proliferative potential, and function of nontransduced or nonfunctional inducible CARs (PSMA CAR-CD3.zeta only) are compared with that of iCSM/CAR-transduced T cells. The numbers of CD4$^+$, CD8$^+$, CD56$^+$, and TCR α/β$^+$ cells in transduced and non-transduced cells are compared, as is the production production of cytokines including IFN-γ, TNFα, IL-10, IL-4, IL-5, and IL-2. The growth characteristics of exponentially growing CTLs, and dependence on antigen and IL-2 for proliferation are evaluated, as is phenotypic and secretion data of type $T_H1$ and $T_H2$ cytokines upon antigen stimulation.

Example 2: Using the Inducible CSM in Human Cells for Therapy

Presented in this example are expression constructs and methods of using the expression constructs in human cells.

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at 1×10$^6$ cells/ml and stimulated with 0.2 µg/ml αCD3 and 0.5 µg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Plasmid and Retrovirus

The SFG plasmid consists of inducible CSM linked, via a cleavable 2A-like sequence, to truncated human CD19. The inducible CSM consists of a human FK506-binding protein (FKBP12; GenBank AH002 818) with an F36V mutation, connected via a Ser-Gly-Gly-Gly-Ser linker (SEQ ID NO: 114) to a human CSM. The F36V mutation increases the binding affinity of FKBP12 to the synthetic homodimerizer, AP20187 or AP1903. The 2A-like sequence encodes a 20 amino acid peptide from *Thosea asigna* insect virus, which mediates >95% cleavage between a glycine and terminal proline residue, resulting in 19 extra amino acids in the C terminus of iCSM, and one extra proline residue in the N terminus of CD19. CD19 consists of full-length CD19 (GenBank NM 001770) truncated at amino acid 333 (TDP-TRRF) (SEQ ID NO: 115), which shortens the intracytoplasmic domain from 242 to 19 amino acids, and removes all conserved tyrosine residues that are potential sites for phosphorylation.

A stable PG13-based clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

Retro Viral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 μg/ml and anti-CD28 0.2 μg/ml or 10 ml of fibronectin 7 μg/ml at 4° C. overnight. Fluorinated ethylene propylene bags corona-treated for increased cell adherence (2 PF-0072AC, American Fluoroseal Corporation, Gaithersburg, Md.) are also used. PBMCs are seeded in anti-CD3, anti-CD28-coated flasks at $1 \times 10^6$ cells/ml in media supplemented with 100 U/ml IL-2. For retroviral transduction, retronectin-coated flasks or bags are loaded once with 10 ml of retrovirus-containing supernatant for 2 to 3 hours. Activated T cells are seeded at $1 \times 10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about $5 \times 10^5$ cells/ml to $8 \times 10^5$ cells/ml.

CD19 Immunomagnetic Selection

Immunomagnetic selection for CD19 may be performed, in one example, performed 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CliniMacs Plus automated selection device in large scale experiments. CD19-selected cells are expanded for a further 4 days and cryopreserved on day 8 post transduction. These cells are referred to as "gene-modified cells".

Immunophenotyping and Pentamer Analysis

Flow cytometric analysis (FACSCalibur and CellQuest software; Becton Dickinson) is performed using the following antibodies: CD3, CD4, CD8, CD19, CD25, CD27, CD28, CD45RA, CD45RO, CD56 and CD62L. CD19-PE (Clone 4G7; Becton Dickinson) is found to give optimum staining and was used in all subsequent analysis. A non-transduced control is used to set the negative gate for CD19. CAR expression is assessed using anti-F(ab')2 (Jackson ImmunoResearch Laboratories, West Grove, Pa.).

Statistical Analysis

Paired, 2-tailed Student's t test is used to determine the statistical significance of differences between samples. All data are represented as mean±1 standard deviation.

Example 3: Measurement of AP1903-Dependent T Cell Activation

Aim: To transduce primary T cells with a retroviral vector encoding signaling molecules linked to two FKBPv36 molecules to enable AP1903 activation of the T cells. In this experiment, production of cytokines in response to dimerization was measured using a multiplex cytokine bead array.

Methods:

Design and Cloning of Inducible T Cell Molecules:

1. Two SFG-based retroviral vectors were constructed by Gibson cloning, where PCR products were amplified from pAd1127-02-iMC and inserted into the pBP0320-SFG-Myr.LFv1.Fv2L2A.ΔCD19 construct in place of the LFv1.Fv2L DNA fragment.
   a. In the first vector, the PCR product amplified was Fv'Fv, or where only the FKBPv36 fragments were inserted into the retroviral backbone, replacing LFv1.Fv2L at the XhoI and SalI sites. This vector is called pBP0171-SFG-Myr.Fv'.Fv.2A.ΔCD19, and is the control vector which lacks any T cell signaling molecules.
   b. In the second vector, the PCR product amplified was MyD88/CD40.Fv'.Fv (or iMCnoE). This was inserted into the pBP0320 plasmid at the XhoI and SalI restriction sites in place of the LFv1.Fv2L DNA sequence. This vector is called pBP0172-SFG-Myr.iMCnoE.2A.ΔCD19. The "noE" suffix indicates that this iMC DNA does not encode an epitope tag.

Production of Retrovirus:

2. Retrovirus was produced by a transient transfection method, where HEK293T cells were transfected with the following plasmids:
   a. SFG retroviral plasmids (pBP0171 or pBP0172; RV-171 or RV-172, respectively)
   b. Retroviral envelope plasmid (RD114)
   c. Gag/pol plasmid (pEQ-PAM-E)

3. At 48 and 72 hours, supernatant from the transfected cells containing replication defective retrovirus was collected and snap frozen in dry ice/ethanol and stored at −80° C. until T cell transduction.

4. To transduce primary T cells, PBMCs from healthy donors were activated with anti-CD3 and anti-CD28 antibodies in T cell growth media supplemented with 100 U/ml IL-2. After 3 days, T cells were activated and harvested and ready for retroviral transduction. To transduce the T cells, non-tissue culture-treated plates were first coated with Retronectin overnight at 4° C. The Retronectin was then removed, and the plates washed with PBS. Retroviral supernatants were then used to coat the Retronectin plate. Activated T cells were then added to the wells and the plate was centrifuged to facilitate viral particle binding and transduction. After 48 hours, the T cells are harvested and analyzed by flow cytometry for CD3 and CD19 co-expression to determine viral transduction efficiency.

Analysis of AP1903-Induced T Cell Activation by Cytokine Production:

5. To assess AP1903-dependent T cell activation of T cells, $1 \times 10^5$ non-transduced (NT) or T cells transduced with the control retrovirus (RV-171) or the retrovirus containing iMC(RV-172) were plated in triplicate in 96-well plates and cultured at 37° C. 5% $CO_2$ with media alone, or media containing 10 nM AP1903.

6. After 24 hours, the cells were gently mixed and the plate was centrifuged. Supernatant was then collected and plated into a Bio-Plex Human Cytokine/Chemokine 27-plex plate, which measures the following cytokines and chemokines:
   a. Basic-FGF, G-CSF, GM-CSF, IFN-gamma, IL-1Ra, IL-1beta, IL-2, IL-4, IL-5, IL-6, IL-8, IL-7, IL-8, IL-9, IL-10, IL-12p70, IL-13, IL-15, IL-17RA, eotaxin, IP10, MCP-1, MIP-1alpha, MIP-1beta, PDGF-bb, RANTES, TNF-alpha and VEGF.
   b. The cytokines and chemokines in the supernatants were subsequently measured and compared to standards in the plate using a Bio-Plex MAGPIX Multiplex Reader.

Results:

Transduction Efficiency:

1. T cells from two healthy donors were transduced with retrovirus and after 48 hours, the efficiency as determined by flow cytometry for $CD3^+CD19^+$ co-expression was as follows:
   a. Donor 063
      i. NT=6.54%
      ii. RV-171=73.9%
      iii. RV-172=54.6%
   b. Donor 707
      i. NT=2.16%
      ii. RV-171=85.2%
      iii. RV-172=73.6%

2. Transduction was quite high for both vectors and donors indicating that they were not toxic to HEK293T cells and that the viral titers were good.

Cytokine/Chemokine Production

3. Analysis of cytokine and chemokine secretion showed remarkable dependency on AP1903 dimerization. The following T cell-produced cytokines and chemokines showed induction over a 24-hour period, but were absent from T cells transduced with the control vector or non-transduced T cells:
   a. GM-CSF, IFN-gamma, IL-13, IL-4, IL-5, IL-6, IL-8, IL-1beta, IL-12p70, IP10, MIP-1alpha, MIP-1beta, RANTES, and TNF-alpha 4. Additionally, other cytokines and chemokines did not appear to be induced by AP1903 activation of iMC. These include the following:
   a. Basic-FGF, G-CSF, IL-1Ra, IL-2, IL-7, IL-9, IL-10, IL-15, IL-17RA, eotaxin, MCP-1, PDGF-bb and VEGF.

Certain results are also depicted in FIGS. 7-15. NT=non-transduced activated T cells RV0171=SFG-Myr.Fv'.Fv.2A.ΔCD19; RV0172=SFG=Myr.MyD88/ CD40.Fv'.Fv.2A. ΔCD19.

T cells were stimulated with 10 nM AP1903 for 24 hours then supernatants were assayed for cytokine levels.

Example 4: Measurement of AP1903-Dependent T Cell Cytotoxicity

Aim: To transduce primary T cells with a retroviral vector encoding signaling molecules linked to two FKBPv36 molecules to enable AP1903 activation of the T cells. In this experiment, two aspects of AP1903 activation were examined. First, if T cells were in close proximity to tumor cells, would their activation induce tumor cell killing? Second, if T cells were activated via AP1903, would they proliferate?

Methods:

Design and Cloning of Inducible T Cell Molecules and Production of Retrovirus

1. The methods are essentially the same as those discussed in the above Example 4. The same cells were used for this assay.

Generation of GFP-Marked CAPAN-1 (Pancreatic Adenocarcinoma) Cell Line:

2. CAPAN-1 was purchased from ATCC. Subsequently, the cell line was gene-modified by transfection with the pBP0168-pcDNA3.1-EGFPluc plasmid, which contains the gene for the EGFP/firefly luciferase fusion protein, as well as the neomycin-resistance gene, allowing stably transfected cells to be selected over time by culturing with G418 antibiotic. Following culture, clones with high GFP expression were selected and subcultured until a cell line with >95% GFP was obtained.

Co-Culture of iMC-Enabled T Cells with CAPAN-1 Tumor Cells:

3. Non-transduced T cells or cells transduced with RV-171 (control vector) or RV-172 (iMC vector) were cultured at a 5:1 ratio of T cells to tumor cells in media supplemented with 50 U/ml IL-2, and either with or without 10 nM AP1903. Co-cultures were then incubated at 37° C. and 5% $CO_2$ for 72 hours. Cultures were subsequently analyzed for the presence of GFP tumor cells by fluorescent microscopy and by harvesting the cultures with 0.25% trypsin/EDTA and measuring the frequency of $GFP^+CD3^-$ tumor cells in the culture by flow cytometry.

Results:

4. Upon inspection of the co-culture wells, it was evident that in both donors, T cells transduced with RV-172 (iMC-containing vector) that were stimulated with AP1903 were proliferating, as evident by large T cell blast colonies. In addition, by fluorescent microscopy, co-cultures containing RV-172-transduced T cells receiving AP1903 showed very few viable $GFP^+$ tumor cells. Following these initial observations, T cells and tumor cells were harvested and analyzed by flow cytometry to determine the frequency of remaining CAPAN-1 $GFP^+$ tumor cells.

5. As observed by microscopy, flow cytometry showed a clear effect of AP1903 in co-cultures containing AP1903-treated, iMC-transduced (RV-172) T cells. The reduction of $GFP^+$ tumor cells only occurred in this condition, but not with T cells transduced with the control vector, and to a lesser extent with T cells transduced with RV-172 that did not receive dimerizer.

6. Together, these data suggests that activation of iMC in T cells is capable of inducing T cell killing and induce proliferation of AP1903-treated T cells. Collectively, with our observations regarding cytokine/chemokine production, these data indicate that iMC can be activated in T cells and that T cells retain and increase their effector functions upon iMC dimerization.

Certain results are also depicted in FIGS. 16-19.

Example 5: Activation of T Cells Ex Vivo and Administration to a Human Subject

Presented in this example are methods of using the modified T cells for human therapy. In this example, the costimulatory polypeptide cytoplasmic regions are derived from CD40 and MyD88.

These methods may be adapted for other cells, such as, for example NK and NKT cells, as well as tumor-infiltrating lymphocytes, and may also be adapted for inducible CSMs that comprise other costimulatory polypeptide cytoplasmic regions as discussed herein.

Materials and Methods
Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at $1\times10^6$ cells/ml and stimulated with 0.2 µg/ml αCD3 and 0.5 µg/ml αCD28 soluble antibody. Cells are then cultured at 37° C., 5% $CO_2$ for 4 days. On day four, 1 ml of fresh media containing IL-2 is added. On day 7, cells are harvested and resuspended in Cellgenix DC media for transduction.

Plasmid and Retrovirus

The SFG plasmid consists of inducible CSM linked, via a cleavable 2A-like sequence, to truncated human CD19. The inducible CSM consists of a human FK506-binding protein (FKBP12; GenBank AH002 818) with an F36V mutation, connected via a Ser-Gly-Gly-Gly-Ser linker (SEQ ID NO: 114) to a human CSM. The F36V mutation increases the binding affinity of FKBP12 to the synthetic homodimerizer, AP20187 or AP1903. The 2A-like sequence encodes an 20 amino acid peptide from *Thosea asigna* insect virus, which mediates >99% cleavage between a glycine and terminal proline residue, resulting in 19 extra amino acids in the C terminus of the inducible CSM, and one extra proline residue in the N terminus of CD19. CD19 consists of full-length CD19 (GenBank NM 001770) truncated at amino acid 333 (TDPTRRF) (SEQ ID NO: 115), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

Retroviral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 µg/ml and anti-CD28 0.2 µg/ml or 10 ml of fibronectin 7 µg/ml at 4° C. overnight. Fluorinated ethylene propylene bags corona-treated for increased cell adherence (2 PF-0072AC, American Fluoroseal Corporation, Gaithersburg, Md.) is also used. PBMCs are seeded in anti-CD3, anti-CD28-coated flasks at $1\times10^6$ cells/ml in media supplemented with 100 U/ml IL-2. For retroviral transduction, retronectin-coated flasks or bags are loaded once with 10 ml of retrovirus-containing supernatant for 2 to 3 hours. Activated T cells are seeded at $1\times10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about $5\times10^5$ cells/ml to $8\times10^5$ cells/ml.

CD19 Immunomagnetic Selection

If necessary, immunomagnetic selection for CD19 is performed 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CliniMacs Plus automated selection device in large scale experiments.

CD19-selected cells are expanded for a further 4 days and cryopreserved on day 8 post transduction. These cells are referred to as "gene-modified cells."

Example 6: Treatment of a Leukemia Patient

The present example of the treatment of a leukemia patient having advanced treatment refractory leukemia, using the methods of the present application, may also be applied to other conditions or diseases, such as, for example, other hyperproliferative diseases or solid tumors. The methods may be used essentially as discussed, with the understanding that the single chain variable fragment may vary according to the target antigen.

T cells are transduced with a nucleic acid comprising a polynucleotide coding for an inducible chimeric signaling molecule. The T cells are also transduced with a nucleic acid comprising a polynucleotide coding for a chimeric antigen receptor. Examples of the inducible CSM include, but are not limited to, those depicted in FIG. 4, comprising a CD28 polypeptide cytoplasmic stimulating region and a 4-1BB polypeptide cytoplasmic signaling regions. The inducible CSM may also include a CD3 zeta polypeptide. The chimeric antigen receptor comprises a single chain variable fragment that recognizes CD19.

The patient undergoes lymphodepletive conditioning, followed by administration of the transduced CD19-targeted T cells. The T cells may be autologous, allogeneic, or non-allogeneic. Following administration of the T cells, the ligand inducer is administered to the patient, in order to expand the CD19-targeted T cells by inducing the chimeric signaling molecule. The dose may be provided, for example, daily, twice a week, or weekly. The level of tumor cells is monitored, and the ligand inducer, for example, AP1903, dosing schedule is adjusted based on the tumor cell load. Because of the concern that an unregulated, too rapid rate of T cell expansion, activation, and tumor cell killing may lead to a more severe cytoking storm that unnecessarily harms the patient, the dosing schedule is designed to achieve a complete recovery at a rate that limits toxicity and does not cause extensive harm to the patient, for example, keeping the patient out of the intensive care unit at a hospital. Once the patient achieves a complete recovery and remains disease free for a certain length of time to be determined, for example, one month, three months, six months, the dosing of AP1903 is stopped. Following treatment, in the absence of the ligand inducer, the number of CD19-targeted T cells is reduced. There may be a low level of basal signaling, allowing a small number of the quiescent CD19-targeted T cells to survive. Without the ligand inducer, these cells remain inactive and allow normal B cells to recover. If at any time in the future, the patient develops a recurrence of leukemia, dosing of the ligand inducer, AP1903, will resume, reactivating the CD19-targeted T cells and leading to re-induction of a complete response in the patient. This additional dosing may be repeated more than once, in the event of multiple recurrences.

Example 7: Measurement of iMC Activity in CAR Transduced T Cells

Aim: To transduce primary T cells with a retroviral vector encoding signaling molecules linked to two FKBPv36 molecules to allow AP1903 activation of the T cells. The experiment is designed to examine whether the inducible costimulatory molecule comprising the truncated MyD88 and CD40 polypeptides, improve killing of the GFP-modified CAPAN-1 (pancreatic adenocarcinoma) cells by T cells also transduced with a CAR recognizing prostate stem cell antigen (PSCA), which is highly expressed on CAPAN-1 tumor cells.

Methods:

Design and Cloning of Inducible T Cell Molecules:

1. Transduction of T cells is performed with RV-172 (SFG-Myr.MyD88/CD40.Fv.Fv'0.2A.ΔCD19) and RV-89 (SFG.PSCAscFv.CH2CH3.CD28.zeta). The scFv targets PSCA using the scFv from the humanized monoclonal antibody, 1G8 (derived from humanized anti-PSCA in US2012077962 A1). This is linked to the CH2CH3 region of human IgG1, which in turn is linked to CD28 which contains both the transmembrane and cytoplasmic portion of the molecule. CD28 is linked to the cytoplasmic portion of CD3 zeta.

Production of Retrovirus:

2. Essentially the same as in the previous example.

Generation of GFP-marked CAPAN-1 (pancreatic adenocarcinoma) cell line:

3. CAPAN-1 is purchased from ATCC. Subsequently, the cell line is gene-modified by transfection with the pBP0168-pcDNA3.1-EGFPluc which contains the gene for the EGFP/firefly luciferin fusion protein, as well as the neomycin resistance gene allowing stably transfected cells to be selected over time by culturing with G418 antibiotic. Following culture, clones with high GFP expression are selected and subcultured until a cell line with >95% GFP is obtained.

Co-Culture of iMC-Enabled T Cells with CAPAN-1 Tumor Cells:

4. Non-transduced or T cells co-transduced with RV-89 (PSCA CAR) and RV-172 (iMC vector) are cultured at a 5:1 ratio of T cells to tumor cells in media supplemented with 50 U/ml IL-2, and either with or without 10 nM AP1903. Co-cultures are then incubated at 37° C. and 5% $CO_2$ for 72 hours. Cultures are subsequently analyzed for the presence of $GFP^+$ tumor cells by fluorescent microscopy and by harvesting the cultures with 0.25% trypsin/EDTA and measuring the frequency of $GFP^+CD3^-$ tumor cells in the culture by flow cytometry.

Results:

1. The cultures are examined by fluorescent microscopy to assess an improvement in tumor cell killing in the wells that contain the inducible costimulatory molecule- and chimeric antigen receptor-transduced T cells and that received AP1903.

2. Flow cytometry is used to analyze $GFP^+$ cells in the cultures following trypsinization to determine whether AP1903 contributes to a reduction in tumor cell number in this short culture period (72 hours). The time period for the culture may be extended to approximately 5 days. The flow cytometry plots may show the reduction in $GFP^+$ cells in wells, at a 5:1 ratio, that were transduced with both virus and receive AP1903.

3. The remaining viable CAPAN-1-GFP cells are normalized to the conditions of NT T cells without AP1903 to show the effect of iMC activation on tumor cell killing.

Example 8: Examples of Particular Nucleic Acid and Amino Acid Sequences

The following sequences provide an example of the nucleotide and amino acid sequences used, in order, for an inducible chimeric signaling molecule (CSM) sequences.

SEQ ID NO: 1, Myristolation nt
ATGGGGAGTAGCAAGAGCAAGCCTAAGGACCCCAGCCAGCGC

SEQ ID NO: 2, Myristolation aa
MGSSKSKPKDPSQR

SEQ ID NO: 3, Linker sequence (between Myr and Fv1) nt
CTCGAGTCTGGCGGTGGATCCGGAG SEQ ID NO: 4, Linker sequence (between Myr and $F_v1$) aa
LESGGGSG SEQ ID NO: 5, FKBPv36 ($F_v1$) nt
GGCGTTCAAGTAGAAACAATCAGCCCAGGAGACGGAAGGACTTTCCCCAA

ACGAGGCCAAACATGCGTAGTTCATTATACTGGGATGCTCGAAGATGGAA

AAAAAGTAGATAGTAGTAGAGACCGAAACAAACCATTTAAATTTATGTTG

GGAAAACAAGAAGTAATAAGGGGCTGGGAAGAAGGTGTAGCACAAATGTC

TGTTGGCCAGCGCGCAAAACTCACAATTTCTCCTGATTATGCTTACGGAG

CTACCGGCCACCCCGGCATCATACCCCCTCATGCCACACTGGTGTTTGAC

GTCGAATTGCTCAAACTGGAA

SEQ ID NO: 6, FKBPv36 ($F_v1$) aa
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

SEQ ID NO: 7, Linker sequence (between $F_v1$ and $F_v2$) nt
GTCGAG

SEQ ID NO: 8, Linker sequence (between $F_v1$ and $F_v2$) aa
VE

SEQ ID NO: 9, FKBPv36 ($F_v2$) nt
GGAGTGCAGGTGGAGACGATTAGTCCTGGGGATGGGAGAACCTTTCCAA

AGCGCGGTCAGACCTGTGTTGTCCACTACACCGGTATGCTGGAGGACGG

GAAGAAGGTGGACTCTTCACGCGATCGCAATAAGCCTTTCAAGTTCATG

CTCGGCAAGCAGGAGGTGATCCGGGGTGGGAGGAGGGCGTGGCTCAGA

TGTCGGTCGGGCAACGAGCGAAGCTTACCATCTCACCCGACTACGCGTA

TGGGGCAACGGGGCATCCGGGAATTATCCCTCCCCACGCTACGCTCGTA

TTCGATGTGGAGCTCTTGAAGCTTGAG

SEQ ID NO: 10, FKBPv36 (F$_v$2) aa
GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE

SEQ ID NO: 11, Linker sequence (between F$_v$2 and CD28) nt
TCTGGCGGTGGATCCGGAGTCGAG SEQ ID NO: 12, Linker sequence (between Myr and CD28) aa
SGGGSGVE SEQ ID NO: 13, CD28 nt
TTCTGGGTACTGGTTGTAGTCGGTGGCGTACTTGCTTGTTATTCTCTTCT

TGTTACCGTAGCCTTCATTATATTCTGGGTCCGATCAAAGCGCTCAAGAC

TCCTCCATTCCGATTATATGAACATGACACCTCGCCGACCTGGTCCTACA

CGCAAACATTATCAACCCTACGCACCCCCCCGAGACTTCGCTGCTTATCG

ATCC

SEQ ID NO: 14, CD28 aa
FWVLVVVGGVLACYSLLVTVAFIIFWVRSKRSRLLHSDYMNMTPRRPGPT

RKHYQPYAPPRDFAAYRS

SEQ ID NO: 15, Linker sequence (between CD28 and 4-1BB) nt
GGATCC

SEQ ID NO: 16, Linker sequence (between CD28 and 4-1BB) aa
GS

SEQ ID NO: 17, 4-1BB nt
AGTGTAGTTAAAAGAGGAAGAAAAAAGTTGCTGTATATATTTAAACAACC

ATTTATGAGACCAGTGCAAACCACCCAAGAAGAAGACGGATGTTCATGCA

GATTCCCAGAAGAAGAAGAAGGAGGATGTGAATTG

SEQ ID NO: 18, 4-1BB aa
SVVKRGRKKLLYIFKQPFMRPVQTTQEEDGCSCRFPEEEEGGCEL

SEQ ID NO: 19, Linker sequence (between 4-1BB and CD3 zeta) nt
ACGCGT

SEQ ID NO: 20, Linker sequence (between 4-1BB and CD3 zeta) aa
TR

SEQ ID NO: 21, CD3 zeta nt
CGGGTCAAATTCAGCCGGAGTGCTGACGCCCCAGCATACCAACAGGGACA

AAACCAACTCTACAACGAGCTCAACCTGGGTAGACGCGAGGAGTACGACG

TTCTGGATAAGAGGCGGGGCCGGGACCCAGAGATGGGGGGCAAACCTCAG

CGGCGGAAGAACCCGCAGGAGGGTCTTTATAACGAGCTCCAGAAGGACAA

GATGGCGGAAGCCTATTCAGAAATTGGGATGAAAGGCGAGAGACGCAGGG

GAAAAGGTCACGATGGTCTGTATCAAGGACTGTCAACCGCCACCAAAGAC

ACTTACGATGCGCTCCACATGCAGGCCCTCCCTCCCCGC

SEQ ID NO: 22, CD3 zeta aa
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

SEQ ID NO: 23, Linker sequence (between CD3 zeta and Furin) nt
GTCGAC

SEQ ID NO: 24, Linker sequence (between CD3 zeta and Furin) aa
VD

SEQ ID NO: 25, Furin nt
CGCGCAAAGCGT

SEQ ID NO: 26, Furin aa
RAKR

SEQ ID NO: 27, V5 epitope tag nt
GGAAAACCTATACCTAATCCATTGCTGGGCTTAGACTCAACA

SEQ ID NO: 28, V5 epitope tag aa
GKPIPNPLLGLDST

SEQ ID NO: 29, Linker sequence (between V5 and P2A) nt
GGCAGCGGAAGC

SEQ ID NO: 30, Linker sequence (between V5 and P2A) aa
GSGS

SEQ ID NO: 31, Porcine teschovirus-1 2A (P2A) nt
GCAACGAATTTTTCCCTGCTGAAACAGGCAGGGGACGTAGAGGAAAATCC

TGGTCCT

SEQ ID NO: 32, Porcine teschovirus-1 2A (P2A) aa
ATNFSLLKQAGDVEENPGP

SEQ ID NO: 33, Linker sequence (between P2A and ΔCD19) nt
ACGCGT

SEQ ID NO: 34, Linker sequence (between P2A and ΔCD19) aa
TR

SEQ ID NO: 35, ΔCD19 nt
ATGCCCCCTCCTAGACTGCTGTTTTTCCTGCTCTTTCTCACCCCAATGGA

AGTTAGACCTGAGGAACCACTGGTCGTTAAAGTGGAAGAAGGTGATAATG

CTGTCCTCCAATGCCTTAAAGGGACCAGCGACGGACCAACGCAGCAACTG

ACTTGGAGCCGGGAGTCCCCTCTCAAGCCGTTTCTCAAGCTGTCACTTGG

CCTGCCAGGTCTTGGTATTCACATGCGCCCCCTTGCCATTTGGCTCTTCA

TATTCAATGTGTCTCAACAAATGGGTGGATTCTACCTTTGCCAGCCCGGC

CCCCCTTCTGAGAAAGCTTGGCAGCCTGGATGGACCGTCAATGTTGAAGG

CTCCGGTGAGCTGTTTAGATGGAATGTGAGCGACCTTGGCGGACTCGGTT

GCGGACTGAAAAATAGGAGCTCTGAAGGACCCTCTTCTCCCTCCGGTAAG

TTGATGTCACCTAAGCTGTACGTGTGGGCCAAGGACCGCCCCGAAATCTG

GGAGGGCGAGCCTCCATGCCTGCCGCCTCGCGATTCACTGAACCAGTCTC

TGTCCCAGGATCTCACTATGGCGCCCGGATCTACTCTTTGGCTGTCTTGC

GGCGTTCCCCCAGATAGCGTGTCAAGAGGACCTCTGAGCTGGACCCACGT

ACACCCTAAGGGCCCTAAGAGCTTGTTGAGCCTGGAACTGAAGGACGACA

```
GACCCGCACGCGATATGTGGGTAATGGAGACCGGCCTTCTGCTCCCTCGC

GCTACCGCACAGGATGCAGGGAAATACTACTGTCATAGAGGGAATCTGAC

TATGAGCTTTCATCTCGAAATTACAGCACGGCCCGTTCTTTGGCATTGGC

TCCTCCGGACTGGAGGCTGGAAGGTGTCTGCCGTAACACTCGCTTACTTG

ATTTTTTGCCTGTGTAGCCTGGTTGGGATCCTGCATCTTCAGCGAGCCCT

TGTATTGCGCCGAAAAGAAAACGAATGACTGACCCTACACGACGATTCT

GA
```

SEQ ID NO: 36, ΔCD19 aa
```
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRF
```

The following is an example of the nucleotide and amino acid sequences for a chimeric antigen receptor (CAR) sequences (in order, without scFv fragments)

SEQ ID NO: 37, Signal peptide nt
```
ATGGAGTTTGGGCTGTCATGGCTGTTCCTCGTGGCCATTCTCAAAGGGGT

CCAGTGTTCTCGC
```

SEQ ID NO: 38, Signal peptide aa
MGFGLSWLFLVAILKGVQCSR

SEQ ID NO: 39, Flexible linker sequence nt
GGGGGAGGAGGTTCTGGAGGCGGCGGGAGCGGAGGAGGAGGCAGC SEQ ID NO: 40, Flexible linker sequence aa
GGGGSGGGGSGGGGS SEQ ID NO: 41, Linker sequence (between scFv and CH2CH3) nt
GGATCC SEQ ID NO: 42, Linker sequence (between scFv and CH2CH3) aa
GS SEQ ID NO: 43, IgG1 Ch2Ch3 nt
```
GATCCAGCCGAACCCAAATCCCCCGATAAAACACATACTTGCCCCCCTTG

TCCCGCACCAGAATTGCTTGGCGGACCTTCCGTTTTTCTTTTTCCCCCA

AACCTAAAGATACCCTGATGATTTCCCGAACCCCTGAAGTTACGTGCGTA

GTCGTAGATGTGTCTCACGAAGATCCAGAAGTAAAATTTAACTGGTACGT

AGATGGAGTCGAAGTTCACAACGCAAAGACGAAGCCCCGAGAAGAACAAT

ATAATTCCACATACCGAGTAGTTAGCGTTCTCACCGTACTGCATCAGGAC

TGGCTTAACGGCAAAGAATATAAATGTAAGGTCTCAAACAAAGCACTCCC

AGCCCCTATCGAAAAGACTATCTCCAAAGCTAAAGGACAACCCCGCGAAC

CCCAGGTCTATACACTTCCCCCCCTCACGCGATGAACTCACTAAAAATCAG

GTTTCCCTTACTTGTCTTGTCAAAGGCTTCTACCCTAGCGATATCGCAGT

CGAATGGGAATCCAATGGCCAGCCCGAAAACAACTATAAAACAACCCCAC

CTGTCCTCGATTCAGATGGCTCATTCTTTCTATTCCAAACTGACTGTA
```

```
GACAAATCCCGATGGCAACAAGGTAACGTGTTCTCTTGCTCAGTCATGCA

TGAAGCGCTTCATAACCATTACACACAAAAATCTCTCTCACTGTCTCCCG

GAAAGAAGGACCCC
```

SEQ ID NO: 44, IgG1 CH2CH3 aa
```
DPAEPKSPDKTHTCPPCPAPELLGGPSVFLFPPKPKDTLMISRTPEVTCV

VVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTV

DKSRWQQGNVFSCSVMHEALHNHYTQKSLSLSPGKKDP
```

SEQ ID NO: 45, Linker sequence (between scFv and CH2CH3) nt
CTCGAG

SEQ ID NO: 46, Linker sequence (between scFv and CH2CH3) aa
LE

SEQ ID NO: 47, CD3 zeta transmembrane nt
```
AAACTGTGTTACCTCCTCGATGGCATCCTCTTTATTTATGGCGTGATTCT

GACCGCATTGTTTCTCCGAGTAAAATTCTCTAGATCCGCAGACGCTCCCG

CATATCAGCAAGGACAAAATCAGCTTTATAACGAACTTAACCTCGGCAGA

CGCGAAGAATACGATGTACTGGACAAGAGAAGAGGAAGAGATCCCGAAAT

GGGCGGAAAACCCCAGAAGAAAAGAATCCCCAAGAAGGTCTTTATAACG

AACTGCAGAAAGATAAAATGGCCGAAGCGTACAGTGAAATTGGTATGAAA

GGAGAAAGAAGACGCGGAAAAGGACATGACGGACTCTACCAAGGACTCTC

AACTGCTACTAAAGATACATACGACGCCCTTCATATGCAAGCCCTCCCCC

CGAGATAA
```

SEQ ID NO: 48, CD3 zeta transmembrane aa
```
KLCYLLDGILFIYGVILTALFLRVKFSRSADAPAYQQGQNQLYNELNLGR

REEYDVLDKRRGRDPEMGGKPQRRKNPQEGLYNELQKDKMAEAYSEIGMK

GERRRGKGHDGLYQGLSTATKDTYDALHMQALPPR
```

Additional chimeric signaling molecule sequences

SEQ ID NO: 49, OX40 nt
```
GTTGCCGCCATCCTGGGCCTGGGCCTGGTGCTGGGGCTGCTGGGCCCCCT

GGCCATCCTGCTGGCCCTGTACCTGCTCCGGGACCAGAGGCTGCCCCCCG

ATGCCCACAAGCCCCCTGGGGGAGGCAGTTTCCGGACCCCCATCCAAGAG

GAGCAGGCCGACGCCCACTCCACCCTGGCCAAGATC
```

SEQ ID NO: 50, OX40 aa
```
VAAILGLGLVLGLLGPLAILLALYLLRRDQRLPPDAHKPPGGGSFRTPIQ

EEQADAHSTLAKI
```

SEQ ID NO: 51, SEQ ID NO: 22 nucleotide sequence of 5'LTR sequence
```
TGAAAGACCCCACCTGTAGGTTTGGCAAGCTAGCTTAAGTAACGCCATTT

TGCAAGGCATGGAAAATACATAACTGAGAATAGAAAAGTTCAGATCAAG

GTCAGGAACAGATGGAACAGCTGAATATGGGCCAAACAGGATATCTGTGG

TAAGCAGTTCCTGCCCCGGCTCAGGGCCAAGAACAGATGGAACAGCTGAA

TATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAG
```

-continued

AGAACCATCAGATGTTTCCAGGGTGCCCCAAGGACCTGAAATGACCCTGT

GCCTTATTTGAACTAACCAATCAGTTCGCTTCTCGCTTCTGTTCGCGCGC

TTATGCTCCCCGAGCTCAATAAAAGAGCCCACAACCCCTCACTCGGGGCG

CCAGTCCTCCGATTGACTGAGTCGCCCGGGTACCCGTGTATCCAATAAAC

CCTCTTGCAGTTGCATCCGACTTGTGGTCTCGCTGTTCCTTGGGAGGGTC

TCCTCTGAGTGATTGACTACCCGTCAGCGGGGGTCTTTCA

Additional Sequences

SEQ ID NO, 52 Thosea asigna virus-2A from capsid
protein precursor nucleotide sequence
GCCGAGGGCAGGGGAAGTCTTCTAACATGCGGGGACGTGGAGGAAAATCC

CGGGCCC

SEQ ID NO: 53, Thosea asigna virus-2A from capsid
protein precursor amino acid sequence
AEGRGSLLTCGDVEENPGP SEQ ID NO: 54, 3'LTR nucleotide sequence
TGAAAGACCCCACCTGTAGGTTTGGCAAGCTAGCTTAAGTAACGCCATTT

TGCAAGGCATGGAAAAATACATAACTGAGAATAGAGAAGTTCAGATCAAG

GTCAGGAACAGATGGAACAGCTGAATATGGGCCAAACAGGATATCTGTGG

TAAGCAGTTCCTGCCCCGGCTCAGGGCCAAGAACAGATGGAACAGCTGAA

TATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAG

AGAACCATCAGATGTTTCCAGGGTGCCCCAAGGACCTGAAATGACCCTGT

GCCTTATTTGAACTAACCAATCAGTTCGCTTCTCGCTTCTGTTCGCGCGC

TTCTGCTCCCCGAGCTCAATAAAAGAGCCCACAACCCCTCACTCGGGGCG

CCAGTCCTCCGATTGACTGAGTCGCCCGGGTACCCGTGTATCCAATAAAC

CCTCTTGCAGTTGCATCCGACTTGTGGTCTCGCTGTTCCTTGGGAGGGTC

TCCTCTGAGTGATTGACTACCCGTCAGCGGGGGTCTTTCA

SEQ ID NO: 55, (nucleotide sequence of linker-
F$_v$1-F$_v$2-linker with XhoI/SalI sites, (wobbled
codons lowercase in Fv2))
CTCGAGTCTGGCGGTGGATCCGGAGGCGTTCAAGTAGAAACAATCAGCCC

AGGAGACGGAAGGACTTTCCCCAAACGAGGCCAAACATGCGTAGTTCATT

ATACTGGGATGCTCGAAGATGGAAAAAAGTAGATAGTAGTAGAGACCGA

AACAAACCATTTAAATTTATGTTGGGAAAACAAGAAGTAATAAGGGGCTG

GGAAGAAGGTGTAGCACAAATGTCTGTTGGCCAGCGCGCAAAACTCACAA

TTTCTCCTGATTATGCTTACGGAGCTACCGGCCACCCCGGCATCATACCC

CCTCATGCCACACTGGTGTTTGACGTCGAATTGCTCAAACTGGAAGTCGA

GGGaGTgCAgGTgGAgACgATtAGtCCtGGgGAtGGgAGaAccTTtCCaA

AgCGcGGtCAgACcTGtGTtGTcCAcTAcACcGGtATGCTgGAgGAcGGg

AAgAAgGTgGActcTtcacGcGAtCGcAAtAAgCCtTTcAAgTTcATGcT cGGcAAgCAgGAgGTgATccGGGGgTGGGAgGAgGGcGTgGCtCAgATGT CgGTcGGgCAaCGaGCgAAgCTtACcATcTCaCCcGAcTAcGCgTAtGGg GCaAcGgGGcATcCgGGaATtAtCcCtCCcCAcGCtACgCTcGTaTTcGA tGTgGAgcTcttgAAgCTtGagTCTGGCGGTGGATCCGGAGTCGAC SEQ ID NO: 56, (F$_V$ F$_{VLS}$ amino acid sequence)
LESGGGSGGVQVETISPGDGRTFPKRGQTCVVHYTGMLEDGKKVDSSRDR

NKPFKFMLGKQEVIRGWEEGVAQMSVGQRAKLTISPDYAYGATGHPGIIP

PHATLVFDVELLKLEVEGVQVETISPGDGRTFPKRGQTCVVHYTGMLEDG

KKVDSSRDRNKPFKFMLGKQEVIRGWEEGVAQMSVGQRAKLTISPDYA

YGATGHPGIIPPHATLVFDVELLKLESGGGSGVD

SEQ ID NO: 57, FKBPv36 (Fv1) nucleotide sequence
GGCGTTCAAGTAGAAACAATCAGCCCAGGAGACGGAAGGACTTTCCCCAA

ACGAGGCCAAACATGCGTAGTTCATTATACTGGGATGCTCGAAGATGGAA

AAAAGTAGATAGTAGTAGAGACCGAAACAAACCATTTAAATTTATGTTG

GGAAAACAAGAAGTAATAAGGGGCTGGGAAGAAGGTGTAGCACAAATGTC

TGTTGGCCAGCGCGCAAAACTCACAATTTCTCCTGATTATGCTTACGGAG

CTACCGGCCACCCCGGCATCATACCCCCTCATGCCACACTGGTGTTTGAC

GTCGAATTGCTCAAACTGGAA

SEQ ID NO: 58, FKBPv36 (Fv1) amino acid sequence
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

SEQ ID NO: 59, FKBPv36 (Fv2) nucleotide sequence
GGaGTgCAgGTgGAgACgATtAGtCCtGGgGAtGGgAGaAccTTtCCaAA gCGcGGtCAgACcTGtGTtGTcCAcTAcACcGGtATGCTgGAgGAcGGgA AgAAgGTgGActcTtcacGcGAtCGcAAtAAgCCtTTcAAgTTcATGcTc GGcAAgCAgGAgGTgATccGGGGgTGGGAgGAgGGcGTgGCtCAgATGTC gGTcGGgCAaCGaGCgAAgCTtACcATcTCaCCcGAcTAcGCgTAtGGgG CaAcGgGGcATcCgGGaATtAtCcCtCCcCAcGCtACgCTcGTaTTcGAt GTgGAgcTcttgAAgCTtGag SEQ ID NO: 60, FKBPv36 (Fv2) amino acid sequence
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

Additional Sequences for Inducible MyD88/CD40
Chimeric Polypeptide

SEQ ID NO: 81, Myristoylation polypeptide nucleo-
tide sequence
ATGGGGAGTAGCAAGAGCAAGCCTAAGGACCCCAGCCAGCGC SEQ ID NO: 82, Myristoylation polypeptide amino
acid sequence
MGSSKSKPKDPSQR SEQ ID NO: 83, Linker nucleotide sequence
(linker 1)
CTCGAG SEQ ID NO: 84, Linker amino acid sequence
(linker 1)
LE SEQ ID NO: 85, Truncated MyD88 polypeptide nucleo-
tide sequence
ATGGCCGCTGGGGGCCCAGGCGCCGGATCAGCTGCTCCCGTATCTTCTAC

TTCTTCTTTGCCGCTGGCTGCTCTGAACATGCGCGTGAGAAGACGCCTCT

CCCTGTTCCTTAACGTTCGCACACAAGTCGCTGCCGATTGGACCGCCCTT

```
GCCGAAGAAATGGACTTTGAATACCTGGAAATTAGACAACTTGAAACACA

GGCCGACCCCACTGGCAGACTCCTGGACGCATGGCAGGGAAGACCTGGTG

CAAGCGTTGGACGGCTCCTGGATCTCCTGACAAAACTGGGACGCGACGAC

GTACTGCTTGAACTCGGACCTAGCATTGAAGAAGACTGCCAAAAATATAT

CCTGAAACAACAACAAGAAGAAGCCGAAAAACCTCTCCAAGTCGCAGCAG

TGGACTCATCAGTACCCCGAACAGCTGAGCTTGCTGGGATTACTACACTC

GACGACCCACTCGGACATATGCCTGAAAGATTCGACGCTTTCATTTGCTA

TTGCCCCTCTGACATA

SEQ ID NO: 86, Truncated MyD88 polypeptide amino
acid sequence
MAAGGPGAGSAAPVSSTSSLPLAALNMRVRRRLSLFLNVRTQVAADWTAL

AEEMDFEYLEIRQLETQADPTGRLLDAWQGRPGASVGRLLDLLTKLGRDD

VLLELGPSIEEDCQKYILKQQQEEAEKPLQVAAVDSSVPRTAELAGITTL

DDPLGHMPERFDAFICYCPSDI

SEQ ID NO: 87, ΔCD40 polypeptide nucleotide
sequence
AAGAAAGTTGCAAAGAAACCCACAAATAAAGCCCCACACCCTAAACAGGA

ACCCCAAGAAATCAATTTCCCAGATGATCTCCCTGGATCTAATACTGCCG

CCCCGGTCCAAGAAACCCTGCATGGTTGCCAGCCTGTCACCCAAGAGGAC

GGAAAAGAATCACGGATTAGCGTACAAGAGACAA

SEQ ID NO: 88, ΔCD40 polypeptide amino acid
sequence
KKVAKKPTNKAPHPKQEPQEINFPDDLPGSNTAAPVQETLHGCQPVTQED

GKESRISVQERQ

SEQ ID NO: 89, Linker nucleotide sequence
(linker 2)
GTCGAGTCTGGCGGTGGATCCGGA

SEQ ID NO: 90, Linker amino acid sequence
(linker 2)
VESGGGSG

SEQ ID NO: 91, FKBPv36 (Fv1) nucleotide sequence
GGCGTTCAAGTAGAAACAATCAGCCCAGGAGACGGAAGGACTTTCCCCAA

ACGAGGCCAAACATGCGTAGTTCATTATACTGGGATGCTCGAAGATGGAA

AAAAGTAGATAGTAGTAGAGACCGAAACAAACCATTTAAATTTATGTTG

GGAAAACAAGAAGTAATAAGGGGCTGGGAAGAAGGTGTAGCACAAATGTC

TGTTGGCCAGCGCGCAAAACTCACAATTTCTCCTGATTATGCTTACGGAG

CTACCGGCCACCCCGGCATCATACCCCCTCATGCCACACTGGTGTTTGAC

GTCGAATTGCTCAAACTGGAA

SEQ ID NO: 92, FKBPv36 (Fv1) amino acid sequence
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

SEQ ID NO: 93, Linker nucleotide sequence
(linker 3)
GTCGAG

SEQ ID NO: 94, Linker amino acid sequence
(linker 3)
VE

SEQ ID NO: 95, FKBPv36 (Fv2) nucleotide sequence
GGaGTgCAggTgGAgACgATtAGtCCtGGgGAtGGgAGaACcTTtCCaAA gCGcGGtCAgACcTgTgTtGTcCAcTAcACcGGtATgCTgGAgGAcGGGA AgAAggTgGActcTtcacGcGAtCGcAAtAAgCCtTTcCAgTTcATgCTc GGcAAgCAggAggTgATccGGGGgTGGGAggAgGGcGTgGCtCAgATGTC gGTcGGgCAaCGaGCgAAgCTtACcATcTCaCCcGAcTAcGCgTAtGGgG CaACgGGgCAtCCgGGaATtATcCCtCCcCAcGCtACgCTcGTaTTcGAt GTgGAgcTcttgAAgCTtGag SEQ ID NO: 110, FKBPv36 (Fv2) amino acid sequence
GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE

SEQ ID NO: 96, Linker nucleotide sequence
(linker 4)
TCTGGCGGTGGATCCGGAGTCGAC

SEQ ID NO: 97, Linker amino acid sequence
(linker 4)
SGGGSGVD

SEQ ID NO: 98, Furin protease consensus cleavage
site nucleotide sequence
CGCGCAAAGCGT SEQ ID NO: 99, Furin protease consensus cleavage
site amino acid sequence
RAKR SEQ ID NO: 100, V5 epitope nucleotide sequence
GGAAAACCTATACCTAATCCATTGCTGGGCTTAGACTCAACA SEQ ID NO: 101, V5 epitope nucleotide sequence
GKPIPNPLLGLDST SEQ ID NO: 102, Linker nucleotide sequence
(linker 5)
GGCAGCGGAAGC SEQ ID NO: 103, Linker amino acid sequence
(linker 5)
GSGS SEQ ID NO: 104, P2A nucleotide sequence
GCAACGAATTTTTCCCTGCTGAAACAGGCAGGGGACGTAGAGGAAAATCC

TGGTCCT

SEQ ID NO: 105, P2A amino acid sequence
ATNFSLLKQAGDVEENPGP

SEQ ID NO 106, Linker nucleotide sequence
(linker 6)
ACGCGT

SEQ ID NO: 107, Linker amino acid sequence
(linker 6)
TR

SEQ ID NO: 108, ΔCD19 nucleotide sequence
ATGCCCCCTCCTAGACTGCTGTTTTTCCTGCTCTTTCTCACCCCAATGGA

AGTTAGACCTGAGGAACCACTGGTCGTTAAAGTGGAAGAAGGTGATAATG

CTGTCCTCCAATGCCTTAAAGGGACCAGCGACGGACCAACGCAGCAACTG

ACTTGGAGCCGGGAGTCCCCTCTCAAGCCGTTTCTCAAGCTGTCACTTGG

CCTGCCAGGTCTTGGTATTCACATGCGCCCCCTTGCCATTTGGCTCTTCA

TATTCAATGTGTCTCAACAAATGGGTGGATTCTACCTTTGCCAGCCCGGC
```

```
                              -continued
CCCCCTTCTGAGAAAGCTTGGCAGCCTGGATGGACCGTCAATGTTGAAGG

CTCCGGTGAGCTGTTTAGATGGAATGTGAGCGACCTTGGCGGACTCGGTT

GCGGACTGAAAAATAGGAGCTCTGAAGGACCCTCTTCTCCCTCCGGTAAG

TTGATGTCACCTAAGCTGTACGTGTGGGCCAAGGACCGCCCCGAAATCTG

GGAGGGCGAGCCTCCATGCCTGCCGCCTCGCGATTCACTGAACCAGTCTC

TGTCCCAGGATCTCACTATGGCGCCCGGATCTACTCTTTGGCTGTCTTGC

GGCGTTCCCCCAGATAGCGTGTCAAGAGGACCTCTGAGCTGGACCCACGT

ACACCCTAAGGGCCCTAAGAGCTTGTTGAGCCTGGAACTGAAGGACGACA

GACCCGCACGCGATATGTGGGTAATGGAGACCGGCCTTCTGCTCCCTCGC

GCTACCGCACAGGATGCAGGGAAATACTACTGTCATAGAGGGAATCTGAC

TATGAGCTTTCATCTCGAAATTACAGCACGGCCCGTTCTTTGGCATTGGC

TCCTCCGGACTGGAGGCTGGAAGGTGTCTGCCGTAACACTCGCTTACTTG

ATTTTTTGCCTGTGTAGCCTGGTTGGGATCCTGCATCTTCAGCGAGCCCT

TGTATTGCGCCGAAAAAGAAAACGAATGACTGACCCTACACGACGATTCT

GA

SEQ ID NO: 109, ΔCD19 amino acid sequence
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRF*
```

Example 9: Representative Embodiments

Provided hereafter are examples of certain embodiments of the technology.

A1. A composition which comprises a nucleic acid having a nucleotide sequence that encodes a chimeric protein, wherein the chimeric protein comprises a membrane-targeting region, a multimerizing region and a co-stimulatory polypeptide cytoplasmic signaling region selected from the group consisting of CD27, CD28, ICOS, 4-1BB, and OX40.

A2. The composition of embodiment A1, wherein the chimeric protein further comprises a second co-stimulatory polypeptide cytoplasmic signaling region selected from the group consisting of CD27, CD28, ICOS, 4-1BB, and OX40.

A3. The composition of embodiment A2, wherein the co-stimulatory polypeptide cytoplasmic signaling regions comprise a CD28 cytoplasmic signaling region and a 4-1BB cytoplasmic signaling region.

A4. The composition of embodiment A2, wherein the co-stimulatory polypeptide cytoplasmic signaling regions comprise a CD28 cytoplasmic signaling region polypeptide and a 4-1BB cytoplasmic signaling region polypeptide.

A5. The composition of any of embodiments A1-A4, wherein the chimeric protein further comprises a CD3 ζ polypeptide.

A6. The composition of any of embodiments A1-A5, wherein the multimeric ligand binding region is selected from the group consisting of FKBP ligand-binding region, cyclophilin receptor ligand-binding region, steroid receptor ligand-binding region, cyclophilin receptor ligand-binding region, and tetracycline receptor ligand-binding region.

A7. The composition of any of embodiments A1-A6, wherein the ligand-binding region comprises a $F_vF_{vls}$ amino acid sequence.

A8. The composition of any of embodiments A1-A6, wherein the ligand-binding region comprises a FKBPv36 amino acid sequence.

A9. The composition of embodiment A8, wherein the ligand binding region comprises a $F_v1$ and a $F_v2w$ amino acid sequence.

A10. The composition of any of embodiments A1-A9, wherein the nucleic acid comprises a promoter sequence operably linked to the nucleotide sequence.

A10.1. The composition of embodiment A10, wherein the promoter is developmentally regulated and the chimeric polypeptide is expressed in developmentally differentiated cells.

A10.2. The composition of embodiment A10 or A10.1, wherein the promoter is tissue-specific and the chimeric polypeptide is expressed in the specific tissue.

A10.3. The composition of embodiment A10, wherein the promoter is activated in activated T cells.

A10.4. The composition of any of embodiments A10-A10.3, wherein the promoter comprises a 5'LTR sequence.

A11. The composition of any of embodiments A1-A10, wherein the nucleic acid is contained within a viral vector.

A12. The composition of embodiment A11, wherein the viral vector is a lentiviral vector.

A13. The composition of any of embodiments A1-A10, wherein the nucleic acid is contained within a plasmid.

A14. A cell transformed or transfected with a composition of any of embodiments A1-A13.

A15. The cell of embodiment A14, wherein the cell is a T cell, tumor infiltrating lymphocyte, B cell or NK cell.

A16. The cell of embodiment A15, wherein the cell is transformed or transduced with a nucleic acid comprising a nucleotide sequence that encodes a chimeric protein comprising a signal peptide, a single chain variable fragment, a CH2-CH3 hinge region and a CD3 ζ polypeptide.

A17. The cell of embodiment A16, wherein the single chain variable fragment binds to an antigen on a tumor cell.

A18. The cell of embodiment A16, wherein the single chain variable fragment binds to an antigen on a cell involved in a hyperproliferative disease.

A19. The cell of any of embodiments A17 or A18, wherein the single chain variable fragment is selected from the group consisting of αPSMA, αPSCA, αMUC1, αCD19, αROR1, αMesothelin, αGD2 and αHer2Neu.

A20. The composition of any of embodiments A1-A13, or the cell of any of embodiments A14-A17, wherein the multimerization region binds to a dimeric ligand.

A21. The composition or cell of embodiment A20, wherein the ligand is dimeric FK506, or a dimeric FK506-like analog.

A22. The composition or cell of embodiment A21, wherein the ligand is AP1903.

A23. A method for inducing an immune response, comprising transfecting or transducing a T cell in vitro or ex vivo with a composition of any of embodiments A1-A13.

A24. The method of embodiment A23, further comprising contacting the cell with a ligand that binds to the multimerizing region resulting in multimerization.

A25. The method of embodiment A24, wherein the ligand is dimeric.

A26. The method of embodiment A24, wherein the ligand is dimeric FK506, or a dimeric FK506-like analog.

A27. The method of embodiment A24, wherein the ligand is AP1903.

A28. The method of any of embodiments A23 to A27, further comprising administering the transfected or transformed T cell to a subject.

A29. The method of embodiment A28, wherein the cell is administered to the subject by intradermal or subcutaneous administration.

A30. A method for inducing an immune response in vivo, comprising administering to a subject a composition of any of embodiments A1 to A13.

A31. The method of embodiment A30, further comprising administering to the subject a composition comprising a ligand that binds to the multimerizing region resulting in multimerization.

A32. The method of embodiment A31, wherein the ligand is dimeric.

A33. The method of embodiment A31, wherein the ligand is dimeric FK506, or a dimeric FK506-like analog.

A34. The method of embodiment A31, wherein the ligand is AP1903.

A35. The method of any of embodiments A28 to A34, wherein the subject has been diagnosed with a hyperproliferative disease.

A36. The method of any of embodiments A28 to A34, wherein the subject has been diagnosed with a tumor.

B1. A cell transformed or transfected with a composition comprising a nucleic acid that comprises a polynucleotide encoding an inducible chimeric signaling molecule, wherein the inducible chimeric signaling molecule comprises a membrane targeting region, a multimerizing region, and a truncated MyD88 polypeptide lacking the TIR domain.

B1.1. The cell of embodiment B1, wherein the inducible chimeric signaling molecule further comprises a cytoplasmic CD40 polypeptide lacking the extracellular domain.

B1.2. A cell transformed or transfected with a composition comprising a nucleic acid that comprises a polynucleotide encoding an inducible chimeric signaling molecule, wherein the inducible chimeric signaling molecule comprises a membrane-targeting region, a multimerizing region, and a cytoplasmic CD40 polypeptide lacking the extracellular domain.

B2. The cell of any of embodiments B1 or B1.2, wherein the truncated MyD88 polypeptide has the amino acid sequence of SEQ ID NO: 86, or a functional fragment thereof.

B2.1. The cell of any of embodiments B1.1 or B1.2, wherein the cytoplasmic CD40 polypeptide has the amino acid sequence of SEQ ID NO: 88, or a functional fragment thereof.

B3. The cell of any of embodiments B1-B2.1, wherein the membrane-targeting region is a myristoylation targeting sequence.

B4-B6. Reserved

B7. The cell of any one of embodiments B1-B3, wherein the inducible chimeric signaling molecule further comprises a CD3ζ polypeptide.

B8. The cell of any one of embodiments B1-B7, wherein the multimerizing region is selected from the group consisting of FKBP, cyclophilin receptor, steroid receptor, tetracycline receptor, heavy chain antibody subunit, light chain antibody subunit, and mutated sequences thereof.

B9. The cell of any one of embodiments B1-B8, wherein the multimerizing region is an FKBP12 region.

B10. The cell of any one of embodiments B1-B9, wherein the FKB12 region is an FKB12v36 region.

B11. The cell of any one of embodiments B1-B8, wherein the multimerizing region is Fv'Fvls.

B12. The cell of any one of embodiments B1-B8, wherein the multimerizing region binds a ligand selected from the group consisting of an FK506 dimer and a dimeric FK506 analog ligand.

B13. The cell of any one of embodiments B1-B12, wherein the ligand is AP1903 or AP20187.

B14. The cell of any one of embodiments B1-B13, wherein the multimerizing region has an amino acid sequence of SEQ ID NO: 58 or a functional fragment thereof.

B15. The cell of any one of embodiments B1-B14, wherein the multimerizing region is encoded by a nucleotide sequence in SEQ ID NO: 57, or a functional fragment thereof.

B16. The cell of embodiment B14, wherein the multimerizing region further comprises a polypeptide having an amino acid sequence of SEQ ID NO: 60, or a functional fragment thereof.

B17. The cell of embodiment B15, wherein the multimerizing region further comprises a polypeptide encoded by a nucleotide sequence in SEQ ID NO: 59, or a functional fragment thereof.

B18. The cell of embodiments B14 or B16, wherein the multimerizing region further comprises a polypeptide having an amino acid sequence of SEQ ID NO: 60, or a functional fragment thereof.

B19. The cell of embodiments B15 or B17, wherein the multimerizing region further comprises a polypeptide encoded by a nucleotide sequence in SEQ ID NO: 59, or a functional fragment thereof.

B20. The cell of any one of embodiments B14, B16, or B18, wherein the multimerizing region further comprises a polypeptide having an amino acid sequence of SEQ ID NO: 58 or SEQ ID NO: 60, or a functional fragment thereof.

B21. The cell of any one of embodiments B15, B17, or B19, wherein the multimerizing region further comprises a polypeptide encoded by a nucleotide sequence in SEQ ID NO: 57 or SEQ ID NO: 59, or a functional fragment thereof.

B22. The cell of any one of embodiments B1-B21, wherein the nucleic acid comprises a promoter sequence operably linked to the polynucleotide.

B23. The cell of any one of embodiments B1-B22, wherein the nucleic acid is contained within a viral vector.

B24. The cell of embodiment B23, wherein the viral vector is a retroviral vector.

B25. The cell of embodiment B24, wherein the retroviral vector is a murine leukemia virus vector.

B26. The cell of embodiment B24, wherein the retroviral vector is an SFG vector.

B27. The cell of embodiment B23, wherein the viral vector is an adenoviral vector.

B28. The cell of embodiment B23, wherein the viral vector is a lentiviral vector.

B29. The cell of any one of embodiments B1-B22, wherein the nucleic acid is contained within a plasmid.

B30. Reserved.

B31. The cell of any one of embodiments B1-B30, wherein the cell is a T cell, tumor infiltrating lymphocyte, NK-T cell, or NK cell.

B32. The cell of embodiment B31, wherein the cell is a T cell.

B33. The cell of any one of embodiments B1-B32, wherein the cell is obtained or prepared from bone marrow.

B34. The cell of any one of embodiments B1-B32, wherein the cell is obtained or prepared from umbilical cord blood.

B35. The cell of any one of embodiments B1-B32, wherein the cell is obtained or prepared from peripheral blood.

B36. The cell of any one of embodiments B1-B32, wherein the cell is obtained or prepared from peripheral blood mononuclear cells.

B37. The cell of any one of embodiments B31-B36, wherein the cell is a human cell.

B38. The cell of any one of embodiments B1-B37, wherein the cell is further transformed or transduced with a nucleic acid comprising a polynucleotide that encodes an inducible chimeric signaling molecule comprising a signal peptide, a single chain variable fragment, a CH2-CH3 hinge region and a CD3ζ polypeptide.

B38.1. The cell of embodiment B38, wherein the inducible chimeric signaling molecule does not comprise a CD3ζ polypeptide.

B38.2. The cell of embodiments B38 or B38.1, wherein the inducible chimeric signaling molecule comprises a CD3ζ polypeptide.

B39. The cell of any one of embodiments B38-B38.2, wherein the single chain variable fragment binds to an antigen on a tumor cell.

B40. The cell of any one of embodiments B38-B38.2, wherein the single chain variable fragment binds to an antigen on a cell involved in a hyperproliferative disease.

B41. The cell of any one of embodiments B38-B40, wherein the single chain variable fragment is selected from the group consisting of αPSMA, αPSCA, αMUC1, αCD19, αROR1, αMesothelin, αGD2, αCD123, αMUC16, and αHer2/Neu single chain variable fragments.

B42. The cell of any of embodiments B38-B40, wherein the single chain variable fragment is an αCD19 single chain variable fragment.

B42.1. The cell of any of embodiments B38-B40, wherein the single chain variable fragment is an αPSCA single chain variable fragment.

B43. A method for inducing an immune response, comprising contacting a cell of embodiments B1-B42.1 with a ligand that binds to the multimerizing region resulting in multimerization of the inducible chimeric signaling molecule.

B44. The method of embodiment B43, wherein the cell is contacted with the ligand in vivo.

B45. The method of embodiments B43 or B44, wherein the ligand is dimeric.

B46. The method of embodiment B45, wherein the ligand is dimeric FK506, or a dimeric FK506-like analog.

B47. The method of embodiment B45, wherein the ligand is AP1903 or AP20187.

B48. The method of any one of embodiments B43-B47, further comprising administering the transfected or transformed cell to a subject.

B49. The method of embodiment B48, wherein the cell is administered to the subject by intravenous administration.

B50-B56. Reserved.

B56. The method of any one of embodiments B43-B49, wherein the subject has been diagnosed with a tumor.

B57. The method of any one of embodiments B43-B49, wherein the subject has cancer.

B58 The method of any one of embodiments B43-B49, wherein the subject has a solid tumor.

B59. The method of embodiment B58, wherein the cell is a tumor infiltrating lymphocyte or a T cell.

B60. The method of embodiments B58 or B59, wherein the cell is delivered to the tumor bed.

B61. The method of embodiment B57, wherein the cancer is present in the blood or bone marrow of the subject.

B62. The method of any one of embodiments B43-B49, wherein the subject has a blood or bone marrow disease.

B63. The method of any one of embodiments B43-B49, wherein the subject has been diagnosed with any condition or disorder that can be alleviated by stem cell transplantation.

B64. The method of any one of embodiments B43-B49, wherein the subject has been diagnosed with sickle cell anemia or metachromatic leukodystrophy.

B65. The method of any one of embodiments B43-B49, wherein the patient has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder.

B66. The method of any one of embodiments B43-B49, wherein the condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

B67. A method for treating leukemia in a subject, comprising administering a cell of any one of embodiments B1 to B42.1, and administering a multimeric ligand to the subject.

B68. The method of embodiment B67, wherein the single chain variable fragment binds to CD19.

B69. The method of embodiments B67 or B68, wherein the multimeric ligand is AP1903 or AP20187.

B70. The method of any of embodiments B67-B69, wherein the cell is a T cell.

B71. The method of any one of embodiments B43-B70, wherein the subject is human.

B72. The method of any one of embodiments B43-B71, further comprising determining whether an additional dose of the multimeric ligand should be administered to the subject.

B73. The method of any one of embodiments B43-B72, further comprising administering an additional dose of the multimeric ligand to the subject, wherein the disease or condition symptoms remain or are detected following a reduction in symptoms.

B74. The method of embodiment B73, wherein the subject has been diagnosed with a disease or condition before administration of the cell of any one of embodiments 1-42.1, and after administration of the multimeric ligand the disease or condition is detected, an additional dose of the multimeric ligand is administered to the subject.

B75. The method of any one of embodiments B43-B74, further comprising
identifying the presence, absence or stage of a condition or disease in a subject, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

B76. The method of any one of embodiments B72-B75, wherein the condition is cancer.

B77. The method of any one of embodiments B72-B75, wherein the condition is leukemia.

B78. The method of any one of embodiments B72-B75, wherein the condition is a solid tumor.

B79. The method of embodiment B78, comprising
determining the presence or absence of a tumor size increase and/or increase in the number of tumor cells in a subject relative to the tumor size and/or the number of tumor cells following administration of the multimeric ligand, and
administering an additional dose of the multimeric ligand to the subject in the event the presence of a tumor size increase and/or increase in the number of tumor cells is determined.

B80. The method of embodiment B77, comprising
determining the presence or absence of an increase in CD19-expressing B cells in the subject relative to the level of CD19-expressing B cells following administration of the multimeric ligand, and
administering an additional dose of the multimeric ligand to the subject in the event the presence of an increase in CD19-expressing B cells in the subject is determined.

B81. The method of embodiment B79, wherein the tumor size and/or the number of tumor cells is decreased following administration of the multimeric ligand relative to the tumor size and/or number of tumor cells before administration of the multimeric ligand.

B82. The method of embodiment B80, wherein the level of CD19-expressing B cells is decreased following administration of the multimeric ligand relative to the level of CD19-expressing B cells before administration of the multimeric ligand.

B83. The method of any one of embodiments B43-B74, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

C1. A composition comprising a nucleic acid that comprises a polynucleotide encoding an inducible chimeric antigen receptor, wherein the inducible chimeric antigen receptor comprises a multimerizing region, a truncated MyD88 polypeptide lacking the TIR domain, and a single chain variable fragment.

C1.1. The composition of embodiment C1, wherein the inducible chimeric antigen receptor further comprises a cytoplasmic CD40 polypeptide lacking the extracellular domain.

C1.2. A composition comprising a nucleic acid that comprises a polynucleotide encoding an inducible chimeric antigen receptor, wherein the inducible chimeric antigen receptor comprises a multimerizing region, a cytoplasmic CD40 polypeptide lacking the extracellular domain, and a single chain variable fragment.

C2. The composition of any embodiments C1 or C1.2, wherein the truncated MyD88 polypeptide has the amino acid sequence of SEQ ID NO: 86, or a functional fragment thereof.

C2.1. The composition of any of embodiments C1.1 or C1.2, wherein the cytoplasmic CD40 polypeptide has the amino acid sequence of SEQ ID NO: 88, or a functional fragment thereof.

C3-C6. Reserved

C7. The composition of any one of embodiments C1-C2.1, wherein the inducible chimeric antigen receptor further comprises a CD3ζ polypeptide.

C8. The composition of any one of embodiments C1-C7, wherein the multimerizing region is selected from the group consisting of FKBP, cyclophilin receptor, steroid receptor, tetracycline receptor, heavy chain antibody subunit, light chain antibody subunit, and mutated sequences thereof.

C9. The composition of any one of embodiments C1-C8, wherein the multimerizing region is an FKBP12 region.

C10. The composition of any one of embodiments C1-C9, wherein the multimerizing region is an FKB12v36 region.

C11. The composition of any one of embodiments C1-C8, wherein the multimerizing region is Fv'Fvls.

C12. The composition of any one of embodiments C1-C8, wherein the multimerizing region binds a ligand selected from the group consisting of an FK506 dimer and a dimeric FK506 analog ligand.

C13. The composition of any one of embodiments C1-C12, wherein the ligand is AP1903 or AP20187.

C14. The composition of any one of embodiments C1-C13, wherein the multimerizing region has an amino acid sequence of SEQ ID NO: 58 or a functional fragment thereof.

C15. The composition of any one of embodiments C1-C14, wherein the multimerizing region is encoded by a nucleotide sequence in SEQ ID NO: 57, or a functional fragment thereof.

C16. The composition of embodiment C14, wherein the multimerizing region further comprises a polypeptide having an amino acid sequence of SEQ ID NO: 60, or a functional fragment thereof.

C17. The composition of embodiment C15, wherein the multimerizing region further comprises a polypeptide encoded by a nucleotide sequence in SEQ ID NO: 59, or a functional fragment thereof.

C18. The composition of embodiments C14 or C16, wherein the multimerizing region further comprises a polypeptide having an amino acid sequence of SEQ ID NO: 60, or a functional fragment thereof.

C19. The composition of embodiments C15 or C17, wherein the multimerizing region further comprises a polypeptide encoded by a nucleotide sequence in SEQ ID NO: 59, or a functional fragment thereof.

C20. The composition of any one of embodiments C14, C16, or C18, wherein the multimerizing region further comprises a polypeptide having an amino acid sequence of SEQ ID NO: 58 or SEQ ID NO: 60, or a functional fragment thereof.

C21. The composition of any one of embodiments C15, C17, or C19, wherein the multimerizing region further comprises a polypeptide encoded by a nucleotide sequence in SEQ ID NO: 57 or SEQ ID NO: 59, or a functional fragment thereof.

C22. The composition of any one of embodiments C1-C21, wherein the nucleic acid comprises a promoter sequence operably linked to the polynucleotide.

C23. The composition of any one of embodiments C1-C22, wherein the nucleic acid is contained within a viral vector.

C24. The composition of embodiment C23, wherein the viral vector is a retroviral vector.

C25. The composition of embodiment C24, wherein the retroviral vector is a murine leukemia virus vector.

C26. The composition of embodiment C24, wherein the retroviral vector is an SFG vector.

C27. The composition of embodiment C23, wherein the viral vector is an adenoviral vector.

C28. The composition of embodiment C23, wherein the viral vector is a lentiviral vector.

C29. The composition of any one of embodiments C1-C22, wherein the nucleic acid is contained within a plasmid.

C30. A cell transduced or transformed with a composition of any one of embodiments C1-C29.

C31. The cell of embodiments C30, wherein the cell is a T cell, tumor infiltrating lymphocyte, NK-T cell, or NK cell.

C32. The cell of embodiment C31, wherein the cell is a T cell.

C33. The cell of any one of embodiments C1-C3, wherein the cell is obtained or prepared from bone marrow.

C34. The cell of any one of embodiments C1-C3, wherein the cell is obtained or prepared from umbilical cord blood.

C35. The cell of any one of embodiments C1-C3, wherein the cell is obtained or prepared from peripheral blood.

C36. The cell of any one of embodiments C1-C3, wherein the cell is obtained or prepared from peripheral blood mononuclear cells.

C37. The cell of any one of embodiments C31-C3, wherein the cell is a human cell.

C38. Reserved.

C39. The cell of any one of embodiments C1-C37, wherein the single chain variable fragment binds to an antigen on a tumor cell.

C40. The cell of any one of embodiments C1-C37, wherein the single chain variable fragment binds to an antigen on a cell involved in a hyperproliferative disease.

C41. The cell of any one of embodiments C1-C40, wherein the single chain variable fragment is selected from the group consisting of αPSMA, αPSCA, αMUC1, αCD19, αROR1, αMesothelin, αGD2, αCD123, αMUC16, and αHer2/Neu single chain variable fragments.

C42. The cell of any of embodiments C1-C40, wherein the single chain variable fragment is an αCD19 single chain variable fragment.

C42.1. The cell of any of embodiments C1-C40, wherein the single chain variable fragment is an αPSCA single chain variable fragment.

C43. A method for inducing an immune response, comprising contacting a cell of embodiments C1-C42.1 with a ligand that binds to the multimerizing region resulting in multimerization of the inducible chimeric antigen receptor.

C44. The method of embodiment C43, wherein the cell is contacted with the ligand in vivo.

C45. The method of embodiments C43 or C44, wherein the ligand is dimeric.

C46. The method of embodiment C45, wherein the ligand is dimeric FK506, or a dimeric FK506-like analog.

C47. The method of embodiment C45, wherein the ligand is AP1903 or AP20187.

C48. The method of any one of embodiments C43-C47, further comprising administering the transfected or transformed cell to a subject.

C49. The method of embodiment C48, wherein the cell is administered to the subject by intravenous administration.

C50-056. Reserved.

C56. The method of any one of embodiments C43-C49, wherein the subject has been diagnosed with a tumor.

C57. The method of any one of embodiments C43-C49, wherein the subject has cancer.

C58 The method of any one of embodiments C43-C49, wherein the subject has a solid tumor.

C59. The method of embodiment C58, wherein the cell is a tumor infiltrating lymphocyte or a T cell.

C60. The method of embodiments C58 or C59, wherein the cell is delivered to the tumor bed.

C61. The method of embodiment C57, wherein the cancer is present in the blood or bone marrow of the subject.

C62. The method of any one of embodiments C43-C49, wherein the subject has a blood or bone marrow disease.

C63. The method of any one of embodiments C43-C49, wherein the subject has been diagnosed with any condition or disorder that can be alleviated by stem cell transplantation.

C64. The method of any one of embodiments C43-C49, wherein the subject has been diagnosed with sickle cell anemia or metachromatic leukodystrophy.

C65. The method of any one of embodiments C43-C49, wherein the patient has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder.

C66. The method of any one of embodiments C43-C49, wherein the condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

C67. A method for treating leukemia in a subject, comprising administering a cell of any one of embodiments C1 to C42.1, and administering a multimeric ligand to the subject.

C68. The method of embodiment C67, wherein the single chain variable fragment binds to CD19.

C69. The method of embodiments C67 or C68, wherein the multimeric ligand is AP1903 or AP20187.

C70. The method of any of embodiments C67-C69, wherein the cell is a T cell.

C71. The method of any one of embodiments C43-C70, wherein the subject is human.

C72. The method of any one of embodiments C43-C71, further comprising determining whether an additional dose of the multimeric ligand should be administered to the subject.

C73. The method of any one of embodiments C43-C72, further comprising administering an additional dose of the multimeric ligand to the subject, wherein the disease or condition symptoms remain or are detected following a reduction in symptoms.

C74. The method of embodiment C73, wherein the subject has been diagnosed with a disease or condition before administration of the cell of any one of embodiments 1-42.1, and after administration of the multimeric ligand the disease or condition is detected, an additional dose of the multimeric ligand is administered to the subject.

C75. The method of any one of embodiments C43-C74, further comprising
identifying the presence, absence or stage of a condition or disease in a subject, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

C76. The method of any one of embodiments C72-C75, wherein the condition is cancer.

C77. The method of any one of embodiments C72-C75, wherein the condition is leukemia.

C78. The method of any one of embodiments C72-C75, wherein the condition is a solid tumor.

C79. The method of embodiment C78, comprising
determining the presence or absence of a tumor size increase and/or increase in the number of tumor cells in a subject relative to the tumor size and/or the number of tumor cells following administration of the multimeric ligand, and
administering an additional dose of the multimeric ligand to the subject in the event the presence of a tumor size increase and/or increase in the number of tumor cells is determined.

C80. The method of embodiment C77, comprising
determining the presence or absence of an increase in CD19-expressing B cells in the subject relative to the level of CD19-expressing B cells following administration of the multimeric ligand, and
administering an additional dose of the multimeric ligand to the subject in the event the presence of an increase in CD19-expressing B cells in the subject is determined.

C81. The method of embodiment C79, wherein the tumor size and/or the number of tumor cells is decreased following administration of the multimeric ligand relative to the tumor size and/or number of tumor cells before administration of the multimeric ligand.

C82. The method of embodiment C80, wherein the level of CD19-expressing B cells is decreased following administration of the multimeric ligand relative to the level of CD19-expressing B cells before administration of the multimeric ligand.

C83. The method of any one of embodiments C43-C74, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

D1. A composition, comprising a nucleic acid that comprises a polynucleotide encoding an inducible chimeric signaling molecule, wherein the inducible chimeric signaling molecule comprises a membrane-targeting region, a multimerizing region and a co-stimulatory polypeptide cytoplasmic signaling region selected from the group consisting of CD27, CD28, ICOS, 4-1BB, CD40, RANK/TRANCE-R, CD3 zeta chain, and OX40.

D2. The composition of embodiment D1, wherein the membrane-targeting region is selected from the group consisting of myristoylation-targeting sequence, palmitoylation-targeting sequence, prenylation sequences (i.e., farnesylation, geranyl-geranylation, CAAX Box), protein-protein interaction motifs and transmembrane sequences (utilizing signal peptides) from receptors.

D3. The composition of embodiments D1 or D2, wherein the membrane-targeting region is a myristoylation targeting sequence.

D4. The composition of any one of embodiments D1-D3, wherein the inducible chimeric signaling molecule further comprises a second co-stimulatory polypeptide cytoplasmic signaling region selected from the group consisting of CD27, CD28, ICOS, 4-1BB, CD40, RANK/TRANCE-R, CD3 zeta chain, and OX40.

D5. The composition of any one of embodiments D1-D4, wherein the co-stimulatory polypeptide cytoplasmic signaling regions comprise a CD28 cytoplasmic signaling region and a 4-1BB cytoplasmic signaling region.

D6. The composition of any one of embodiments D1-D5, wherein the co-stimulatory polypeptide cytoplasmic signaling regions comprise an OX40 cytoplasmic signaling region polypeptide and a 4-1BB cytoplasmic signaling region polypeptide.

D7. The composition of any one of embodiments D1-D6, wherein the inducible chimeric signaling molecule further comprises a CD3ζ polypeptide.

D8. The composition of any one of embodiments D1-D7, wherein the multimerizing region is selected from the group consisting of FKBP, cyclophilin receptor, steroid receptor, tetracycline receptor, heavy chain antibody subunit, light chain antibody subunit, and mutated sequences thereof.

D9. The composition of any one of embodiments D1-8, wherein the multimerizing region is an FKBP12 region.

D10. The composition of any one of embodiments D1-8, wherein the FKB12 region is an FKB12v36 region.

D11. The composition of any one of embodiments D1-8, wherein the multimerizing region is Fv'Fvls.

D12. The composition of any one of embodiments D1-8, wherein the multimerizing region binds a ligand selected from the group consisting of an FK506 dimer and a dimeric FK506 analog ligand.

D13. The composition of any one of embodiments D1-D12, wherein the ligand is AP1903 or AP20187.

D14. The composition of any one of embodiments D1-D13, wherein the multimerizing region has an amino acid sequence of SEQ ID NO: 58 or a functional fragment thereof.

D15. The composition of any one of embodiments D1-D14, wherein the multimerizing region is encoded by a nucleotide sequence in SEQ ID NO: 57, or a functional fragment thereof.

D16. The composition of embodiment D14, wherein the multimerizing region further comprises a polypeptide having an amino acid sequence of SEQ ID NO: 60, or a functional fragment thereof.

D17. The composition of embodiment D15, wherein the multimerizing region further comprises a polypeptide encoded by a nucleotide sequence in SEQ ID NO: 59, or a functional fragment thereof.

D18. The composition of embodiments D14 or D16, wherein the multimerizing region further comprises a polypeptide having an amino acid sequence of SEQ ID NO: 60, or a functional fragment thereof.

D19. The composition of embodiments D15 or D17, wherein the multimerizing region further comprises a polypeptide encoded by a nucleotide sequence in SEQ ID NO: 59, or a functional fragment thereof.

D20. The composition of any one of embodiments D14, D16, or D18, wherein the multimerizing region further comprises a polypeptide having an amino acid sequence of SEQ ID NO: 58 or SEQ ID NO: 60, or a functional fragment thereof.

D21. The composition of any one of embodiments D15, D17, or D19, wherein the multimerizing region further comprises a polypeptide encoded by a nucleotide sequence in SEQ ID NO: 57 or SEQ ID NO: 59, or a functional fragment thereof.

D22. The composition of any one of embodiments D1-D21, wherein the nucleic acid comprises a promoter sequence operably linked to the polynucleotide.

D23. The composition of any one of embodiments D1-D22, wherein the nucleic acid is contained within a viral vector.

D24. The composition of embodiment D23, wherein the viral vector is a retroviral vector.

D25. The composition of embodiment D24, wherein the retroviral vector is a murine leukemia virus vector.

D26. The composition of embodiment D25, wherein the murine leukemia virus vector is a MoMLV vector.

D27. The composition of embodiment D26, wherein the retroviral vector is an SFG vector.

D28. The composition of embodiment D23, wherein the viral vector is an adenoviral vector or a lentiviral vector.

D29. The composition of any one of embodiments D1-D22, wherein the nucleic acid is contained within a plasmid.

D30. A cell transformed or transfected with a composition of any one of embodiments D1-D29.

D31. The cell of embodiment D30, wherein the cell is a T cell, tumor infiltrating lymphocyte, B cell, NK cell, or NK-T cell D32. The cell of embodiment D30, wherein the cell is a T cell.

D33. The cell of embodiment D30, wherein the cell is obtained or prepared from bone marrow.

D34. The cell of embodiment D30, wherein the cell is obtained or prepared from umbilical cord blood.

D35. The cell of embodiment D30, wherein the cell is obtained or prepared from peripheral blood.

D36. The cell of embodiment D30, wherein the cell is obtained or prepared from peripheral blood mononuclear cells.

D37. The cell of any one of embodiments D30-D36, wherein the cell is a human cell.

D38. The cell of any one of embodiments D30-D37, wherein the cell is further transformed or transduced with a nucleic acid comprising a polynucleotide that encodes a chimeric polypeptide comprising a signal peptide, a single chain variable fragment, a CH2-CH3 hinge region and a CD3ζ polypeptide.

D39. The cell of embodiment D38, wherein the single chain variable fragment binds to an antigen on a tumor cell.

D40. The cell of embodiment D39, wherein the single chain variable fragment binds to an antigen on a cell involved in a hyperproliferative disease.

D41. The cell of any one of embodiments D38-D40, wherein the single chain variable fragment is selected from the group consisting of αPSMA, αPSCA, αMUC1, αCD19, αROR1, αMesothelin, αGD2, αCD123, αMUC16, and αHer2/Neu single chain variable fragments.

D42. The cell of any of embodiments D38-D40, wherein the single chain variable fragment is an αCD19 single chain variable fragment.

D43. A method for inducing an immune response, comprising transfecting or transducing a cell in vitro or ex vivo with a composition of any one of embodiments D1-D29.

D44. The method of embodiment D43, further comprising contacting the cell with a ligand that binds to the multimerizing region resulting in multimerization of the inducible chimeric signaling molecule.

D45. The method of embodiment D44, wherein the ligand is dimeric.

D46. The method of embodiment D44, wherein the ligand is dimeric FK506, or a dimeric FK506-like analog.

D47. The method of embodiment D44, wherein the ligand is AP1903 or AP20187.

D48. The method of any one of embodiments D43-D47, further comprising administering the transfected or transformed cell to a subject.

D49. The method of embodiment D48, wherein the cell is administered to the subject by intravenous administration.

D50. A method for inducing an immune response in vivo, comprising administering to a subject a composition of any one of embodiments D1-D29.

D51. The method of embodiment D50, further comprising administering to the subject a composition comprising a ligand that binds to the multimerizing region resulting in multimerization of the inducible chimeric signaling molecule.

D52. The method of embodiment D51, wherein the ligand is dimeric.

D53. The method of embodiment D51, wherein the ligand is dimeric FK506, or a dimeric FK506-like analog.

D54. The method of embodiment D51, wherein the ligand is AP1903 or AP20187.

D55. The method of any one of embodiments D48-D54, wherein the subject has been diagnosed with a hyperproliferative disease.

D56. The method of any one of embodiments D48-D54, wherein the subject has been diagnosed with a tumor.

D57. The method of any one of embodiments D48-D54, wherein the subject has cancer.

D58 The method of any one of embodiments D48-D54, wherein the subject has a solid tumor.

D59. The method of embodiment D58, wherein the cell is a tumor infiltrating lymphocyte or a T cell.

D60. The method of embodiments D58 or D59, wherein the cell is delivered to the tumor bed.

D61. The method of embodiment D57, wherein the cancer is present in the blood or bone marrow of the subject.

D62. The method of any one of embodiments D48-D54, wherein the subject has a blood or bone marrow disease.

D63. The method of any one of embodiments D48-D54, wherein the subject has been diagnosed with any condition or disorder that can be alleviated by stem cell transplantation.

D64. The method of any one of embodiments D48-D54, wherein the subject has been diagnosed with sickle cell anemia or metachromatic leukodystrophy.

D65. The method of any one of embodiments D48-D54, wherein the subject has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder.

D66. The method of any one of embodiments D48-D54, wherein the subject has been diagnosed with a condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

D67. A method for treating leukemia in a subject, comprising administering a composition of embodiment D38, and administering a multimeric ligand to the subject.

D68. The method of embodiment D67, wherein the single chain variable fragment binds to CD19.

D69. The method of embodiments D67 or D68, wherein the multimeric ligand is AP1903 or AP20187.

D70. The method of any of embodiments D67-D69, wherein the cell is a T cell.

D71. The method of any one of embodiments D43-D70, wherein the subject is human.

D72. The method of any one of embodiments D43-D71, further comprising determining whether an additional dose of the multimeric ligand should be administered to the subject.

D73. The method of any one of embodiments D43-D72, further comprising administering an additional dose of the multimeric ligand to the subject, wherein the disease or condition symptoms remain or are detected following a reduction in symptoms.

D74. The method of embodiment D73, wherein the subject has been diagnosed with a disease or condition before administration of the composition or cell of any one of embodiments D1-D42, and after administration of the multimeric ligand the disease or condition is detected, an additional dose of the multimeric ligand is administered to the subject.

D75. The method of any of embodiments D43-D74, further comprising
identifying the presence, absence or stage of a condition or disease in a subject, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

D76. The method of any one of embodiments D72-D75, wherein the condition is cancer.

D77. The method of any one of embodiments D72-D75, wherein the condition is leukemia.

D78. The method of any one of embodiments D72-D75, wherein the condition is a solid tumor.

D79. The method of embodiment D78, comprising
determining the presence or absence of a tumor size increase and/or increase in the number of tumor cells in a subject relative to the tumor size and/or the number of tumor cells following administration of the multimeric ligand, and
administering an additional dose of the multimeric ligand to the subject in the event the presence of a tumor size increase and/or increase in the number of tumor cells is determined.

D80. The method of embodiment D77, comprising
determining the presence or absence of an increase in CD19-expressing B cells in the subject relative to the level of CD19-expressing B cells following administration of the multimeric ligand, and
administering an additional dose of the multimeric ligand to the subject in the event the presence of an increase in CD19-expressing B cells in the subject is determined.

D81. The method of embodiment D79, wherein the tumor size and/or the number of tumor cells is decreased following administration of the multimeric ligand relative to the tumor size and/or number of tumor cells before administration of the multimeric ligand.

D82. The method of embodiment D80, wherein the level of CD19-expressing B cells is decreased following administration of the multimeric ligand relative to the level of CD19-expressing B cells before administration of the multimeric ligand.

D83. The method of any one of embodiments D48-D74, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. An isolated cell, comprising a nucleic acid that comprises a polynucleotide encoding a chimeric signaling molecule, wherein:
   a) the cell is selected from the group consisting of T cells, NK T cells, and NK cells; and
   b) the chimeric signaling molecule comprises
      i) a membrane targeting region,
      ii) an intracellular FKBP12 multimerizing region that binds to a multimeric ligand, wherein the multimeric ligand is AP1903 or AP20187,
      iii) a first co-stimulatory polypeptide cytoplasmic signaling region selected from the group consisting of CD27, CD28, CD40, ICOS, 4-1BB, CD40, RANK/TRANCE-R, and OX40; and
      iv) a second co-stimulatory polypeptide cytoplasmic signaling region selected from the group consisting of CD27, CD28, CD40, ICOS, 4-1BB, CD40, RANK/TRANCE-R, and OX40;
      wherein the chimeric signaling molecule does not have a functional extracellular domain.

2. The isolated cell of claim 1, wherein the membrane-targeting region is a myristoylation-targeting sequence.

3. The isolated cell of claim 1, wherein the co-stimulatory polypeptide cytoplasmic signaling regions comprise a CD28 cytoplasmic signaling region and a 4-1 BB cytoplasmic signaling region.

4. The isolated cell of claim 1, wherein the FKBP12 multimerizing region comprises a modified FKBP12 polypeptide comprising an amino acid substitution at position 36 that binds with higher affinity to the multimeric ligand than the wild type FKBP12 polypeptide.

5. The isolated cell of claim 1, wherein the FKBP12 multimerizing region is Fv'Fvls.

6. The isolated cell of claim 1, wherein the FKBP12 multimerizing region comprises a FKBP12 polypeptide comprising a valine at position 36.

7. The isolated cell of claim 1, wherein the FKBP12 multimerizing region comprises two FKBP12v36 regions.

8. The isolated cell of claim 1, wherein the nucleic acid further comprises a promoter sequence operably linked to the polynucleotide.

9. The isolated cell of claim 4, wherein the modified FKBP12 polypeptide binds with higher affinity to AP1903 than the wild type FKBP12 polypeptide.

10. The isolated cell of claim 4, wherein the modified FKBP12 polypeptide binds with higher affinity to AP20187 than the wild type FKBP12 polypeptide.

11. The isolated cell of claim 1, wherein the cell is a T cell.

12. A method for making a cell comprising a nucleic acid that comprises a polynucleotide that encodes a chimeric signaling molecule, comprising
   transfecting or transducing a T cell, an NK T cell, or an NK cell in vitro or ex vivo with a nucleic acid that comprises a polynucleotide that encodes the chimeric signaling molecule, wherein the chimeric signaling molecule comprises
      i) a membrane targeting region,
      ii) an intracellular FKBP12 multimerizing region that binds to a multimeric ligand, wherein the multimeric ligand is AP1903 or AP20187,
      iii) a first co-stimulatory polypeptide cytoplasmic signaling region selected from the group consisting of CD27, CD28, CD40, ICOS, 4-1BB, CD40, RANK/TRANCE-R, and OX40; and
      iv) a second co-stimulatory polypeptide cytoplasmic signaling region selected from the group consisting of CD27, CD28, CD40, ICOS, 4-1BB, CD40, RANK/TRANCE-R, and OX40,
      wherein the chimeric signaling molecule does not have a functional extracellular domain.

13. The method of claim 12, wherein the co-stimulatory polypeptide cytoplasmic signaling regions comprise a CD28 cytoplasmic signaling region and a 4-1BB cytoplasmic signaling region.

14. The isolated cell of claim 1, wherein the chimeric signaling molecule does not have an extracellular domain.

15. The method of claim 12, wherein the chimeric signaling molecule does not have an extracellular domain.

* * * * *